(12) United States Patent
Omenetto et al.

(10) Patent No.: US 10,513,802 B2
(45) Date of Patent: Dec. 24, 2019

(54) PEPTIDE-BASED NANOFIBRILLAR MATERIALS

(71) Applicant: Tufts University, Medford, MA (US)

(72) Inventors: Fiorenzo G. Omenetto, Lexington, MA (US); David L. Kaplan, Concord, MA (US); Benedetto Marelli, Lexington, MA (US); Alexander Nicholas Mitropoulos, Winchester, MA (US)

(73) Assignee: Tufts University, Medford, MA (US)

( * ) Notice: Subject to any disclaimer, the term of this patent is extended or adjusted under 35 U.S.C. 154(b) by 612 days.

(21) Appl. No.: 15/034,983

(22) PCT Filed: Nov. 7, 2014

(86) PCT No.: PCT/US2014/064696
§ 371 (c)(1),
(2) Date: May 6, 2016

(87) PCT Pub. No.: WO2015/070108
PCT Pub. Date: May 14, 2015

(65) Prior Publication Data
US 2016/0281266 A1 Sep. 29, 2016

Related U.S. Application Data

(60) Provisional application No. 61/902,145, filed on Nov. 8, 2013.

(51) Int. Cl.
*A61K 38/17* (2006.01)
*D01F 4/02* (2006.01)
(Continued)

(52) U.S. Cl.
CPC ............. *D01F 4/02* (2013.01); *A61L 27/227* (2013.01); *A61L 27/3604* (2013.01); *A61L 27/56* (2013.01); *C07K 14/78* (2013.01); *C08J 9/28* (2013.01); *C12Q 1/26* (2013.01); *C12Q 1/28* (2013.01); *A61L 2400/12* (2013.01);
(Continued)

(58) Field of Classification Search
USPC .......... 530/353; 528/328; 977/762; 264/464, 264/465; 428/36.4, 304.4, 364, 401
See application file for complete search history.

(56) References Cited

U.S. PATENT DOCUMENTS 5,245,012 A    9/1993  Lombari et al.
2004/0067503 A1  4/2004  Tan et al.
(Continued)

FOREIGN PATENT DOCUMENTS

CN    103285424 A  *  9/2013
JP    2010013743 A  *  1/2010
(Continued)

OTHER PUBLICATIONS

Altman, G.H. et al., Silk-based biomaterials, Biomaterials, 24(3): 401-416 (2003).
(Continued)

*Primary Examiner* — Matthew D Matzek
(74) *Attorney, Agent, or Firm* — Quarles & Brady LLP; James Schleicher

(57) ABSTRACT

Disclosed herein are nanofibrillar materials and aerogel-like materials comprised of nanofibrils, and methods for making such materials.

12 Claims, 16 Drawing Sheets
Specification includes a Sequence Listing.

(51) Int. Cl.
| | |
|---|---|
| C07K 14/78 | (2006.01) |
| C08J 9/28 | (2006.01) |
| A61L 27/22 | (2006.01) |
| A61L 27/36 | (2006.01) |
| A61L 27/56 | (2006.01) |
| C12Q 1/26 | (2006.01) |
| C12Q 1/28 | (2006.01) |
| B82Y 40/00 | (2011.01) |
| D01F 4/00 | (2006.01) |
| B82Y 30/00 | (2011.01) |

(52) U.S. Cl.
CPC ............... B82Y 30/00 (2013.01); B82Y 40/00 (2013.01); C08J 2205/022 (2013.01); C08J 2207/10 (2013.01); C08J 2389/02 (2013.01); D01F 4/00 (2013.01)

(56) References Cited

U.S. PATENT DOCUMENTS

| | | | | |
|---|---|---|---|---|
| 2006/0273279 | A1* | 12/2006 | Kaplan | A61L 27/227 252/1 |
| 2013/0115457 | A1* | 5/2013 | Haynie | D01D 5/003 428/401 |
| 2016/0274030 | A1* | 9/2016 | Ruckh | G01N 21/6428 |

FOREIGN PATENT DOCUMENTS

| | | |
|---|---|---|
| WO | WO-1997/008315 A1 | 3/1997 |
| WO | WO-2004/062697 A2 | 7/2004 |
| WO | WO-2004/080346 A2 | 9/2004 |
| WO | WO-2005/012606 A2 | 2/2005 |
| WO | WO-2005/123114 A2 | 12/2005 |
| WO | WO-2007/016524 A2 | 2/2007 |
| WO | WO-2008/118133 A2 | 10/2008 |
| WO | WO-2008/150861 A1 | 12/2008 |
| WO | WO-2011/130335 A2 | 10/2011 |
| WO | WO-2014/145002 A2 | 9/2014 |
| WO | WO-2015/070108 A1 | 5/2015 |

OTHER PUBLICATIONS

Ayers, M.R. and Hunt, A.J., Molecular oxygen sensors based on photoluminescent silica aerogels, Journal of Non-Crystalline Solids, 225:343-347 (1998).
Bhardwaj, N. and Kundu, S.C., Electronspinning: a fascinating fiber fabrication technique, Biotechnology Advances, 28:325-347 (2010).
Cao, J. and Wang, B., Biodegradation of silk biomaterials, International Journal of Molecular Sciences, 10:1514-1524 (2009).
Cherny, I. and Gazit, E., Amyloids: not only pathological agents but also ordered nanomaterials, Angewandte Chemie International Edition in English, 47(22):4062-4069 (2008).
Domigan, L.J. et al., Controlling the dimensions of amyloid fibrils: toward homogenous components for bionanotechnology, Biopolymers, 97(2)L123-133 (2012).
Fischer, F. et al., Cellulose-based aerogels, Polymer, 47(22):7636-7645 (2006).
Floren, M. et al., Carbon Dioxide Induced Silk Protein Gelation for Biomedical Applications, Biomacromolecules, 13:2060-2072 (2012).
Frenot, A. and Chronakis, I.S., Polymer nanofibers assembled by electrospinning, Current Opinion in Colloid and Interface Science, 8:64-75 (2003).
Gesser, H.D. and Goswami, P.C., Aerogels and related porous materials, Chemical Reviews, 89(4):765-788 (1989).
Hrubesh, L.W., Aerogel applications, Journal of Non-Crystalline Solids, 225:335-342 (1998).
Hu, X. et al., Determining beta-sheet crystallinity in fibrous proteins by thermal analysis and infrared spectroscopy, Macromolecules, 39:6161-6170 (2009).

International Search Report for PCT/US2014/064696, 4 pages (dated Feb. 27, 2015).
Jin, H.J. and Kaplan, D.L., Mechanism of silk processing in insects and spiders, Nature, 424:1057-1061 (2003).
Kazarian, S.G., Polymer processing with supercritical fluids, Polymer Science, 42(1):78-101 (2000).
Kikuchi, Y. et al., Structure of the Bombyx mori fibroin light-chain-encoding gene: upstream sequence elements common to the light and heavy chain, Gene, 110(2):151-158 (1992).
Kim, S. et al., All-water-based electron-beam lithograph using silk as a resist, Nature Nanotechnology, 9(4):306-310 (2014).
Kojic, N. et al., Ion electrodiffusion governs silk electrogelation, Soft Matter, 8(26):6897-6905 (2012).
Lawrence, B.D. et al., Bioactive silk protein biomaterial systems for optical devices, Biomacromolecules, 9:1214-1220 (2008).
Lu, Q. et al., Nanofibrous architecture of silk fibroin scaffolds prepared with a mild self-assembly process, Biomaterials, 32:1059-1067 (2011).
Lucas, F. et al., The silk fibroins, Advanced Protein Chemistry, 13:107-242 (1958).
Lutolf, M.P. and Hubbell, J.A., Synthetic biomateirals as instructive extracellular microenvironments for morphogenesis in tissue engineering, Nature Biotechnology, 23(1):47-55 (2005).
Marin, M.A. et al., Silk fibroin aerogels for drug delivery application, The Journal of Supercritical Fluids, 91:84-89 (2014).
Meersman, F. et al., Protein unfolding, amyloid fibril formation and configurational energy landscape under high pressure conditions, Chemical Society Reviews, 35(10):908-917 (2006).
Nagarkar, S. et al., Structure and gelation mechanism of silk hydrogels, Physical Chemistry Chemical Physics, 12:3834-3844 (2010).
Nilsson, M.R., Techniques to study amyloid fibril formation in vitro, Methods, 34(1):151-160 (2004).
Omenetto, F.G. and Kaplan, D.L., New opportunities for an ancient material, Science, 329(5991):528-531 (2010).
Rockwood, D.N. et al., Materials fabrication from Bombyx mori silk fibroin, Nature Protocols, 6(10):1612-1631 (2011).
Sashina, E.S. et al., Structure and solubility of natural silk fibroin, Russian Journal of Applied Chemistry, 79(6):869-876 (2006).
Sing, N. H. and Schubert, U., Aerogels—airy materials: chemistry, structure, and properties, Angewadnte Chemie, 37(1-2):22-45 (1998).
Takei, F. et al., Further evidence for importance of the subunit combination of silk fibroin in its efficient secretion from the posterior silk gland cells, The Journal of Cell Biology, 105(1):175-180 (1987).
Tanaka, K. et al., Determination of the site of disulfide linkage between heavy and light chains of silk fibroin produced by Bombyx mori, Biochimica et Biophysica Acta, 1432:92-103 (1999).
Tanaka, K. et al., Immunological identification of the major disulfide-linked light component of silk fibroin, The Journal of Biochemistry, 114:1-4 (1993).
Tao, H. et al., Silk Materials—A Road to Sustainable High technology, Advanced Materials, 24:2824-2837 (2012).
Torrent, J. et al., High pressure induces scrapie-like prion protein misfolding and amyloid fibril formation, Biochemistry, 43(22):7162-7170 (2004).
Wang, Y. et al., In vivo degradation of three-dimensional silk fibroin scaffolds, Biomaterials, 29:3415-3428 (2008).
Waterhouse, S.H. and Gerrard, J.A., Amyloid fibrils in bionanotechnology, Australian Journal of Chemistry, 57:525-530 (2004).
Williams, J.R. et al., Supercritical fluids and their applications in biotechnology and related areas, Molecular Biotechnology, 22(3):263-286 (2002).
Wray, L.S. et al., Effect of processing on silk-based biomaterials: reproducibility and biocompatibility, 99(1):89-101 (2011).
Written Opinion for PCT/US2014/064696, 6 pages (dated Feb. 27, 2015).
Zarkoob, S. et al., Structure and morphology of nano electrospun silk fibers, American Chemical Society Division of Polymer Chemistry, 39:244-245 (1998).
Zhang, F. et al., Silk dissolution and regeneration at the nanofibril scale, Journal of Materials Chemistry B, 2:3876-3885 (2014).

(56) References Cited

OTHER PUBLICATIONS

Zhao, Z. et al., Generation of Silk Fibroin Nanoparticles via Solution-Enhanced Dispersion by Supercritical CO2, Industrial & Engineering Chemistry Research, 52:3752-3761 (2013).

* cited by examiner

SEQUENCE LISTING

<160> NUMBER OF SEQ ID NOS: 22

<210> SEQ ID NO 1
<211> LENGTH: 90
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (7)..(90)
<223> OTHER INFORMATION: Wherein any of residues 7-90 may be missing.

<400> SEQUENCE: 1

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
            20                  25                  30

Gly Ala Gly Ser Gly Ala Gly Ala Gly Ser Gly Ala Gly Ala Gly Ser
        35                  40                  45

Gly Ala Gly Ala Gly Ser Gly Ala Gly Ala Gly Ser Gly Ala Gly Ala
    50                  55                  60

Gly Ser Gly Ala Gly Ala Gly Ser Gly Ala Gly Ala Gly Ser Gly Ala
65                  70                  75                  80

Gly Ala Gly Ser Gly Ala Gly Ala Gly Ser
                85                  90

<210> SEQ ID NO 2
<211> LENGTH: 30
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Wherein X is V, I or A.
<220> FEATURE:
<221> NAME/KEY: MISC_FEATURE
<222> LOCATION: (3)..(30)
<223> OTHER INFORMATION: Wherein any of residues 3-30 may be missing
<220> FEATURE:
<221> NAME/KEY: MISC_FEATURE
<222> LOCATION: (4)..(4)
<223> OTHER INFORMATION: Wherein X is V, I or A.
<220> FEATURE:
<221> NAME/KEY: MISC_FEATURE
<222> LOCATION: (6)..(6)
<223> OTHER INFORMATION: Wherein X is V, I or A.
<220> FEATURE:
<221> NAME/KEY: MISC_FEATURE
<222> LOCATION: (8)..(8)
<223> OTHER INFORMATION: Wherein X is V, I or A.
<220> FEATURE:
<221> NAME/KEY: MISC_FEATURE
<222> LOCATION: (10)..(10)
<223> OTHER INFORMATION: Wherein X is V, I or A.
<220> FEATURE:
<221> NAME/KEY: MISC_FEATURE
<222> LOCATION: (12)..(12)
<223> OTHER INFORMATION: Wherein X is V, I or A.
<220> FEATURE:
<221> NAME/KEY: MISC_FEATURE
<222> LOCATION: (14)..(14)
<223> OTHER INFORMATION: Wherein X is V, I or A.
<220> FEATURE:
<221> NAME/KEY: MISC_FEATURE
<222> LOCATION: (16)..(16)
<223> OTHER INFORMATION: Wherein X is V, I or A.
<220> FEATURE:
<221> NAME/KEY: MISC_FEATURE

```
<222> LOCATION: (18)..(18)
<223> OTHER INFORMATION: Wherein X is V, I or A.
<220> FEATURE:
<221> NAME/KEY: MISC_FEATURE
<222> LOCATION: (20)..(20)
<223> OTHER INFORMATION: Wherein X is V, I or A.
<220> FEATURE:
<221> NAME/KEY: MISC_FEATURE
<222> LOCATION: (22)..(22)
<223> OTHER INFORMATION: Wherein X is V, I or A.
<220> FEATURE:
<221> NAME/KEY: MISC_FEATURE
<222> LOCATION: (24)..(24)
<223> OTHER INFORMATION: Wherein X is V, I or A.
<220> FEATURE:
<221> NAME/KEY: MISC_FEATURE
<222> LOCATION: (26)..(26)
<223> OTHER INFORMATION: Wherein X is V, I or A.
<220> FEATURE:
<221> NAME/KEY: MISC_FEATURE
<222> LOCATION: (28)..(28)
<223> OTHER INFORMATION: Wherein X is V, I or A.
<220> FEATURE:
<221> NAME/KEY: MISC_FEATURE
<222> LOCATION: (30)..(30)
<223> OTHER INFORMATION: Wherein X is V, I or A.

<400> SEQUENCE: 2

Gly Xaa Gly Xaa Gly Xaa Gly Xaa Gly Xaa Gly Xaa Gly Xaa Gly Xaa
1               5                   10                  15

Gly Xaa Gly Xaa Gly Xaa Gly Xaa Gly Xaa Gly Xaa Gly Xaa
            20                  25                  30

<210> SEQ ID NO 3
<211> LENGTH: 4
<212> TYPE: PRT
<213> ORGANISM: Bombyx mori

<400> SEQUENCE: 3

Gly Ala Ala Ser
1

<210> SEQ ID NO 4
<211> LENGTH: 15
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Wherein residue S may be missing
<220> FEATURE:
<221> NAME/KEY: MISC_FEATURE
<222> LOCATION: (14)..(15)
<223> OTHER INFORMATION: Wherein any of residues 14-15 may be missing

<400> SEQUENCE: 4

Ser Ser Ala Ala Ala Ala Ala Ala Ala Ala Ala Ala Ala Ala Ala
1               5                   10                  15

<210> SEQ ID NO 5
<211> LENGTH: 8
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(5)
<223> OTHER INFORMATION: Wherein any of residues 2-5 may be missing
<220> FEATURE:
```

```
<221> NAME/KEY: MISC_FEATURE
<222> LOCATION: (2)..(2)
<223> OTHER INFORMATION: Wherein X is any residue
<220> FEATURE:
<221> NAME/KEY: MISC_FEATURE
<222> LOCATION: (3)..(3)
<223> OTHER INFORMATION: Wherein X is any residue
<220> FEATURE:
<221> NAME/KEY: MISC_FEATURE
<222> LOCATION: (4)..(4)
<223> OTHER INFORMATION: Wherein X is any residue
<220> FEATURE:
<221> NAME/KEY: MISC_FEATURE
<222> LOCATION: (5)..(5)
<223> OTHER INFORMATION: Wherein X is any residue
<220> FEATURE:
<221> NAME/KEY: MISC_FEATURE
<222> LOCATION: (8)..(8)
<223> OTHER INFORMATION: Wherein X is any residue

<400> SEQUENCE: 5

Gly Xaa Xaa Xaa Xaa Gly Gly Xaa
1               5

<210> SEQ ID NO 6
<211> LENGTH: 4
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (4)..(4)
<223> OTHER INFORMATION: Wherein X is A, S, Y, R, D, V or W

<400> SEQUENCE: 6

Gly Gly Gly Xaa
1

<210> SEQ ID NO 7
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Wherein residue S may be missing
<220> FEATURE:
<221> NAME/KEY: MISC_FEATURE
<222> LOCATION: (4)..(6)
<223> OTHER INFORMATION: Wherein any residues 4-6 may be missing

<400> SEQUENCE: 7

Ser Ser Ala Ala Ala Ala Ser Ser Ala Ala Ala Ala
1               5                   10

<210> SEQ ID NO 8
<211> LENGTH: 6
<212> TYPE: PRT
<213> ORGANISM: Galleria mellonella

<400> SEQUENCE: 8

Gly Leu Gly Gly Leu Gly
1               5

<210> SEQ ID NO 9
<211> LENGTH: 6
<212> TYPE: PRT
<213> ORGANISM: Artificial sequence
```

```
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Wherein X is L, I, V or P
<220> FEATURE:
<221> NAME/KEY: MISC_FEATURE
<222> LOCATION: (5)..(5)
<223> OTHER INFORMATION: Wherein X is L, I, V or P

<400> SEQUENCE: 9

Gly Xaa Gly Gly Xaa Gly
1               5

<210> SEQ ID NO 10
<211> LENGTH: 21
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (5)..(5)
<223> OTHER INFORMATION: Wherein X is Y, V, S or A
<220> FEATURE:
<221> NAME/KEY: MISC_FEATURE
<222> LOCATION: (6)..(20)
<223> OTHER INFORMATION: Wherein any of 6-20 may be missing
<220> FEATURE:
<221> NAME/KEY: MISC_FEATURE
<222> LOCATION: (10)..(10)
<223> OTHER INFORMATION: Wherein X is Y, V, S or A
<220> FEATURE:
<221> NAME/KEY: MISC_FEATURE
<222> LOCATION: (15)..(15)
<223> OTHER INFORMATION: Wherein X is Y, V, S or A
<220> FEATURE:
<221> NAME/KEY: MISC_FEATURE
<222> LOCATION: (20)..(20)
<223> OTHER INFORMATION: Wherein X is Y, V, S or A

<400> SEQUENCE: 10

Gly Pro Gly Gly Xaa Gly Pro Gly Gly Xaa Gly Pro Gly Gly Xaa Gly
1               5                   10                  15

Pro Gly Gly Xaa Tyr
            20

<210> SEQ ID NO 11
<211> LENGTH: 5
<212> TYPE: PRT
<213> ORGANISM: Argiope trifasciata

<400> SEQUENCE: 11

Gly Arg Gly Gly Ala
1               5

<210> SEQ ID NO 12
<211> LENGTH: 13
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (5)..(10)
<223> OTHER INFORMATION: Wherein any of 5-10 may be missing

<400> SEQUENCE: 12

Gly Ala Gly Ala Ala Ala Ala Ala Ala Ala Gly Gly Ala
1               5                   10
```

```
<210> SEQ ID NO 13
<211> LENGTH: 8
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (3)..(3)
<223> OTHER INFORMATION: Wherein X is Q, Y, L, A, S or R
<220> FEATURE:
<221> NAME/KEY: MISC_FEATURE
<222> LOCATION: (5)..(5)
<223> OTHER INFORMATION: Wherein X is Q, Y, L, A, S or R
<220> FEATURE:
<221> NAME/KEY: MISC_FEATURE
<222> LOCATION: (7)..(7)
<223> OTHER INFORMATION: Wherein X is Q, Y, L, A, S or R
<220> FEATURE:
<221> NAME/KEY: MISC_FEATURE
<222> LOCATION: (8)..(8)
<223> OTHER INFORMATION: Wherein X is Q, Y, L, A, S or R

<400> SEQUENCE: 13

Gly Gly Xaa Gly Xaa Gly Xaa Xaa
1               5

<210> SEQ ID NO 14
<211> LENGTH: 16
<212> TYPE: PRT
<213> ORGANISM: Bombyx mori

<400> SEQUENCE: 14

Thr Gly Ser Ser Gly Phe Gly Pro Tyr Val Asn Gly Gly Tyr Ser Gly
1               5                   10                  15

<210> SEQ ID NO 15
<211> LENGTH: 8
<212> TYPE: PRT
<213> ORGANISM: Bombyx mandarina

<400> SEQUENCE: 15

Tyr Glu Tyr Ala Trp Ser Ser Glu
1               5

<210> SEQ ID NO 16
<211> LENGTH: 7
<212> TYPE: PRT
<213> ORGANISM: Antheraea mylitta

<400> SEQUENCE: 16

Ser Asp Phe Gly Thr Gly Ser
1               5

<210> SEQ ID NO 17
<211> LENGTH: 7
<212> TYPE: PRT
<213> ORGANISM: Antheraea yamamai

<400> SEQUENCE: 17

Arg Arg Ala Gly Tyr Asp Arg
1               5

<210> SEQ ID NO 18
<211> LENGTH: 8
<212> TYPE: PRT
<213> ORGANISM: Galleria mellonella
```

```
<400> SEQUENCE: 18

Glu Val Ile Val Ile Asp Asp Arg
1               5

<210> SEQ ID NO 19
<211> LENGTH: 18
<212> TYPE: PRT
<213> ORGANISM: Nephila madascariensis

<400> SEQUENCE: 19

Thr Thr Ile Ile Glu Asp Leu Asp Ile Thr Ile Asp Gly Ala Asp Gly
1               5                   10                  15

Pro Ile

<210> SEQ ID NO 20
<211> LENGTH: 8
<212> TYPE: PRT
<213> ORGANISM: Nephila clavipes

<400> SEQUENCE: 20

Thr Ile Ser Glu Glu Leu Thr Ile
1               5

<210> SEQ ID NO 21
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 21

Gly Ala Gly Ala Gly Ser
1               5

<210> SEQ ID NO 22
<211> LENGTH: 5
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (4)..(4)
<223> OTHER INFORMATION: Wherein X is any residue
<220> FEATURE:
<221> NAME/KEY: MISC_FEATURE
<222> LOCATION: (5)..(5)
<223> OTHER INFORMATION: Wherein X is any residue

<400> SEQUENCE: 22

Gly Pro Gly Xaa Xaa
1               5
```

PEPTIDE-BASED NANOFIBRILLAR MATERIALS

CROSS-REFERENCE TO RELATED APPLICATION

This patent application is a National Stage Entry of International Patent Application No. PCT/US2014/064696, filed on Nov. 7, 2014, which application claims priority to and the benefit of U.S. provisional patent application Ser. No. 61/902,145, filed on Nov. 8, 2013, the entire contents of each of which are herein incorporated by reference.

GOVERNMENT SUPPORT

This invention was made with government support under grant No.: R01 EY020856, awarded by the National Institutes of Health and a National Defense Science and Engineering Graduate (NDSEG) fellowship awarded by Department of Defense. The United States Government has certain rights in the invention.

BACKGROUND

An aerogel is a gel comprised of a microporous solid, in which the dispersed phase is a gas. Structurally, an aerogel is characterized by a monolithic internal structure, which is composed of a nano-scale network of pores and fused colloids. The pore structure of aerogels, as classified by the International Union of Pure and Applied Chemistry (IUPAC), includes three different types of pores: micropores (<2 nm in diameter), mesopores (2-50 nm in diameter), and macropores (>50 nm in diameter) with a majority of the pores falling in the mesopore range.

Typically, production of aerogels involves the sol-gel process. That is, aerogels are derived from a gel (e.g., hydrogel), in which the liquid component of the gel has been replaced with a gas (e.g., "air"), resulting in an ultra-light porous material with extremely low density and low thermal conductivity. To date, commercially available aerogels include microporous silica, carbon-based aerogels, and zeolites.

Current applications for aerogels include catalyzers, particle detectors, thermal insulators, and energy absorbers.

SUMMARY

Disclosed herein are nanofibrillar materials and methods for producing such materials.

Among other things, the present disclosure provides nanofibrillar materials made of amphiphilic polypeptides. In some embodiments, nanofibrillar materials are characterized by certain properties that render these materials distinctive when compared with traditional aerogels or biopolymer films or biopolymer blocks that are either treated with methanol and/or formed with hexafluoroisopropanol (HFIP). In particular, nanofibrillar materials of the present disclosure are highly porous while displaying highly desirable nanofiber morphology. Indeed, nanofibrillar materials of the present disclosure possess a network of nano-scale fibers that are ultra-light having a pore structure matching and an average bulk density near that of traditional aerogels.

In some embodiments, nanofibrillar materials of the present disclosure are characterized by unique properties. In some embodiments, nanofibrillar materials provide low bulk density. In some embodiments, nanofibrillar materials of the present disclosure provide optically transparency in the visible spectrum. In some embodiments, nanofibrillar materials as provided herein are characterized in that they are non-toxic, so that they are capable of incorporating functional moieties (e.g. cells and/or enzymes). In some embodiments, nanofibrillar materials as provided herein are mechanically robust and possess a desirable compressive modulus. In some embodiments, nanofibrillar materials of the present disclosure possess mechanical properties that are tunable according to methods of the present disclosure. In some embodiments, highly crystalline nanofibrillar materials as disclosed herein are formed by a critical point drying of transparent hydrogels with a supercritical fluid, such as $CO_2$.

Implementations of the present disclosure can be valuably employed and are useful for a wide range of applications including, for example: biomedical, biomaterials, bionanotechnology, biosensing, electronic, functional biomaterials, functional fibers (e.g. nanowires, scaffolds, etc.), gas sensing, optics, optogenetics, photonic devices, tissue engineering applications, optics, photonics, and/or electronics.

In some embodiments, nanofibrillar materials of the present disclosure are made of or comprise polypeptides. In some embodiments, a polypeptide is from a single source, for example naturally occurring proteins. In some embodiments, polypeptides may be produced from various sources, including a regenerated protein from natural sources, such as purified protein. In some embodiments, polypeptides were produced from recombinant proteins. In some embodiments, recombinant proteins were produced from heterologous systems, were synthetically produced, were chemically produced, or combinations thereof.

In some embodiments, polypeptides useful in forming nanofibrillar materials as disclosed herein, for example, include: agarose, alginate, cellulose, chitin, chitosan, collagen, elastin, gelatin, hyaluronic acid, polydimethylsiloxane, poly(ethylene glycol), polyhydroxyalkanoates, poly(lactide-co-glycolide), pullan, resilin, silk, starch, or combinations thereof.

In some embodiments, nanofibrillar materials of the present disclosure comprise silk polypeptides.

In some embodiments, nanofibrillar materials are made of polypeptides corresponding to any one of the list provided above, with or without one or more sequence variations, as compared to the native or wild type counterpart. In some embodiments, for example, such variants may show at least 85% overall sequence identity as compared to a wild type sequence. In some embodiments, for example, such variants may show at least 86%, 87%, 88%, 89%, 90%, 91%, 92%, 93%, 94%, 95%, 96%, 97%, 98%, 99% overall sequence identity.

In some embodiments, nanofibrillar materials of the present disclosure are or comprise polypeptides having an amino acid sequence, for example, including at least one of selected from the following list: fibroins, actins, collagens, catenins, claudins, coilins, elastins, elaunins, extensins, fibrillins, lamins, laminins, keratins, tublins, viral structural proteins, zein proteins (seed storage protein), or combinations thereof.

In some embodiments, nanofibrillar materials as described herein may comprise silk fibroin polypeptides. In some embodiments, nanofibrillar materials as described herein consists essentially of silk fibroin polypeptides. In some embodiments, silk fibroin polypeptides are or comprise *Bombyx mori* fibroin.

In some embodiments, the present disclosure is based at least in part on a recognition that polypeptides with amphiphilic properties are particularly suited for generating nanofibrillar materials as provided herein.

In some embodiments, amphiphilic polypeptides have favorable physiochemical properties. In some embodiments, amphiphilic polypeptides are particularly suitable for generating nanofibrillar materials as provided herein due to their nature of having both hydrophilic and hydrophobic portions contained therein. In some embodiments, amphiphilic polypeptides may include both a hydrophobic module or stretch and a hydrophilic module or stretch within a single polypeptide, such that the single polypeptide itself is naturally amphiphilic. In some embodiments, amphiphilic polypeptides may include a hydrophobic module or stretch and a hydrophilic module or stretch and may be fused or coupled together to form an amphiphilic entity. Such "fusion" or "chimeric" polypeptides may be produced using recombinant techniques, chemical coupling, or combinations thereof.

In some embodiments, amphiphilic polypeptides suitable for the present disclosure are selected. In some embodiments, amphiphilic polypeptides are selected on a basis of an ability to form a micellar structure (i.e., micelles) in a solution. In some embodiments, amphiphilic polypeptides suitable for making nanofibrillar materials are disclosed herein are capable of self-assembling into nano-sized micelles having an average diameters typically between about 2 nm and about 100 nm.

In some embodiments, amphiphilic polypeptides may include a portion or portions of an amino acid sequence that adopt beta-sheet (β-sheet) secondary structure. In some embodiments, β-sheet secondary structure is particularly useful when forming nanofibrillar materials of the present disclosure. In some embodiments, amphiphilic polypeptides are selected on a basis of having a β-sheet secondary structure. In some embodiments, amphiphilic polypeptides are selected on a basis of having a propensity for forming a β-sheet secondary structure based a presence of such an amino acid sequence. In some embodiments, nanofibrillar materials as described herein may comprise an amphiphilic polypeptide containing an amino acid sequence motif GAGAGS (SEQ ID NO:21). In some embodiments, such an amphiphilic polypeptide may contain multiple copies (repeats) of such a motif.

In some embodiments, nanofibrillar materials are or comprise amphiphilic polypeptides having an average molecular weight between about 5 kDa and about 400 kDa. In some embodiments, nanofibrillar materials are or comprise amphiphilic polypeptides having a low average molecular weight. In some embodiments, nanofibrillar materials that are or comprise amphiphilic polypeptide having a low average molecular weight comprise amphiphilic polypeptides having an average molecular weight between about 5 kDa and about 125 kDa.

In some embodiments, nanofibrillar materials made of amphiphilic polypeptides as provided herein display desirable morphology, features, and properties.

In some embodiments, amphiphilic polypeptides show a fibrillar morphology. In some embodiments, amphiphilic polypeptides having a fibrillar morphology comprise a network of nano-sized fibers, nanofibrils. In some embodiments, the present disclosure appreciates that a formation of micellar nanostructures and β-sheet secondary structure from amphiphilic polypeptides contributes to generating nanofibrillar materials as disclosed herein.

In some embodiments, nanofibrils are formed from fused nanoparticles (e.g., micelles) of amphiphilic polypeptides.

In some embodiments, nanofibrillar materials are or comprise nanofibrils that are substantially uniformly distributed within a three-dimensional space. In some embodiments, nanofibrillar materials are monolithic networks of nanofibrils.

In some embodiments, nanofibrils of such nanofibrillar materials have an average diameter between about 2 nm and about 100 nm.

In some embodiments, nanofibrillar materials are or comprise nanofibrils that are porous. In some embodiments, nanofibrillar materials show porosity of at least 0.8, but typically at least 0.9. In some embodiments, nanofibrillar materials of the present disclosure are at least about 90% porous.

In some embodiments, nanofibrillar materials as described herein are highly porous, with nano-sized pores. In some embodiments, nanofibrillar materials include a network of interconnected pores.

In some embodiments, pores observed in nanofibrillar materials of the present disclosure are nano-sized pores. In some embodiments, an average pore diameter is between about 2 nm and 100 nm in diameter. In some embodiments, a majority of pores have a diameter between about 2 nm and about 100 nm.

In some embodiments, nanofibrils that form nanofibrillar materials as disclosed herein are or comprise amphiphilic polypeptides, although additional components may be incorporated to form such nanofibrils.

In some embodiments, nanofibrillar materials of the present disclosure exhibit desirable material properties. In some embodiments, nanofibrillar materials display properties, for example, including: low density; desirable compressive modulus, optical transparency, biocompatibility, or combinations thereof.

In some embodiments, nanofibrillar materials have low bulk density. In some embodiments, nanofibrillar materials have a bulk density that is less than 75 kg/m$^3$, e.g., less than 70 kg/m$^3$, less than 65 kg/m$^3$, less than 60 kg/m$^3$, less than 55 kg/m$^3$, less than 50 kg/m$^3$, less than 45 kg/m$^3$, less than 40 kg/m$^3$, less than 35 kg/m$^3$, less than 30 kg/m$^3$, less than 25 kg/m$^3$, less than 20 kg/m$^3$, less than 15 kg/m$^3$, less than 10 kg/m$^3$.

In some embodiments, nanofibrillar materials exhibit a desirable compressive modulus. In some embodiments, nanofibrillar materials of the present disclosure display a desirable compressive modulus such that when being compressed, nanofibrillar materials recover without showing a high degree of deformation. In some embodiments, nanofibrillar materials of the present disclosure exhibit a compressive modulus of between about 50 kPa and about 300 kPa.

In some embodiments, nanofibrillar materials of the present disclosure are optically transparent. In some embodiments, nanofibrillar materials allow up to about 99% transmittance of light. In some embodiments, nanofibrillar materials allow transmittance of light for light having various wavelengths. In some embodiments, nanofibrillar materials allow up to about 99% transmittance of light for wavelengths, for example, between about 390 nm and about 880 nm. In some embodiments, optical transparency is dependent on a thickness of a nanofibrillar material being measured. In some embodiments, optical transparency is measured for nanofibrillar materials have a thickness between about 0.5 mm and about 10 mm.

In some embodiments, nanofibrillar materials are characterized by an optical transparency of between about 50% and about 75% at about 600 nm.

In some embodiments, nanofibrillar materials of the present disclosure are characterized in that they are biocompatible. In some embodiments, nanofibrillar materials are non-toxic. In some embodiments, nanofibrillar materials permit incorporation of biologics. In some embodiments, nanofibrillar materials permit incorporation of functional moieties. In some embodiments, nanofibrillar materials incorporate enzymes. In some embodiments, nanofibrillar materials incorporate cells. In some embodiments, nanofibrillar materials incorporate moieties for other functions, such oxygen sensing, for example, including platinum(II) meso-tetrakis (pentafluorophenyl)porphyrin (PtTFPP).

In some embodiments, nanofibrillar materials of the present disclosure are provided, prepared, and/or manufactured from amphiphilic polypeptides. In some embodiments, amphiphilic polypeptides, for example, are or comprise: agarose, alginate, cellulose, chitin, chitosan, collagen, elastin, gelatin, hyaluronic acid, polydimethylsiloxane, poly (ethylene glycol), polyhydroxyalkanoates, poly(lactide-co-glycolide), pullan, resilin, silk, starch, or combinations thereof. In some embodiments, nanofibrillar materials of the present disclosure are provided, prepared, and/or manufactured from amphiphilic polypeptides having an amino acid sequence, for example, including at least one of selected from the following list: fibroins, actins, collagens, catenins, claudins, coilins, elastins, elaunins, extensins, fibrillins, lamins, laminins, keratins, tublins, viral structural proteins, zein proteins (seed storage protein), or combinations thereof.

In some embodiments, nanofibrillar materials of the present disclosure are provided, prepared, and/or manufactured from silk fibroin polypeptides. In some embodiments, nanofibrillar materials of the present disclosure are provided, prepared, and/or manufactured from essentially only silk fibroin polypeptides. In some embodiments, nanofibrillar materials of the present disclosure are provided, prepared, and/or manufactured from *Bombyx mori* fibroin.

In some embodiments, nanofibrillar materials of the present disclosure are provided, prepared, and/or manufactured from amphiphilic polypeptides having an average molecular weight in the range of between about 5 kDa and about 400 kDa. In some embodiments, nanofibrillar materials of the present disclosure are provided, prepared, and/or manufactured from amphiphilic polypeptides having a low average molecular weight. In some embodiments, nanofibrillar materials of the present disclosure are provided, prepared, and/or manufactured from amphiphilic polypeptides having an average molecular weight between about 5 kDa and about 125 kDa.

In some embodiments, methods of providing, preparing, and/or manufacturing nanofibrillar materials include providing an amphiphilic polypeptide hydrogel. In some embodiments, methods of providing, preparing, and/or manufacturing nanofibrillar materials include dehydrating an amphiphilic polypeptide hydrogel using an organic solvent. In some embodiments, methods of providing, preparing, and/or manufacturing nanofibrillar materials include supercritical drying of a dehydrated hydrogel to form a nanofibrillar material.

In some embodiments, methods of providing, preparing, and/or manufacturing nanofibrillar materials including providing an amphiphilic polypeptide hydrogel, includes a step of soaking an amphiphilic polypeptide hydrogel in EDTA to increase hydrogel stiffness.

In some embodiments, methods of providing, preparing, and/or manufacturing nanofibrillar materials including providing an amphiphilic polypeptide hydrogel, include a step of providing a solution of an amphiphilic polypeptide.

In some embodiments, methods of providing, preparing, and/or manufacturing nanofibrillar materials including providing a solution of an amphiphilic polypeptide, an amphiphilic polypeptide is silk fibroin.

In some embodiments, methods of providing, preparing, and/or manufacturing nanofibrillar materials including providing a solution of an amphiphilic polypeptide, an amphiphilic polypeptide is or comprises fused nano-sized micelles. In some embodiments, methods of providing, preparing, and/or manufacturing nanofibrillar materials including providing a solution of an amphiphilic polypeptide, an amphiphilic polypeptide is or comprises colloidal nanoparticles comprising an aggregate of the micelles. In some embodiments, methods of providing, preparing, and/or manufacturing nanofibrillar materials including providing a solution of an amphiphilic polypeptide, an amphiphilic polypeptide is or comprises micelles that are amorphous micelles, helically structured micelles, or combination thereof.

In some embodiments, methods of providing, preparing, and/or manufacturing nanofibrillar materials including providing a solution of an amphiphilic polypeptide, includes steps of introducing acetone to the solution, and evaporating acetone to induce hydrogel formation.

In some embodiments, methods of providing, preparing, and/or manufacturing nanofibrillar materials including providing a solution of an amphiphilic polypeptide, a solution of an amphiphilic polypeptide is between about 0.01% wt/vol and about 20.0% wt/vol.

In some embodiments, methods of providing, preparing, and/or manufacturing nanofibrillar materials including providing a solution of an amphiphilic polypeptide, includes steps of introducing a functional moiety into a solution of an amphiphilic polypeptide.

In some embodiments, methods of providing, preparing, and/or manufacturing nanofibrillar materials including introducing a functional moiety into a solution of an amphiphilic polypeptide, a functional moiety includes an enzyme. In some embodiments, methods of providing, preparing, and/or manufacturing nanofibrillar materials including introducing a functional moiety into a solution of an amphiphilic polypeptide, a functional moiety includes a cell.

In some embodiments, methods of providing, preparing, and/or manufacturing nanofibrillar materials including dehydrating an amphiphilic polypeptide hydrogel using an organic solvent, an organic solvent is or comprises methanol, ethanol, acetone, isopropanol, a halogenated derivative thereof (F, Cl, Br or I), or combinations thereof.

In some embodiments, methods of providing, preparing, and/or manufacturing nanofibrillar materials including dehydrating an amphiphilic polypeptide hydrogel using an organic solvent, includes a step of providing a solution of about 100% ethanol mixed with platinum(II) meso-tetrakis (pentafluorophenyl)porphyrin (PtTFPP) for improved oxygen sensing.

In some embodiments, methods of providing, preparing, and/or manufacturing nanofibrillar materials including supercritical drying of a dehydrated hydrogel to form a nanofibrillar material include steps of providing a supercritical fluid and applying a pressure of between about 1000 psi and about 5000 psi. In some embodiments, methods of providing, preparing, and/or manufacturing nanofibrillar materials including providing a supercritical fluid, a supercritical fluid, for example, is or comprises carbon dioxide, ammonia, ethylene, ethane, fluoroform, nitrous oxide, propane, freon or xenon.

In some embodiments, methods of providing, preparing, and/or manufacturing nanofibrillar materials including providing a supercritical fluid, a supercritical fluid, for example, is or comprises carbon dioxide.

In some embodiments, methods of providing, preparing, and/or manufacturing nanofibrillar materials including applying a pressure, include applying a pressure between about 1200 psi and about 1800 psi.

In some embodiments, matching, tuning, adjusting, and/or manipulating mechanical properties of a nanofibrillar materials of the present disclosure is accomplished, at least in part, by selecting a molecular weight of an amphiphilic polypeptide. In some embodiments, a molecular weight of an amphiphilic polypeptide is in a range of average molecular weights between about 5 kDa and about 400 kDa.

In some embodiments, matching, tuning, adjusting, and/or manipulating mechanical properties of a nanofibrillar materials of the present disclosure is accomplished, at least in part, by selecting an amphiphilic polypeptide solution concentration. In some embodiments, a polymer solution concentration is in a range of concentrations between about 0.01% wt/vol and about 20.0% wt/vol.

BRIEF DESCRIPTION OF THE DRAWING

The foregoing and other objects, aspects, features, and advantages of the present disclosure will become more apparent and better understood by referring to the following description taken in conjunction with the accompanying figures in which:

FIG. 1f shows a scanning electron microscope of a sample with initial concentration of 20 mg/ml.

DEFINITIONS

Figure 1:
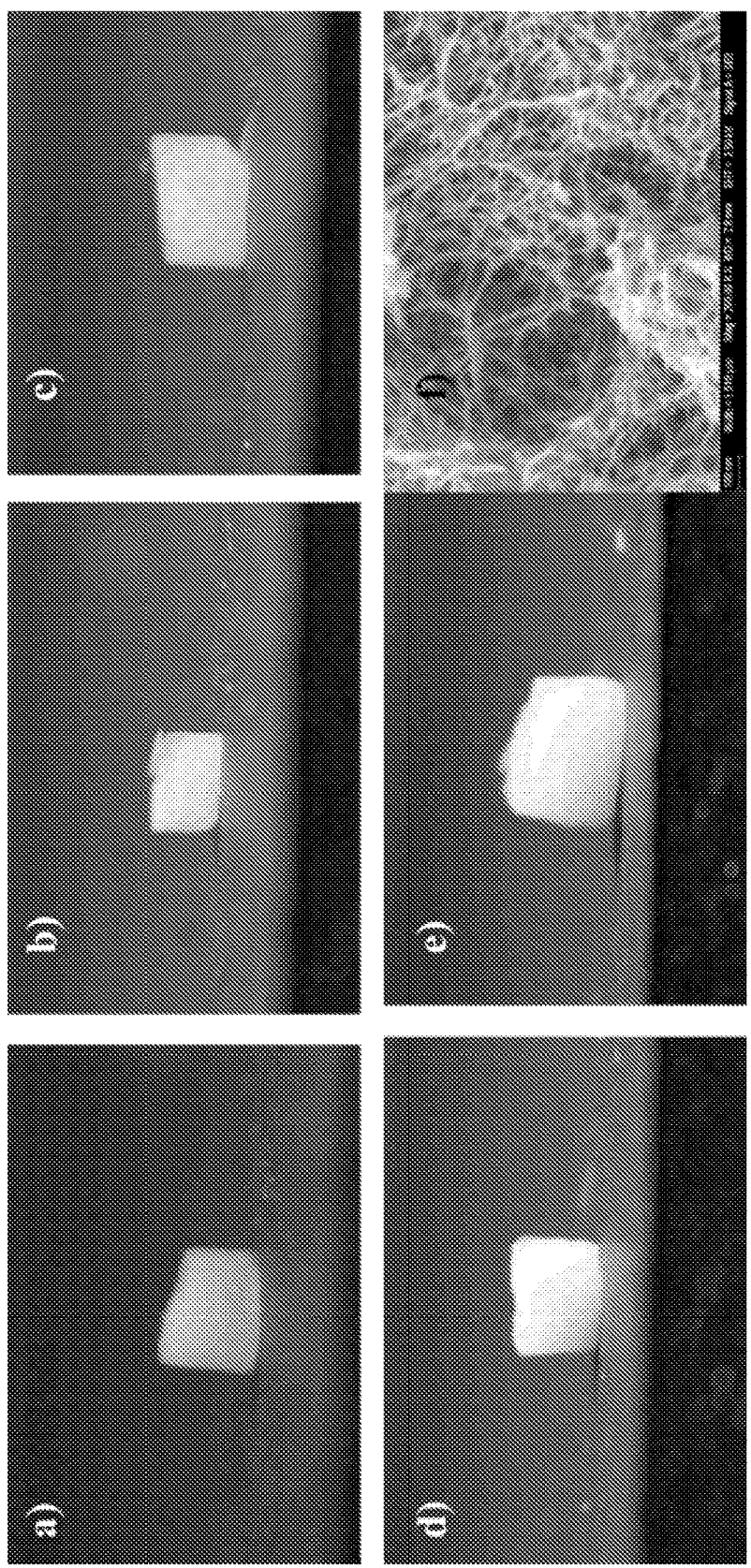
FIG. 1. shows macroscale images of varying concentrations of silk nanofibrillar material. Initial silk concentrations of 7.5 mg/ml, 10 mg/ml, 15 mg/ml, 20 mg/ml, and 30 mg/ml are shown for FIG. 1a-FIG. 1e respectively.

In order for the present disclosure to be more readily understood, certain terms are first defined below. Additional definitions for the following terms and other terms are set forth throughout the specification.

In this application, unless otherwise clear from context, the term "a" may be understood to mean "at least one." As used in this application, the term "or" may be understood to mean "and/or." In this application, the terms "comprising" and "including" may be understood to encompass itemized components or steps whether presented by themselves or together with one or more additional components or steps. Unless otherwise stated, the terms "about" and "approximately" may be understood to permit standard variation as would be understood by those of ordinary skill in the art. Where ranges are provided herein, the endpoints are included. As used in this application, the term "comprise" and variations of the term, such as "comprising" and "comprises," are not intended to exclude other additives, components, integers or steps.

As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Administration": As used herein, the term "administration" refers to the administration of a composition to a subject. Administration may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal and vitreal.

"Affinity": As is known in the art, "affinity" is a measure of the tightness with a particular ligand binds to its partner. Affinities can be measured in different ways. In some embodiments, affinity is measured by a quantitative assay. In some such embodiments, binding partner concentration may be fixed to be in excess of ligand concentration so as to mimic physiological conditions. Alternatively or additionally, in some embodiments, binding partner concentration and/or ligand concentration may be varied. In some such embodiments, affinity may be compared to a reference under comparable conditions (e.g., concentrations).

"Agent": As used herein, the term "agent" may refer to a compound or entity of any chemical class including, for example, polypeptides, nucleic acids, saccharides, lipids, small molecules, metals, or combinations thereof. As will be clear from context, in some embodiments, an agent can be or comprise a cell or organism, or a fraction, extract, or component thereof. In some embodiments, an agent is agent is or comprises a natural product in that it is found in and/or is obtained from nature. In some embodiments, an agent is or comprises one or more entities that is man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents are provided as collections or libraries, for example that may be screened to identify or characterize active agents within them. Some particular embodiments of agents that may be utilized in accordance with the present disclosure include small molecules, antibodies, antibody fragments, aptamers, siRNAs, shRNAs, DNA/RNA hybrids, antisense oligonucleotides, ribozymes, peptides, peptide mimetics, small molecules, etc. In some embodiments, an agent is or comprises a polymer. In some embodiments, an agent is not a polymer and/or is substantially free of any polymer. In some embodiments, an agent contains at least one polymeric moiety. In some embodiments, an agent lacks or is substantially free of any polymeric moiety.

"Amphiphilic": As used herein, the term "analog" refers to a chemical compound which has both hydrophobic and hydrophilic groups and possessing both hydrophilic and hydrophobic properties. Such a compound is called amphiphilic or amphipathic and these terms are used interchangeably.

"Analog": As used herein, the term "analog" refers to a substance that shares one or more particular structural features, elements, components, or moieties with a reference substance. Typically, an "analog" shows significant structural similarity with the reference substance, for example sharing a core or consensus structure, but also differs in certain discrete ways. In some embodiments, an analog is a substance that can be generated from the reference substance by chemical manipulation of the reference substance. In some embodiments, an analog is a substance that can be generated through performance of a synthetic process substantially similar to (e.g., sharing a plurality of steps with) one that generates the reference substance. In some embodiments, an analog is or can be generated through performance of a synthetic process different from that used to generate the reference substance.

"Amino acid": As used herein, the term "amino acid," in its broadest sense, refers to any compound and/or substance that can be incorporated into a polypeptide chain, e.g., through formation of one or more peptide bonds. In some embodiments, an amino acid has the general structure H2N—C(H)(R)—COOH. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. In some embodiments, an amino acid, including a carboxy- and/or amino-terminal amino acid in a polypeptide, can contain a structural modification as compared with the general structure above. For example, in some embodiments, an amino acid may be modified by methylation, amidation, acetylation, and/or substitution as compared with the general structure. In some embodiments, such modification may, for example, alter the circulating half-life of a polypeptide containing the modified amino acid as compared with one containing an otherwise identical unmodified amino acid. In some embodiments, such modification does not significantly alter a relevant activity of a polypeptide containing the modified amino acid, as compared with one containing an otherwise identical unmodified amino acid. As will be clear from context, in some embodiments, the term "amino acid" is used to refer to a free amino acid; in some embodiments it is used to refer to an amino acid residue of a polypeptide.

"Antibody": As used herein, the term "antibody" refers to a polypeptide that includes canonical immunoglobulin sequence elements sufficient to confer specific binding to a particular target antigen. As is known in the art, intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)—an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. Amino acid sequence comparisons among antibody polypeptide chains have defined two light chain (κ and λ) classes, several heavy chain (e.g., μ, γ, α, ε, δ) classes, and certain heavy chain subclasses (α1, α2, γ1, γ2, γ3, and γ4). Antibody classes (IgA [including IgA1, IgA2], IgD, IgE, IgG [including IgG1, IgG2, IgG3, IgG4], IgM) are defined based on the class of the utilized heavy chain sequences. For purposes of the present disclosure, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is monoclonal; in some embodiments, an antibody is monoclonal. In some embodiments, an antibody has constant region sequences that are characteristic of mouse, rabbit, primate, or human antibodies. In some embodiments, an antibody sequence elements are humanized, primatized, chimeric, etc., as is known in the art. Moreover, the term "antibody" as used herein, will be understood to encompass (unless otherwise stated or clear from context) can refer in appropriate embodiments to any of the art-known or developed constructs or formats for capturing antibody structural and functional features in alternative presentation. For example, in some embodiments, the term can refer to bi- or other multi-specific (e.g., zybodies, etc.) antibodies, Small Modular ImmunoPharmaceuticals ("SMIPs™"), single chain antibodies, cameloid antibodies, and/or antibody fragments. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc], or other pendant group [e.g., poly-ethylene glycol, etc]

"Associated": As used herein, the term "associated" typically refers to two or more entities in physical proximity with one another, either directly or indirectly (e.g., via one or more additional entities that serve as a linking agent), to form a structure that is sufficiently stable so that the entities remain in physical proximity under relevant conditions, e.g., physiological conditions. In some embodiments, associated entities are covalently linked to one another. In some embodiments, associated entities are non-covalently linked. In some embodiments, associated entities are linked to one another by specific non-covalent interactions (i.e., by interactions between interacting ligands that discriminate between their interaction partner and other entities present in the context of use, such as, for example. streptavidin/avidin interactions, antibody/antigen interactions, etc.). Alternatively or additionally, a sufficient number of weaker non-covalent interactions can provide sufficient stability for moieties to remain associated. Exemplary non-covalent interactions include, but are not limited to, affinity interactions, metal coordination, physical adsorption, host-guest interactions, hydrophobic interactions, pi stacking interactions, hydrogen bonding interactions, van der Waals interactions, magnetic interactions, electrostatic interactions, dipole-dipole interactions, etc.

"Binding": It will be understood that the term "binding", as used herein, typically refers to a non-covalent association between or among two or more entities. "Direct" binding involves physical contact between entities or moieties; indirect binding involves physical interaction by way of physical contact with one or more intermediate entities. Binding between two or more entities can typically be assessed in any of a variety of contexts—including where interacting entities or moieties are studied in isolation or in the context of more complex systems (e.g., while covalently or otherwise associated with a carrier entity and/or in a biological system or cell).

"Binding agent": In general, the term "binding agent" is used herein to refer to any entity that binds to a target of interest as described herein. In many embodiments, a binding agent of interest is one that binds specifically with its target in that it discriminates its target from other potential binding partners in a particular interaction contact. In general, a binding agent may be or comprise an entity of any chemical class (e.g., polymer, non-polymer, small molecule, polypeptide, carbohydrate, lipid, nucleic acid, etc). In some embodiments, a binding agent is a single chemical entity. In some embodiments, a binding agent is a complex of two or more discrete chemical entities associated with one another under relevant conditions by non-covalent interactions. For example, those skilled in the art will appreciate that in some embodiments, a binding agent may comprise a "generic" binding moiety (e.g., one of biotin/avidin/streptaviding and/or a class-specific antibody) and a "specific" binding moiety (e.g., an antibody or aptamers with a particular molecular target) that is linked to the partner of the generic biding moiety. In some embodiments, such an approach can permit modular assembly of multiple binding agents through linkage of different specific binding moieties with the same generic binding poiety partner. In some embodiments, binding agents are or comprise polypeptides (including, e.g., antibodies or antibody fragments). In some embodiments, binding agents are or comprise small molecules. In some embodiments, binding agents are or comprise nucleic acids. In some embodiments, binding agents are aptamers. In some embodiments, binding agents are polymers; in some embodiments, binding agents are not polymers. In some embodiments, binding agents are non-polymeric in that they lack polymeric moieties. In some embodiments, binding agents are or comprise carbohydrates. In some embodiments, binding agents are or comprise lectins. In some embodiments, binding agents are or comprise peptidomimetics. In some embodiments, binding agents are or comprise scaffold proteins. In some embodiments, binding agents are or comprise mimeotopes. In some embodiments, binding agents are or comprise stapled peptides. In certain embodiments, binding agents are or comprise nucleic acids, such as DNA or RNA.

"Biocompatible": The term "biocompatible", as used herein, refers to materials that do not cause significant harm to living tissue when placed in contact with such tissue, e.g., in vivo. In certain embodiments, materials are "biocompatible" if they are not toxic to cells. In certain embodiments, materials are "biocompatible" if their addition to cells in vitro results in less than or equal to 20% cell death, and/or their administration in vivo does not induce significant inflammation or other such adverse effects.

"Biodegradable": As used herein, the term "biodegradable" refers to materials that, when introduced into cells, are broken down (e.g., by cellular machinery, such as by enzymatic degradation, by hydrolysis, and/or by combinations thereof) into components that cells can either reuse or dispose of without significant toxic effects on the cells. In certain embodiments, components generated by breakdown of a biodegradable material are biocompatible and therefore do not induce significant inflammation and/or other adverse effects in vivo. In some embodiments, biodegradable polymer materials break down into their component monomers. In some embodiments, breakdown of biodegradable materials (including, for example, biodegradable polymer materials) involves hydrolysis of ester bonds. Alternatively or additionally, in some embodiments, breakdown of biodegradable materials (including, for example, biodegradable polymer materials) involves cleavage of urethane linkages. Exemplary biodegradable polymers include, for example, polymers of hydroxy acids such as lactic acid and glycolic acid, including but not limited to poly(hydroxyl acids), poly(lactic acid)(PLA), poly(glycolic acid)(PGA), poly(lactic-co-glycolic acid)(PLGA), and copolymers with PEG, polyanhydrides, poly(ortho)esters, polyesters, polyurethanes, poly(butyric acid), poly(valeric acid), poly(caprolactone), poly(hydroxyalkanoates, poly(lactide-co-caprolactone), blends and copolymers thereof. Many naturally occurring polymers are also biodegradable, including, for example, proteins such as albumin, collagen, gelatin and prolamines, for example, zein, and polysaccharides such as alginate, cellulose derivatives and polyhydroxyalkanoates, for example, polyhydroxybutyrate blends and copolymers thereof. Those of ordinary skill in the art will appreciate or be able to determine when such polymers are biocompatible and/or biodegradable derivatives thereof (e.g., related to a parent polymer by substantially identical structure that differs only in substitution or addition of particular chemical groups as is known in the art).

"Biologically active": As used herein, the phrase "biologically active" refers to a substance that has activity in a biological system (e.g., in a cell (e.g., isolated, in culture, in a tissue, in an organism), in a cell culture, in a tissue, in an organism, etc.). For instance, a substance that, when administered to an organism, has a biological effect on that organism, is considered to be biologically active. It will be appreciated by those skilled in the art that often only a portion or fragment of a biologically active substance is required (e.g., is necessary and sufficient) for the activity to be present; in such circumstances, that portion or fragment is considered to be a "biologically active" portion or fragment.

"Characteristic portion": As used herein, the term "characteristic portion" is used, in the broadest sense, to refer to a portion of a substance whose presence (or absence) correlates with presence (or absence) of a particular feature, attribute, or activity of the substance. In some embodiments, a characteristic portion of a substance is a portion that is found in the substance and in related substances that share the particular feature, attribute or activity, but not in those that do not share the particular feature, attribute or activity. In certain embodiments, a characteristic portion shares at least one functional characteristic with the intact substance. For example, in some embodiments, a "characteristic portion" of a protein or polypeptide is one that contains a continuous stretch of amino acids, or a collection of continuous stretches of amino acids, that together are characteristic of a protein or polypeptide. In some embodiments, each such continuous stretch generally contains at least 2, 5, 10, 15, 20, 50, or more amino acids. In general, a characteristic portion of a substance (e.g., of a protein, antibody, etc.) is one that, in addition to the sequence and/or structural identity specified above, shares at least one functional characteristic with the relevant intact substance. In some embodiments, a characteristic portion may be biologically active.

"Comparable": The term "comparable", as used herein, refers to two or more agents, entities, situations, sets of conditions, etc. that may not be identical to one another but that are sufficiently similar to permit comparison therebetween so that conclusions may reasonably be drawn based on differences or similarities observed. Those of ordinary skill in the art will understand, in context, what degree of identity is required in any given circumstance for two or more such agents, entities, situations, sets of conditions, etc. to be considered comparable.

"Conjugated": As used herein, the terms "conjugated," "linked," "attached," and "associated with," when used with respect to two or more moieties, means that the moieties are physically associated or connected with one another, either directly or via one or more additional moieties that serves as a linking agent, to form a structure that is sufficiently stable so that the moieties remain physically associated under the conditions in which structure is used, e.g., physiological conditions. Typically the moieties are attached either by one or more covalent bonds or by a mechanism that involves specific binding. Alternately, a sufficient number of weaker interactions can provide sufficient stability for moieties to remain physically associated.

"Corresponding to": As used herein, the term "corresponding to" is often used to designate the position/identity of a residue in a polymer, such as an amino acid residue in a polypeptide or a nucleotide residue in a nucleic acid. Those of ordinary skill will appreciate that, for purposes of simplicity, residues in such a polymer are often designated using a canonical numbering system based on a reference related polymer, so that a residue in a first polymer "corresponding to" a residue at position 190 in the reference polymer, for example, need not actually be the 190th residue in the first polymer but rather corresponds to the residue found at the 190th position in the reference polymer; those of ordinary skill in the art readily appreciate how to identify "corresponding" amino acids, including through use of one or more commercially-available algorithms specifically designed for polymer sequence comparisons.

"Detection entity": The term "detection entity" as used herein refers to any element, molecule, functional group, compound, fragment or moiety that is detectable. In some embodiments, a detection entity is provided or utilized alone. In some embodiments, a detection entity is provided and/or utilized in association with (e.g., joined to) another agent. Examples of detection entities include, but are not limited to: various ligands, radionuclides (e.g., $^{3}$H, $^{14}$C, $^{18}$F, $^{19}$F, $^{32}$P, $^{35}$S, $^{135}$I, $^{125}$I, $^{123}$I, $^{64}$Cu, $^{187}$Re, $^{111}$In, $^{90}$Y, $^{99m}$Tc, $^{177}$Lu, $^{89}$Zr etc.), fluorescent dyes (for specific exemplary fluorescent dyes, see below), chemiluminescent agents (such as, for example, acridinium esters, stabilized dioxetanes, and the like), bioluminescent agents, spectrally resolvable inorganic fluorescent semiconductors nanocrystals (i.e., quantum dots), metal nanoparticles (e.g., gold, silver, copper, platinum, etc.) nanoclusters, paramagnetic metal ions, enzymes (for specific examples of enzymes, see below), colorimetric labels (such as, for example, dyes, colloidal gold, and the like), biotin, dioxigenin, haptens, and proteins for which antisera or monoclonal antibodies are available.

"Determine": Many methodologies described herein include a step of "determining". Those of ordinary skill in the art, reading the present specification, will appreciate that such "determining" can utilize or be accomplished through use of any of a variety of techniques available to those skilled in the art, including for example specific techniques explicitly referred to herein. In some embodiments, determining involves manipulation of a physical sample. In some embodiments, determining involves consideration and/or manipulation of data or information, for example utilizing a computer or other processing unit adapted to perform a relevant analysis. In some embodiments, determining involves receiving relevant information and/or materials from a source. In some embodiments, determining involves comparing one or more features of a sample or entity to a comparable reference.

"Dosage form": As used herein, the term "dosage form" refers to a physically discrete unit of a therapeutic agent for administration to a subject. Each unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen).

"Encapsulated": The term "encapsulated" is used herein to refer to substances that are completely surrounded by another material.

"Functional": As used herein, a "functional" biological molecule is a biological molecule in a form in which it exhibits a property and/or activity by which it is characterized. A biological molecule may have two functions (i.e., bi-functional) or many functions (i.e., multifunctional).

"Graft rejection": The term "graft rejection" as used herein, refers to rejection of tissue transplanted from a donor individual to a recipient individual. In some embodiments, graft rejection refers to an allograft rejection, wherein the donor individual and recipient individual are of the same species. Typically, allograft rejection occurs when the donor tissue carries an alloantigen against which the recipient immune system mounts a rejection response.

"High Molecular Weight Polymer": As used herein, the term "high molecular weight polymer" refers to polymers and/or polymer solutions comprised of polymers (e.g., protein polymers, such as silk) having molecular weights of at least about 200 kDa, and wherein no more than 30% of the silk fibroin has a molecular weight of less than 100 kDa. In some embodiments, high molecular weight polymers and/or polymer solutions have an average molecular weight of at least about 100 kDa or more, including, e.g., at least about 150 kDa, at least about 200 kDa, at least about 250 kDa, at least about 300 kDa, at least about 350 kDa or more. In some embodiments, high molecular weight polymers have a molecular weight distribution, no more than 50%, for example, including, no more than 40%, no more than 30%, no more than 20%, no more than 10%, of the silk fibroin can have a molecular weight of less than 150 kDa, or less than 125 kDa, or less than 100 kDa.

"Hydrolytically degradable": As used herein, the term "hydrolytically degradable" is used to refer to materials that degrade by hydrolytic cleavage. In some embodiments, hydrolytically degradable materials degrade in water. In some embodiments, hydrolytically degradable materials degrade in water in the absence of any other agents or materials. In some embodiments, hydrolytically degradable materials degrade completely by hydrolytic cleavage, e.g., in water. By contrast, the term "non-hydrolytically degradable" typically refers to materials that do not fully degrade by hydrolytic cleavage and/or in the presence of water (e.g., in the sole presence of water).

"Hydrophilic": As used herein, the term "hydrophilic" and/or "polar" refers to a tendency to mix with, or dissolve easily in, water.

"Hydrophobic": As used herein, the term "hydrophobic" and/or "non-polar", refers to a tendency to repel, not combine with, or an inability to dissolve easily in, water.

"Identity": As used herein, the term "identity" refers to the overall relatedness between polymeric molecules, e.g., between nucleic acid molecules (e.g., DNA molecules and/or RNA molecules) and/or between polypeptide molecules. In some embodiments, polymeric molecules are considered to be "substantially identical" to one another if their sequences are at least 25%, 30%, 35%, 40%, 45%, 50%, 55%, 60%, 65%, 70%, 75%, 80%, 85%, 90%, 95%, or 99% identical. Calculation of the percent identity of two nucleic acid or polypeptide sequences, for example, can be performed by aligning the two sequences for optimal comparison purposes (e.g., gaps can be introduced in one or both of a first and a second sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of a reference sequence. The nucleotides at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4: 11-17), which has been incorporated into the ALIGN program (version 2.0). In some exemplary embodiments, nucleic acid sequence comparisons made with the ALIGN program use a PAM 120 weight residue table, a gap length penalty of 12 and a gap penalty of 4. The percent identity between two nucleotide sequences can, alternatively, be determined using the GAP program in the GCG software package using an NWSgap-dna.CMP matrix.

"Low Molecular Weight Polymer": As used herein, the term "low molecular weight polymer" refers to polymers and/or polymer solutions, such as silk, comprised of polymers (e.g., protein polymers) having molecular weights within the range of about 20 kDa-about 400 kDa. In some embodiments, low molecular weight polymers (e.g., protein polymers) have molecular weights within a range between a lower bound (e.g., about 20 kDa, about 30 kDa, about 40 kDa, about 50 kDa, about 60 kDa, or more) and an upper bound (e.g., about 400 kDa, about 375 kDa, about 350 kDa, about 325 kDa, about 300 kDa, or less). In some embodiments, low molecular weight polymers (e.g., protein polymers such as silk) are substantially free of, polymers having a molecular weight above about 400 kD. In some embodiments, the highest molecular weight polymers in provided nanofibrillar materials are less than about 300-about 400 kD (e.g., less than about 400 kD, less than about 375 kD, less than about 350 kD, less than about 325 kD, less than about 300 kD, etc). In some embodiments, a low molecular weight polymer and/or polymer solution can comprise a population of polymer fragments having a range of molecular weights, characterized in that: no more than 15% of the total moles of polymer fragments in the population has a molecular weight exceeding 200 kDa, and at least 50% of the total moles of the silk fibroin fragments in the population has a molecular weight within a specified range, wherein the specified range is between about 3.5 kDa and about 120 kDa or between about 5 kDa and about 125 kDa.

"Marker": A marker, as used herein, refers to an entity or moiety whose presence or level is a characteristic of a particular state or event. In some embodiments, presence or level of a particular marker may be characteristic of presence or stage of a disease, disorder, or condition. To give but one example, in some embodiments, the term refers to a gene expression product that is characteristic of a particular tumor, tumor subclass, stage of tumor, etc. Alternatively or additionally, in some embodiments, a presence or level of a particular marker correlates with activity (or activity level) of a particular signaling pathway, for example that may be characteristic of a particular class of tumors. The statistical significance of the presence or absence of a marker may vary depending upon the particular marker. In some embodiments, detection of a marker is highly specific in that it reflects a high probability that the tumor is of a particular subclass. Such specificity may come at the cost of sensitivity (i.e., a negative result may occur even if the tumor is a tumor that would be expected to express the marker). Conversely, markers with a high degree of sensitivity may be less specific that those with lower sensitivity. According to the present disclosure a useful marker need not distinguish tumors of a particular subclass with 100% accuracy.

"Modulator": The term "modulator" is used to refer to an entity whose presence or level in a system in which an activity of interest is observed correlates with a change in level and/or nature of that activity as compared with that observed under otherwise comparable conditions when the modulator is absent. In some embodiments, a modulator is an activator, in that activity is increased in its presence as compared with that observed under otherwise comparable conditions when the modulator is absent. In some embodiments, a modulator is an antagonist or inhibitor, in that activity is reduced in its presence as compared with otherwise comparable conditions when the modulator is absent. In some embodiments, a modulator interacts directly with a target entity whose activity is of interest. In some embodiments, a modulator interacts indirectly (i.e., directly with an intermediate agent that interacts with the target entity) with a target entity whose activity is of interest. In some embodiments, a modulator affects level of a target entity of interest; alternatively or additionally, in some embodiments, a modulator affects activity of a target entity of interest without affecting level of the target entity. In some embodiments, a modulator affects both level and activity of a target entity of interest, so that an observed difference in activity is not entirely explained by or commensurate with an observed difference in level.

"Nanoparticle": As used herein, the term "nanoparticle" refers to a particle having a diameter of less than 1000 nanometers (nm). In some embodiments, a nanoparticle has a diameter of less than 300 nm, as defined by the National Science Foundation. In some embodiments, a nanoparticle has a diameter of less than 100 nm as defined by the National Institutes of Health. In some embodiments, nanoparticles are micelles in that they comprise an enclosed compartment, separated from the bulk solution by a micellar membrane, typically comprised of amphiphilic entities which surround and enclose a space or compartment (e.g., to define a lumen). In some embodiments, a micellar membrane is comprised of at least one polymer, such as for example a biocompatible and/or biodegradable polymer.

"Nanoparticle composition": As used herein, the term "nanoparticle composition" refers to a composition that contains at least one nanoparticle and at least one additional agent or ingredient. In some embodiments, a nanoparticle composition contains a substantially uniform collection of nanoparticles as described herein.

"Nucleic acid": As used herein, the term "nucleic acid," in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. In some embodiments, "nucleic acid" refers to individual nucleic acid residues (e.g., nucleotides and/or nucleosides). In some embodiments, "nucleic acid" refers to an oligonucleotide chain comprising individual nucleic acid residues. As used herein, the terms "oligonucleotide" and "polynucleotide" can be used interchangeably. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e., analogs having other than a phosphodiester backbone. For example, the so-called "peptide nucleic acids," which are known in the art and have peptide bonds instead of phosphodiester bonds in the backbone, are considered within the scope of the present disclosure. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. The term "nucleic acid segment" is used herein to refer to a nucleic acid sequence that is a portion of a longer nucleic acid sequence. In many embodiments, a nucleic acid segment comprises at least 3, 4, 5, 6, 7, 8, 9, 10, or more residues. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present disclosure is specifically directed to "unmodified nucleic acids," meaning nucleic acids (e.g., polynucleotides and residues, including nucleotides and/or nucleosides) that have not been chemically modified in order to facilitate or achieve delivery.

"Pharmaceutical composition": As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

"Physiological conditions": The phrase "physiological conditions", as used herein, relates to the range of chemical (e.g., pH, ionic strength) and biochemical (e.g., enzyme concentrations) conditions likely to be encountered in the intracellular and extracellular fluids of tissues. For most tissues, the physiological pH ranges from about 6.8 to about 8.0 and a temperature range of about 20-40 degrees Celsius, about 25-40° C., about 30-40° C., about 35-40° C., about 37° C., atmospheric pressure of about 1. In some embodiments, physiological conditions utilize or include an aqueous environment (e.g., water, saline, Ringers solution, or other buffered solution); in some such embodiments, the aqueous environment is or comprises a phosphate buffered solution (e.g., phosphate-buffered saline).

"Polypeptide": The term "polypeptide" as used herein, refers to a string of at least three amino acids linked together by peptide bonds. In some embodiments, a polypeptide comprises naturally-occurring amino acids; alternatively or additionally, in some embodiments, a polypeptide comprises one or more non-natural amino acids (i.e., compounds that do not occur in nature but that can be incorporated into a polypeptide chain; see, for example, http://www.cco.caltech.edu/~dadgrp/Unnatstruct.gif, which displays structures of non-natural amino acids that have been successfully incorporated into functional ion channels) and/or amino acid analogs as are known in the art may alternatively be employed). For example, a polypeptide can be a protein. In some embodiments, one or more of the amino acids in a polypeptide may be modified, for example, by the addition of a chemical entity such as a carbohydrate group, a phosphate group, a farnesyl group, an isofarnesyl group, a fatty acid group, a linker for conjugation, functionalization, or other modification, etc.

"Polysaccharide": The term "polysaccharide" refers to a polymer of sugars. Typically, a polysaccharide comprises at least three sugars. In some embodiments, a polypeptide comprises natural sugars (e.g., glucose, fructose, galactose, mannose, arabinose, ribose, and xylose); alternatively or additionally, in some embodiments, a polypeptide comprises one or more non-natural amino acids (e.g. modified sugars such as 2'-fluororibose, 2'-deoxyribose, and hexose).

"Porosity": The term "porosity" as used herein, refers to a measure of void spaces in a material and is a fraction of volume of voids over the total volume, as a percentage between 0 and 100%. A determination of a porosity is known to a skilled artisan using standardized techniques, for example mercury porosimetry and gas adsorption (e.g., nitrogen adsorption).

"Protein": As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

"Reference": The term "reference" is often used herein to describe a standard or control agent, individual, population, sample, sequence or value against which an agent, individual, population, sample, sequence or value of interest is compared. In some embodiments, a reference agent, individual, population, sample, sequence or value is tested and/or determined substantially simultaneously with the testing or determination of the agent, individual, population, sample, sequence or value of interest. In some embodiments, a reference agent, individual, population, sample, sequence or value is a historical reference, optionally embodied in a tangible medium. Typically, as would be understood by those skilled in the art, a reference agent, individual, population, sample, sequence or value is determined or characterized under conditions comparable to those utilized to determine or characterize the agent, individual, population, sample, sequence or value of interest.

"Small molecule": As used herein, the term "small molecule" is used to refer to molecules, whether naturally-occurring or artificially created (e.g., via chemical synthesis), having a relatively low molecular weight and being an organic and/or inorganic compound. Typically, a "small molecule" is monomeric and have a molecular weight of less than about 1500 g/mol. In general, a "small molecule" is a molecule that is less than about 5 kilodaltons (kD) in size. In some embodiments, a small molecule is less than about 4 kD, 3 kD, about 2 kD, or about 1 kD. In some embodiments, the small molecule is less than about 800 daltons (D), about 600 D, about 500 D, about 400 D, about 300 D, about 200 D, or about 100 D. In some embodiments, a small molecule is less than about 2000 g/mol, less than about 1500 g/mol, less than about 1000 g/mol, less than about 800 g/mol, or less than about 500 g/mol. In some embodiments, a small molecule is not a polymer. In some embodiments, a small molecule does not include a polymeric moiety. In some embodiments, a small molecule is not a protein or polypeptide (e.g., is not an oligopeptide or peptide). In some embodiments, a small molecule is not a polynucleotide (e.g., is not an oligonucleotide). In some embodiments, a small molecule is not a polysaccharide. In some embodiments, a small molecule does not comprise a polysaccharide (e.g., is not a glycoprotein, proteoglycan, glycolipid, etc.). In some embodiments, a small molecule is not a lipid. In some embodiments, a small molecule is a modulating agent. In some embodiments, a small molecule is biologically active. In some embodiments, a small molecule is detectable (e.g., comprises at least one detectable moiety). In some embodiments, a small molecule is a therapeutic. Preferred small molecules are biologically active in that they produce a local or systemic effect in animals, preferably mammals, more preferably humans. In certain preferred embodiments, the small molecule is a drug. Preferably, though not necessarily, the drug is one that has already been deemed safe and effective for use by the appropriate governmental agency or body. For example, drugs for human use listed by the FDA under 21 C.F.R. §§ 330.5, 331 through 361, and 440 through 460; drugs for veterinary use listed by the FDA under 21 C.F.R. §§ 500 through 589, incorporated herein by reference, are all considered acceptable for use in accordance with the present application.

"Solution": As used herein, the term "solution" broadly refers to a homogeneous mixture composed of one phase. Typically, a solution comprises a solute or solutes dissolved in a solvent or solvents. It is characterized in that the properties of the mixture (such as concentration, temperature, and density) can be uniformly distributed through the volume. In the context of the present application, therefore, a "silk fibroin solution" refers to silk fibroin protein in a soluble form, dissolved in a solvent, such as water. In some embodiments, silk fibroin solutions may be prepared from a solid-state silk fibroin material (i.e., silk matrices), such as silk films and other scaffolds. Typically, a solid-state silk fibroin material is reconstituted with an aqueous solution, such as water and a buffer, into a silk fibroin solution. It should be noted that liquid mixtures that are not homogeneous, e.g., colloids, suspensions, emulsions, are not considered solutions.

"Stable": The term "stable," when applied to compositions herein, means that the compositions maintain one or more aspects of their physical structure and/or activity over a period of time under a designated set of conditions. In some embodiments, the period of time is at least about one hour; in some embodiments, the period of time is about 5 hours, about 10 hours, about one (1) day, about one (1) week, about two (2) weeks, about one (1) month, about two (2) months, about three (3) months, about four (4) months, about five (5) months, about six (6) months, about eight (8) months, about ten (10) months, about twelve (12) months, about twenty-four (24) months, about thirty-six (36) months, or longer. In some embodiments, the period of time is within the range of about one (1) day to about twenty-four (24) months, about two (2) weeks to about twelve (12) months, about two (2) months to about five (5) months, etc. In some embodiments, the designated conditions are ambient conditions (e.g., at room temperature and ambient pressure). In some embodiments, the designated conditions are physiologic conditions (e.g., in vivo or at about 37° C. for example in serum or in phosphate buffered saline). In some embodiments, the designated conditions are under cold storage (e.g., at or below about 4° C., −20° C., or −70° C.). In some embodiments, the designated conditions are in the dark.

"Substantially": As used herein, the term "substantially", and grammatic equivalents, refer to the qualitative condition of exhibiting total or near-total extent or degree of a characteristic or property of interest. One of ordinary skill in the art will understand that biological and chemical phenomena rarely, if ever, go to completion and/or proceed to completeness or achieve or avoid an absolute result.

"Sustained release": The term "sustained release" is used herein in accordance with its art-understood meaning of release that occurs over an extended period of time. The extended period of time can be at least about 3 days, about 5 days, about 7 days, about 10 days, about 15 days, about 30 days, about 1 month, about 2 months, about 3 months, about 6 months, or even about 1 year. In some embodiments, sustained release is substantially burst-free. In some embodiments, sustained release involves steady release over the extended period of time, so that the rate of release does not vary over the extended period of time more than about 5%, about 10%, about 15%, about 20%, about 30%, about 40% or about 50%. In some embodiments, sustained release involves release with first-order kinetics. In some embodiments, sustained release involves an initial burst, followed by a period of steady release. In some embodiments, sustained release does not involve an initial burst. In some embodiments, sustained release is substantially burst-free release.

"Therapeutic agent": As used herein, the phrase "therapeutic agent" refers to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc. In some embodiments, a therapeutic agent is any substance that can be used to alleviate, ameliorate, relieve, inhibit, prevent, delay onset of, reduce severity of, and/or reduce incidence of one or more symptoms or features of a disease, disorder, and/or condition.

"Therapeutically effective amount": As used herein, the term "therapeutically effective amount" means an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. It is specifically understood that particular subjects may, in fact, be "refractory" to a "therapeutically effective amount." To give but one example, a refractory subject may have a low bioavailability such that clinical efficacy is not obtainable. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc). Those of ordinary skill in the art will appreciate that, in some embodiments, a therapeutically effective amount may be formulated and/or administered in a single dose. In some embodiments, a therapeutically effective amount may be formulated and/or administered in a plurality of doses, for example, as part of a dosing regimen.

"Treating": As used herein, the term "treating" refers to partially or completely alleviating, ameliorating, relieving, inhibiting, preventing (for at least a period of time), delaying onset of, reducing severity of, reducing frequency of and/or reducing incidence of one or more symptoms or features of a particular disease, disorder, and/or condition. In some embodiments, treatment may be administered to a subject who does not exhibit symptoms, signs, or characteristics of a disease and/or exhibits only early symptoms, signs, and/or characteristics of the disease, for example for the purpose of decreasing the risk of developing pathology associated with the disease. In some embodiments, treatment may be administered after development of one or more symptoms, signs, and/or characteristics of the disease.

"Variant": As used herein, the term "variant" refers to an entity that shows significant structural identity with a reference entity but differs structurally from the reference entity in the presence or level of one or more chemical moieties as compared with the reference entity. In many embodiments, a variant also differs functionally from its reference entity. In general, whether a particular entity is properly considered to be a "variant" of a reference entity is based on its degree of structural identity with the reference entity. As will be appreciated by those skilled in the art, any biological or chemical reference entity has certain characteristic structural elements. A variant, by definition, is a distinct chemical entity that shares one or more such characteristic structural elements. To give but a few examples, a small molecule may have a characteristic core structural element (e.g., a macrocycle core) and/or one or more characteristic pendent moieties so that a variant of the small molecule is one that shares the core structural element and the characteristic pendent moieties but differs in other pendent moieties and/or in types of bonds present (single vs double, E vs Z, etc.) within the core, a polypeptide may have a characteristic sequence element comprised of a plurality of amino acids having designated positions relative to one another in linear or three-dimensional space and/or contributing to a particular biological function, a nucleic acid may have a characteristic sequence element comprised of a plurality of nucleotide residues having designated positions relative to on another in linear or three-dimensional space. For example, a variant polypeptide may differ from a reference polypeptide as a result of one or more differences in amino acid sequence and/or one or more differences in chemical moieties (e.g., carbohydrates, lipids, etc.) covalently attached to the polypeptide backbone. In some embodiments, a variant polypeptide shows an overall sequence identity with a reference polypeptide that is at least 85%, 86%, 87%, 88%, 89%, 90%, 91%, 92%, 93%, 94%, 95%, 96%, 97%, or 99%. Alternatively or additionally, in some embodiments, a variant polypeptide does not share at least one characteristic sequence element with a reference polypeptide. In some embodiments, the reference polypeptide has one or more biological activities. In some embodiments, a variant polypeptide shares one or more of the biological activities of the reference polypeptide. In some embodiments, a variant polypeptide lacks one or more of the biological activities of the reference polypeptide. In some embodiments, a variant polypeptide shows a reduced level of one or more biological activities as compared with the reference polypeptide. In many embodiments, a polypeptide of interest is considered to be a "variant" of a parent or reference polypeptide if the polypeptide of interest has an amino acid sequence that is identical to that of the parent but for a small number of sequence alterations at particular positions. Typically, fewer than 20%, 15%, 10%, 9%, 8%, 7%, 6%, 5%, 4%, 3%, 2% of the residues in the variant are substituted as compared with the parent. In some embodiments, a variant has 10, 9, 8, 7, 6, 5, 4, 3, 2, or 1 substituted residue as compared with a parent. Often, a variant has a very small number (e.g., fewer than 5, 4, 3, 2, or 1) number of substituted functional residues (i.e., residues that participate in a particular biological activity). Furthermore, a variant typically has not more than 5, 4, 3, 2, or 1 additions or deletions, and often has no additions or deletions, as compared with the parent. Moreover, any additions or deletions are typically fewer than about 25, about 20, about 19, about 18, about 17, about 16, about 15, about 14, about 13, about 10, about 9, about 8, about 7, about 6, and commonly are fewer than about 5, about 4, about 3, or about 2 residues. In some embodiments, the parent or reference polypeptide is one found in nature. As will be understood by those of ordinary skill in the art, a plurality of variants of a particular polypeptide of interest may commonly be found in nature, particularly when the polypeptide of interest is an infectious agent polypeptide.

DETAILED DESCRIPTION OF CERTAIN EMBODIMENTS

Among other things, the present disclosure provides a new material form of amphiphilic polypeptides, a nanofibrillar material form and methods of preparing and using nanofibrillar materials. Various embodiments according to the present disclosure are described in detail herein.

In particular, the present disclosure describes nanofibrillar materials and their use in applications, including, for example: biodegradable carrier materials, biomedical products, treatments, and/or therapies, biomaterials, bionanotechnology, biosensing, electronics, extracting agents, fillers, functional biomaterials, functional fibers (e.g. nanowires, scaffolds, etc.), gas sensing, nano-vessels, optics, optogenetics, pharmaceutical products, treatments, and/or therapies, photonics, photonic devices, sensing applications, textiles, thermal insulating catalysts, thermal insulating materials, and/or tissue engineering applications.

In some aspects, a nanofibrillar materials exhibit many material characteristics of aerogels, including nano-scale pores that provide large surface area (i.e., surface-to-volume ratio). In some embodiments provided nanofibrillar materials are characterized by unique features and properties that provide distinct advantages over traditional aerogels or aerogels-like materials. In some embodiments, provided nanofibrillar materials are fibrous, comprised of networks of nanofibrils. In some embodiments, provided nanofibrillar materials are ultralight. In some embodiments, provided nanofibrillar materials are porous. In some embodiments, provided nanofibrillar materials are characterized by large surface area. In some embodiments, provided nanofibrillar materials exhibit low density. In some embodiments, provided nanofibrillar materials exhibit favorable compressive modulus. In some embodiments, provided nanofibrillar materials exhibit optical transparency. In some embodiments, provided nanofibrillar materials exhibit low thermal conductivity.

Traditional aerogels and aerogel-like materials have been used for applications such as catalysts, particle detectors, thermal insulation, and energy absorbers.

An aerogel is a gel comprised of a microporous solid, in which the dispersed phase is a gas. Structurally, an aerogel is characterized by a monolithic internal structure, which is composed of a nano-scale network of pores and fused colloids. The pore structure of aerogels, as classified by the International Union of Pure and Applied Chemistry (IUPAC), includes three different types of pores: micropores (<2 nm in diameter), mesopores (2-50 nm in diameter), and macropores (>50 nm in diameter) with a majority of the pores falling in the mesopore range. Aerogels are typically produced via a sol-gel process. That is, aerogels are derived from a gel (e.g., hydrogel), in which the liquid component of the gel has been replaced with a gas (e.g., "air"), resulting in an ultra-light porous material with extremely low density and low thermal conductivity. To date, commercially available aerogels include microporous silica, carbon-based aerogels and zeolites.

Biopolymer materials have also been used as aerogel-like materials. Silk fibroin, from the *Bombyx mori* silk worm, is a well-known biopolymer that can be processed into several different material formats such as fibers, films, foams, sponges, and hydrogels with potential applications in areas ranging from regenerative medicine to optoelectronics. See H. Tao, D. L. Kaplan, and F. G. Omenetto, Adv. Mater., 2012, 24, 2824-37; see also F. Meersman, C. M. Dobson, and K. Heremans, Chem. Soc. Rev., 2006, 35, 908-17, the entire contents of both of which are hereby incorporated by reference herein. Depending on the self-assembly of the crystalline solid or molecular liquid, silk fibroin materials can form nanoscale features to be used for optics, electronics, and biomaterial applications. See S. Zarkoob, D. H. Reneker, R. K. Eby, S. D. Hudson, D. Ertley, and W. W. Adams, in American Chemical Society, Polymer Preprints, Division of Polymer Chemistry, ACS, 1998, vol. 39, pp. 244-245; see also S. Kim, B. Marelli, M. A. Brenckle, A. N. Mitropoulos, E.-S. Gil, K. Tsioris, H. Tao, D. L. Kaplan, and F. G. Omenetto, Nat. Nanotechnol., 2014, 9, 306-10, the entire contents of both of which are hereby incorporated by reference herein.

Despite several applications of silk fibroin in biomedical engineering, the unique nanofiber structure defining the superior mechanical properties of silk are completely destroyed during silk dissolution in traditional solvents and lack the regeneration of fibers. See F. Zhang, Q. Lu, J. Ming, H. Dou, Z. Liu, B. Zuo, M. Qin, F. Li, D. L. Kaplan, and X. Zhang, J. Mater. Chem. B, 2014, 2, 3879, the entire contents of which are hereby incorporated by reference herein. Current fabrication methods with silk fibroin to produce nanostructured materials lack the capability to create functional 3D forms, such as porous nano-fiber, without using a sacrificial material.

Indeed, until the present disclosure, biopolymer or organic polypeptides would form monolithic micro- and/or nano-sized particles (i.e., colloids), highly porous fibers were not attainable.

Silk is an excellent candidate for advanced materials due to its excellent mechanical and optical properties, natural self-assembly, ease of conforming to nanoscale sizes combined with its biodegradability, functionalization, and dopability.

In some embodiments, nanofibrillar materials as described in the present disclosure are predominantly comprised of amphiphilic polypeptide nanofibrils, and in particular silk fibroin amphiphilic polypeptide nanofibrils. In some embodiments, nanofibrils, nano-sized fibers, exhibit an extensive network of interconnected pores resulting in a high surface-to-volume ratio. In some embodiments, a surface-to-volume ratio of interconnected pores of nanofibrillar materials is at least comparable to or exceeding that of typical aerogels.

The process of forming nano-fibers is regulated by the phase transitions occurring in amphiphilic domains of polypeptides where long hydrophobic crystallizable blocks and short hydrophilic spacers modulate intermolecular hydrogen bonded β-sheet formation in a presence of water. See H.-J. Jin and D. L. Kaplan, Nature, 2003, 424, 1057-61, the entire contents of which is hereby incorporated by reference herein. The encouragement of macromolecular interactions from the hydrophobic side chains initiating hydrogen bonding can occur by exposure of silk solution to electric fields, changes in pH, heat and water removal, shear forces, or polar solvents. See S. Nagarkar, T. Nicolai, C. Chassenieux, and A. Lele, Phys. Chem. Chem. Phys., 2010, 12, 3834-44; N. Kojic, M. J. Panzer, G. G. Leisk, W. K. Raja, M. Kojic, and D. L. Kaplan, Soft Matter, 2012, 8, 6897, the entire contents of both of which are hereby incorporated by reference herein. However, transformations also respond to changes in pressure to design intermolecular bonded nanofibrils during water removal. See F. Zhang, Q. Lu, J. Ming, H. Dou, Z. Liu, B. Zuo, M. Qin, F. Li, D. L. Kaplan, and X. Zhang, J. Mater. Chem. B, 2014, 2, 3879, the entire contents of which are hereby incorporated by reference herein. The pressure associated with these transformations occurs during supercritical drying of silk gels to form aerogels with fibril structures and cause pressure induced changes at the molecular level.

In some embodiments, when a formulation of reconstituted silk is mixed with acetone and critically point dried in supercritical carbon dioxide, nanofibrils are observed with a pore structure matching or exceeding that of aerogels. In some embodiments, supercritical drying with supercritical fluids, such as carbon dioxide of transparent silk fibroin hydrogels obtained with the acetone process induces a pressure-dependent organization of the silk fibroin molecules; material anisotropy and formation of nanofibrillar materials. Supercritical drying with carbon dioxide of transparent silk fibroin hydrogels obtained with the acetone process imparts conformational changes in the polypeptide structure, resulting in the formation of a more crystalline structure when compared to other silk formats, for example, methanol treated silk films and HFIP silk blocks.

Nanofibrillar Materials

In some embodiments, nanofibrillar materials as provided herein are made from amphiphilic polypeptides.

In some embodiments, polypeptides useful in forming nanofibrillar materials as disclosed herein, for example, include: agarose, alginate, cellulose, chitin, chitosan, collagen, elastin, gelatin, hyaluronic acid, polydimethylsiloxane, poly(ethylene glycol), polyhydroxyalkanoates, poly(lactide-co-glycolide), pullan, resilin, silk, starch, or combinations thereof. In some embodiments, nanofibrillar materials are made of or comprise polypeptides from a single source, for example naturally occurring proteins. In some embodiments, polypeptides may be produced from various sources, including a regenerated protein from natural sources, such as purified protein. In some embodiments, polypeptides were produced from recombinant proteins. In some embodiments, recombinant proteins were produced from heterologous systems, were synthetically produced, were chemically produced, or combinations thereof.

In some embodiments, nanofibrillar materials are made of a polypeptides corresponding to any one of the list provided above, with or without one or more sequence variations, as compared to the native or wild type counterpart. In some embodiments, for example, such variants may show at least 85% overall sequence identity as compared to a wild type sequence. In some embodiments, for example, such variants may show at least 86%, 87%, 88%, 89%, 90%, 91%, 92%, 93%, 94%, 95%, 96%, 97%, 98%, 99% overall sequence identity.

In some embodiments, nanofibrillar materials of the present disclosure are or comprise polypeptides having an amino acid sequence, for example, including at least one of selected from the following list: fibroins, actins, collagens, catenins, claudins, coilins, elastins, elaunins, extensins, fibrillins, lamins, laminins, keratins, tublins, viral structural proteins, zein proteins (seed storage protein), or combinations thereof. In some embodiments, nanofibrillar materials as described herein may comprise silk fibroin polypeptides. In some embodiments, nanofibrillar materials as described herein consists essentially of silk fibroin polypeptides. In some embodiments, silk fibroin polypeptides are or comprise *Bombyx mori* fibroin.

In some embodiments, polypeptides having an amino acid sequence corresponding to fragments derived from silk fibroin protein or variants thereof. In the context of nanofibrillar materials of the present disclosure, silk fibroin fragments generally refer to silk fibroin peptide chains or polypeptides that are smaller than naturally occurring full length silk fibroin counterpart, such that one or more of the silk fibroin fragments within a population or composition are less than 500 kDa, less than 450 kDa, less than 400 kDa, less than 350 kDa, less than 300 kDa, less than 250 kDa, less than 200 kDa, less than 175 kDa, less than 150 kDa, less than 120 kDa, less than 100 kDa, less than 90 kDa, less than 80 kDa, less than 70 kDa, less than 60 kDa, less than 50 kDa, less than 40 kDa, less than 30 kDa, less than 25 kDa, less than 20 kDa, less than 15 kDa, less than 12 kDa, less than 10 kDa, less than 9 kDa, less than 8 kDa, less than 7 kDa, less than 6 kDa, less than 5 kDa, less than 4 kDa, less than 3.5 kDa, less than 3 kDa, less than 2.5 kDa, less than 2 kDa, less than 1.5 kDa, or less than about 1.0 kDa, etc.

In some embodiments, when a critical point drying process is applied to micellar or in some cases micellar-based colloidal nanoparticles composed of polypeptides that are amphiphilic in nature, nanofibrillar materials of desirable properties can be generated. As described in further detail herein, nanofibrillar materials are fibrous, highly nanoporous, have low bulk density, have favorable compressive stress, and are optically transparent. Unlike peptide-based materials described in the existing literature, nanofibrillar materials disclosed herein do not show the lamellar morphology (also referred to as "leaf-like" and "slate" morphology) often observed in peptide-based materials produced by freeze-drying. Instead, nanofibrillar materials provided herein are fibrillar yet monolithic in that mechanical features of the materials are uniformly distributed within the material, providing superior material properties, as compared to previously reported peptide-based materials, such as protein blocks generated by freeze-drying.

Figure 3:
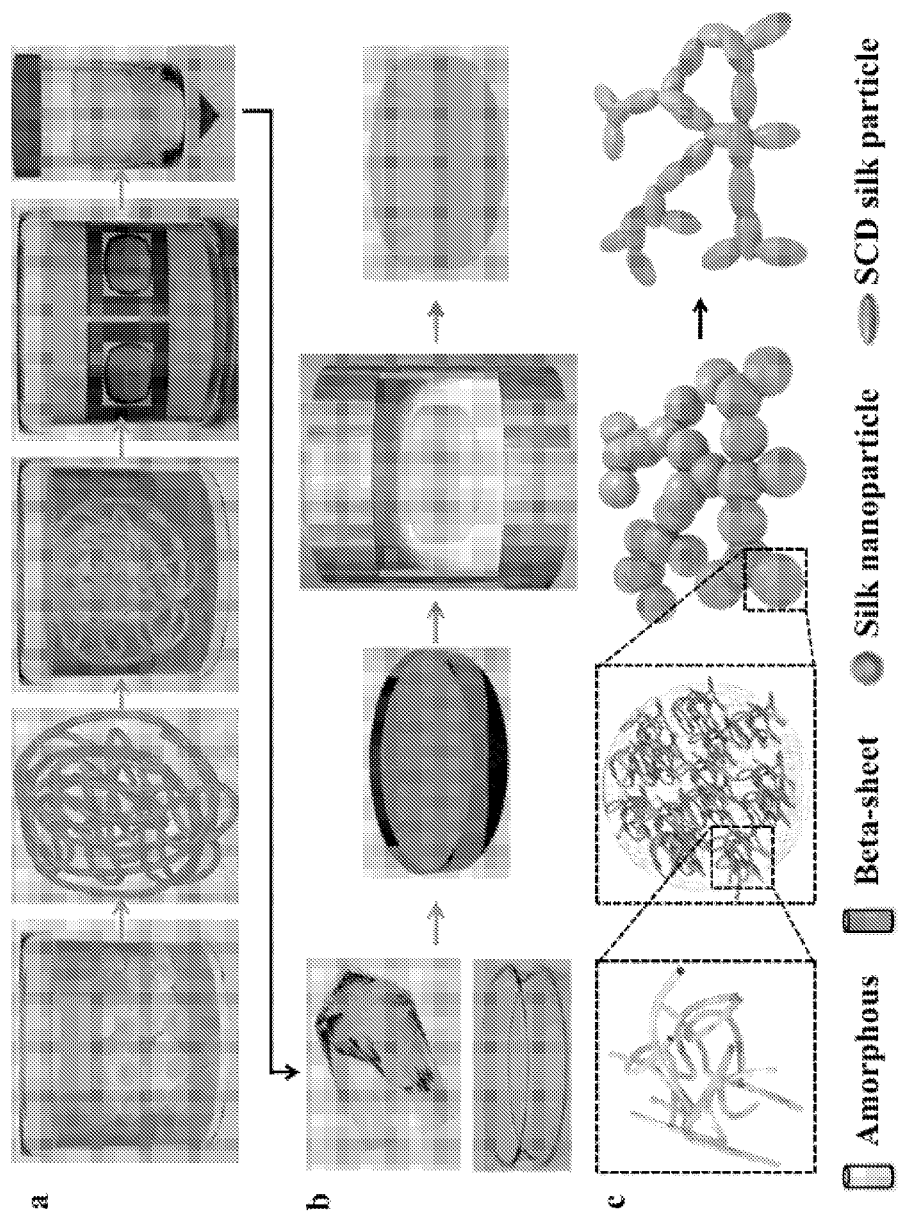
FIG. 3. shows a flowchart illustrating a method to assemble solubilized silk fibroin into nanofibers, which enables the formation of a translucent silk fibroin nanofibrillar materials with defined shapes and dimensions.

In some embodiments, nanofibrillar materials of the present disclosure have unique morphology and features. In some embodiments, nanofibrillar materials are fibrous and porous. In some embodiments, silk fibroin nanofibrillar materials as provided herein and shown in FIG. 3 exhibit defined shapes and dimensions. Additionally, supercritical drying of silk hydrogels, as shown in FIG. 4a, produces silk nanofibrillar materials with nanofiber morphology, as shown in FIG. 4b, that maintain activity of biological compounds to be used as fluorescence gas sensors in a degradable biological protein.

Fibrous

In some embodiments, nanofibrillar materials as described herein comprise nanofibrils, nano-sized fibers. In some embodiments, nanofibrils are substantially uniformly distributed within three-dimensional space of a nanofibrillar material, forming networks of nano-sized fibers. Without wishing to be bound by a particular theory, it is believed that nanofibers that make up the nanofibrillar materials described herein are formed from fused micellar particles. Moreover, it is contemplated that critical point drying or supercritical drying triggers or otherwise facilitates a structural transition from micelles/nanoparticles to nanofibrils observed in nanofibrillar materials of the present disclosure.

In some embodiments, nano-sized fibers of such nanofibrillar materials have average diameters between about 2 nm and about 100 nm, for example, between about 5-35 nm, between about 10-30 nm, between about 15-25 nm, e.g., about 5 nm, about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, about 21 nm, about 22 nm, about 23 nm, about 24 nm, about 25 nm, about 26 nm, about 27 nm, about 28 nm, about 29 nm, about 30 nm, about 31 nm, about 32 nm, about 33 nm, about 34 nm, about 35 nm, about 36 nm, about 37 nm, about 38 nm, about 39 nm, about 40 nm, about 45 nm, about 50 nm, about 55 nm, about 60 nm, about 65 nm, about 70 nm, about 75 nm, about 80 nm, about 85 nm, about 90 nm, about 95 nm, or about 100 nm.

Porous

Highly porous materials present advantages over structures in terms of diffusion efficiency and surface area, and thus have utility as catalyst supports or electrodes for electrochemical devices. See L. W. Hrubesh, J. Non. Cryst. Solids, 1998, 225, 335-342, the entire contents of which are hereby incorporated by reference herein. Access to high surface areas normally requires predesigned sacrificial frameworks and the structural morphology ultimately determines the textural properties of the material. See D. N. Rockwood, R. C. Preda, T. Yücel, X. Wang, M. L. Lovett, and D. L. Kaplan, Nat. Protoc., 2011, 6, 1612-31, the entire contents of which are hereby incorporated by reference herein. In some embodiments, nanofibrillar materials as provided herein are highly porous. In some embodiments, nano-sized pores of nanofibrillar materials are interconnected.

In some embodiments, pores observed in nanofibrillar materials of the present disclosure are nano-sized pores, e.g., between about 2 nm and 100 nm in diameter. In some embodiments, a majority of the pores have diameters between about 5 nm and about 100 nm. In some embodiments, a majority of pores have diameters between about 10 nm and about 90 nm. In some embodiments, a majority of pores have diameters between about 15 nm and about 85 nm. In some embodiments, a majority of pores have diameters between about 20 nm and about 80 nm. In some embodiments, a majority of pores have diameters between about 25 nm and about 75 nm. In some embodiments, a majority of pores have diameters between about 30 nm and about 70 nm.

In some embodiments, a majority of pores in nanofibrillar materials of the present disclosure have diameters in a mesopore range. In some embodiments, at least 50%, at least 55%, at least 60%, at least 65%, at least 70%, at least 75%, at least 80%, at least 85%, at least 90% or at least 95% of pores observed in nanofibrillar materials are in the mesopore range.

In some embodiments, an average diameter of pores of nanofibrillar materials of the present disclosure is about 2 nm, about 3 nm, about 4 nm, about 5 nm, about 10 nm, about 15 nm, about 20 nm, about 25 nm, about 30 nm, about 35 nm, about 40 nm, about 45 nm, about 50 nm, about 55 nm, about 60 nm, about 65 nm, about 70 nm, about 75 nm, about 80 nm, about 85 nm, about 90 nm, about 95 nm, or about 100 nm.

In some embodiments, such nanofibrillar materials of the present disclosure show porosity of at least 0.8, but typically at least 0.9. In some embodiments, nanofibrillar materials of the present disclosure are at least about 90% porous, e.g., about 91%, about 92%, about 93%, about 94%, about 95%, about 96%, about 97%, about 98%, about 99% porous. In some embodiments, such materials have a porosity greater than 99%, e.g., about 99.1%, about 99.2%, about 99.3%, about 99.4%, about 99.5%, about 99.6%, about 99.7%, about 99.8%, about 99.9%. Therefore, nanofibrillar materials of the present disclosure are ultra-light and show high surface area to volume ratios.

In some embodiments, as indicated nanofibrillar materials as disclosed herein exhibit properties, such as low bulk density, favorable compressive modulus, optical transparency, and low thermal conductivity that match or exceed those in traditional aerogels and aerogel-like materials.

Figure 5:
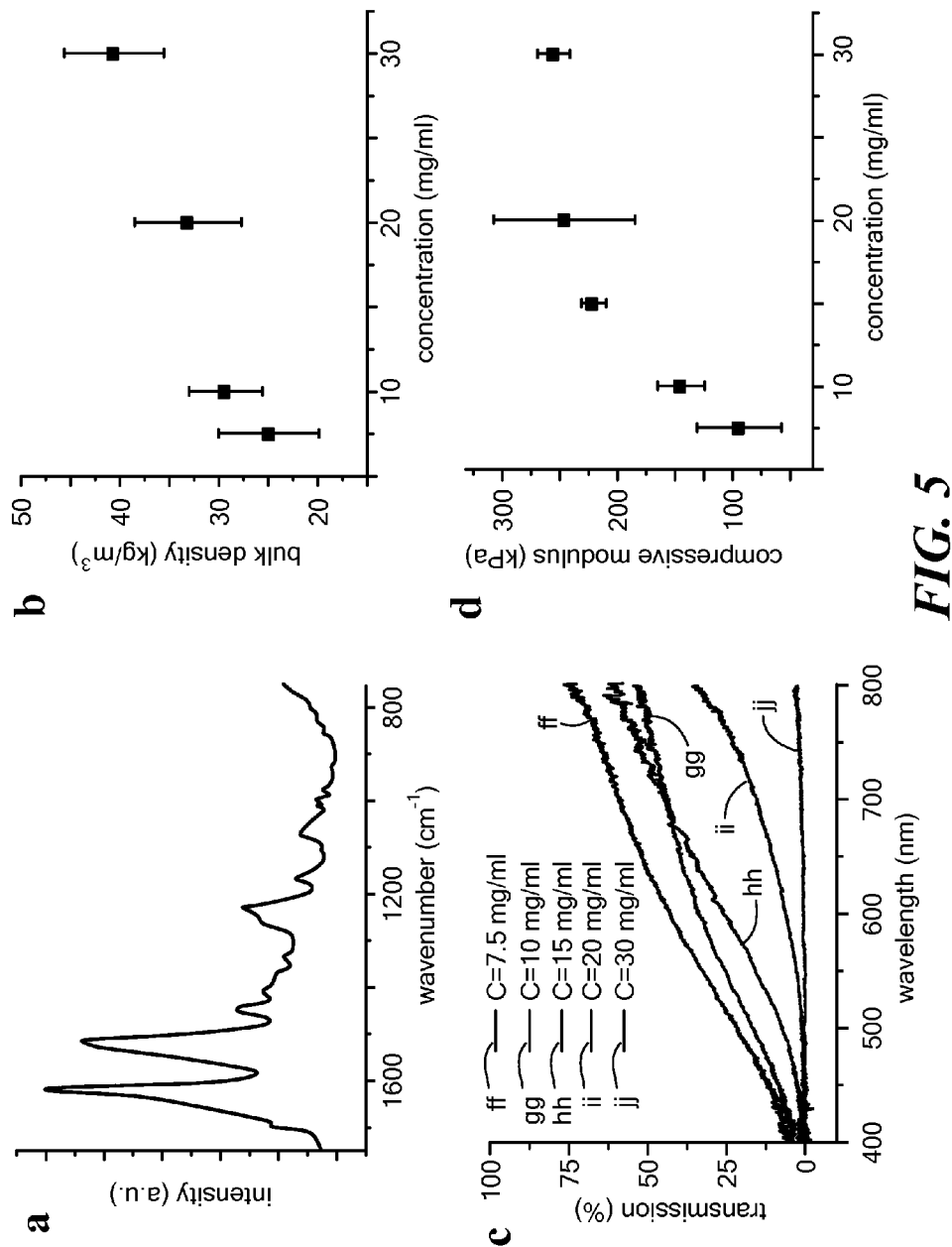
FIG. 5. shows chemical and physical characterization of silk fibroin nanofibrillar materials.

FIG. 5 shows chemical and physical characterization of silk fibroin nanofibrillar materials. FIG. 5a shows ATR- FTIR spectra of silk fibroin hydrogel before supercritical $CO_2$ drying and silk fibroin nanofibrillar materials after supercritical CO2 drying. FIG. 5b shows bulk density of silk nanofibrillar materials measured with different initial silk concentrations. FIG. 5c shows transmission measurements of silk fibroin nanofibrillar materials with different initial silk concentrations. FIG. 5d shows compressive modulus of silk fibroin nanofibrillar materials with different initial silk concentrations.

Low Density

In some embodiments, nanofibrillar materials of the present disclosure may be produced to have extremely low bulk densities. In some embodiments, relative bulk densities of nanofibrillar materials of the present disclosure may be adjusted by varying a concentration of an amphiphilic polypeptide solution used as a starting material.

Bulk density of nanofibrillar materials of the present disclosure is shown in FIG. 5b as a function of starting silk concentration. Nanofibrillar material bulk densities range from 23 $kg/m^3$ to 40 $kg/m^3$ and are higher compared to their initial hydrogel densities. Increasing bulk density of nanofibrillar materials compared to precursor hydrogels occurs during hydrogel synthesis and contraction of nanofibrillar materials during supercritical drying. During supercritical extraction, shrinkage is attributed to a physical shift to more favorable equilibrium states resulting in a reduction of overall volume as silk polypeptides experience high pressure perturbing of a hydration shell during drying. See M. L. Floren, S. Spilimbergo, A. Motta, and C. Migliaresi, Biomacromolecules, 2012, 13, 2060-2072, the entire contents of which are hereby incorporated by reference herein. This results in an average contraction of ~10% from an initial hydrated state and is also observed in other nanofibrillar materials.

In some embodiments, nanofibrillar materials of the present disclosure show less than 75 $kg/m^3$ bulk density, e.g., 70 $kg/m^3$ bulk density, e.g., 65 $kg/m^3$ bulk density, e.g., 60 $kg/m^3$ bulk density, e.g., 55 $kg/m^3$ bulk density, e.g., 50 $kg/m^3$ bulk density, e.g., less than 45 $kg/m^3$, less than 40 $kg/m^3$, less than 35 $kg/m^3$, less than 30 $kg/m^3$, less than 25 $kg/m^3$, less than 20 $kg/m^3$, less than 15 $kg/m^3$, less than 10 $kg/m^3$.

In some embodiments, nanofibrillar materials of the present disclosure show bulk density of about 50 $kg/m^3$, about 49 $kg/m^3$, about 48 $kg/m^3$, about 47 $kg/m^3$, about 46 $kg/m^3$, about 45 $kg/m^3$, about 44 $kg/m^3$, about 43 $kg/m^3$, about 42 $kg/m^3$, about 41 $kg/m^3$, about 40 $kg/m^3$, about 39 $kg/m^3$, about 38 $kg/m^3$, about 37 $kg/m^3$, about 36 $kg/m^3$, about 35 $kg/m^3$, about 34 $kg/m^3$, about 33 $kg/m^3$, about 32 $kg/m^3$, about 31 $kg/m^3$, about 30 $kg/m^3$, about 29 $kg/m^3$, about 28 $kg/m^3$, about 27 $kg/m^3$, about 26 $kg/m^3$, about 25 $kg/m^3$, about 24 $kg/m^3$, about 23 $kg/m^3$, about 22 $kg/m^3$, about 21 $kg/m^3$, about 20 $kg/m^3$, about 19 $kg/m^3$, about 18 $kg/m^3$, about 17 $kg/m^3$, about 16 $kg/m^3$, about 15 $kg/m^3$, about 14 $kg/m^3$, about 13 $kg/m^3$, about 12 $kg/m^3$, about 11 $kg/m^3$, about 10 $kg/m^3$, about 9 $kg/m^3$, or about 8 $kg/m^3$.

Figure 2:
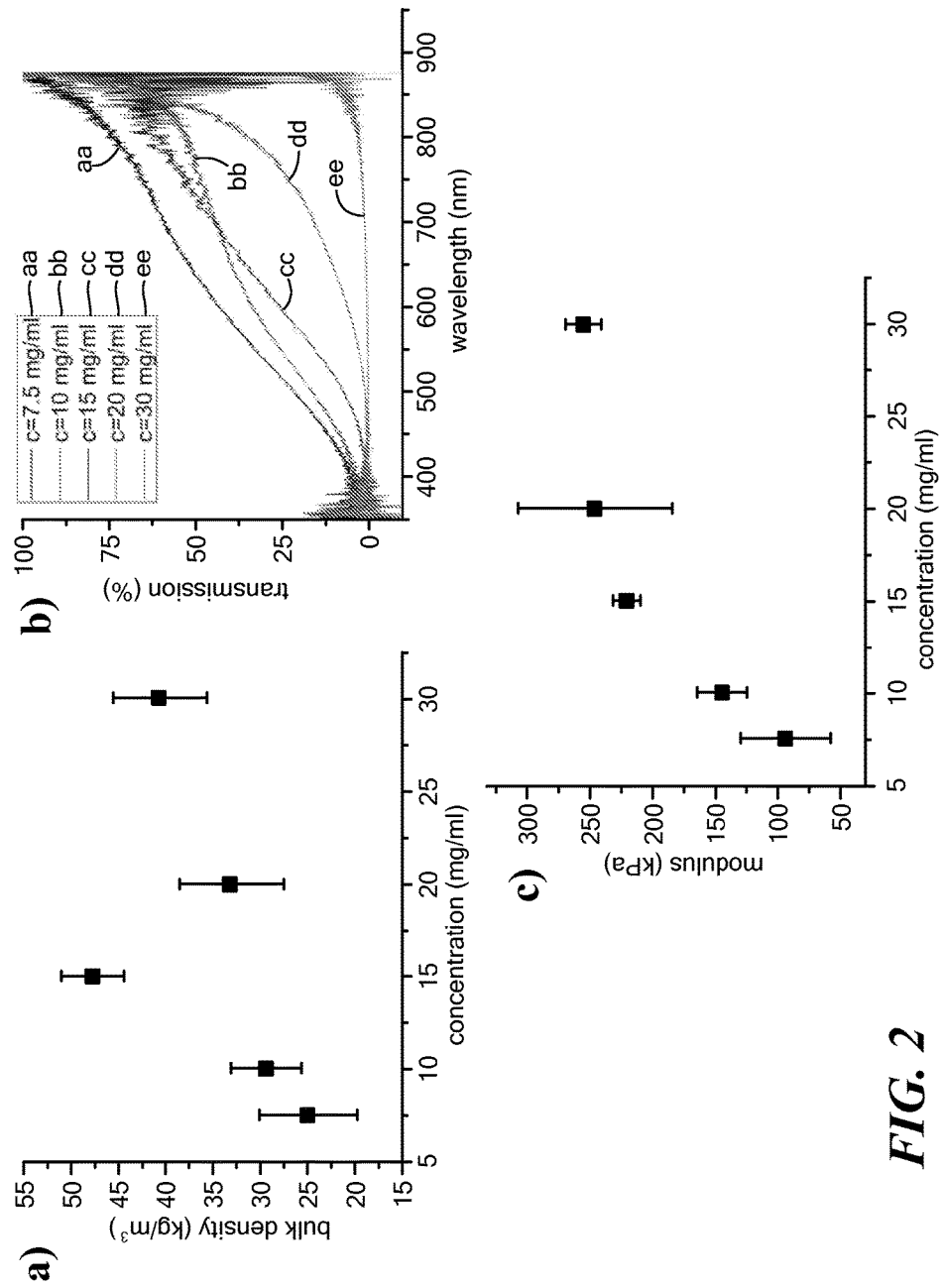
FIG. 2. shows data and graphs of FIG. 2a bulk density, FIG. 2b transmission spectra, and FIG. 2c compression modulus of silk nanofibrillar materials as a function of an initial silk concentration of 7.5 mg/ml, 10 mg/ml, 15 mg/ml, 20 mg/ml, and 30 mg/ml.

In some embodiments, nanofibrillar materials of the present disclosure show bulk density of about 20-40 $kg/m^3$ when a peptide solution at a concentration of 1.0% is used as a starting material. Non-limiting embodiments are provided in FIG. 2 to illustrate relative bulk density of nanofibrillar materials produced in accordance with the present disclosure.

Compressive Modulus

In some embodiments, nanofibrillar materials of the present disclosure may be produced to have favorable compressive properties. Various parameters to evaluate such properties, as well as techniques and devices to allow such measurements, are well known in the art. Unconfined compressive properties of nanofibrillar materials may be measured using any suitable devices, such as an Instron 3366 testing frame (Instron, Norwood, Mass.). As an example, such measurements may be made with a crosshead speed of 2 mm/min with a 100 N capacity load cell. Samples may be conducted in air between force plates. Linear elastic modulus may be calculated using a least-squared fitting in a linear region.

Figure 7:
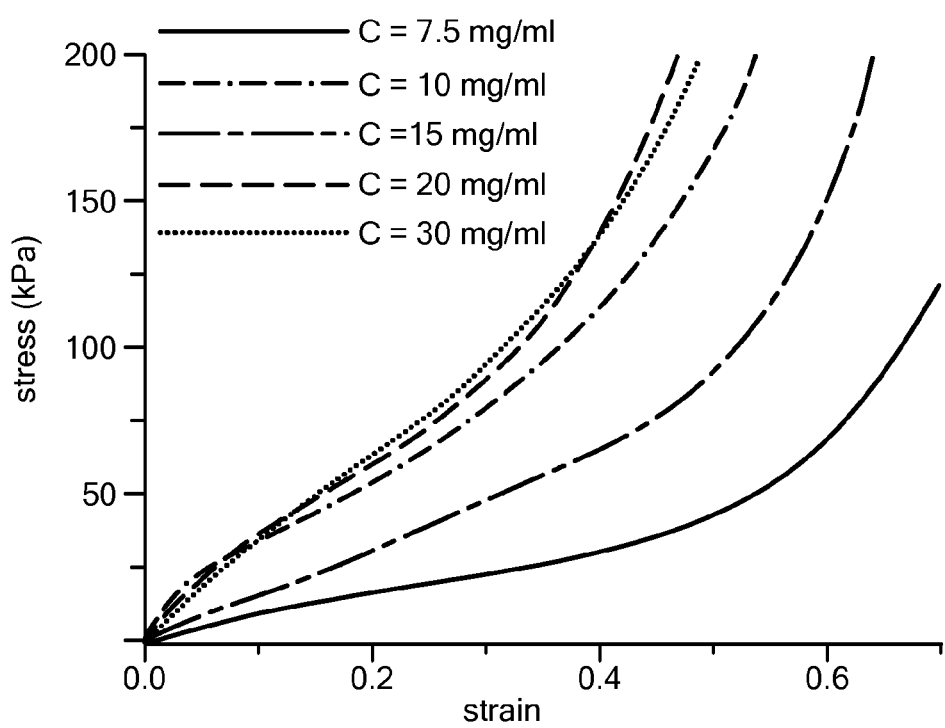
FIG. 7. shows representative stress-strain curves of silk fibroin nanofibrillar materials.

Compressive tests were carried out to evaluate an effect of silk fibroin concentration on mechanical properties of nanofibrillar materials. FIG. 7 illustrates representative stress stress-strain curves at a single crosshead speed for increased silk fibroin concentrations. All samples showed a densification behavior distinctive of plastic materials, where low compressive stress generates high material deformation. As shown in FIG. 5d, typical plastic behavior of silk nanofibrillar materials was also depicted as nanofibrillar materials were compressed increasing stiffness as nanofibrillar materials experienced higher degrees of deformation. By controlling initial silk fibroin concentration it was possible to regulate compressive modulus of nanofibrillar material from 95 kPa to 250 kPa, which corresponds to stiffness of many tissues found in the human body. Additionally, added crystallinity of polypeptides supercritical drying, which has been previously reported to control silk degradation along with high porosity and size of nanofibers can be used to impact cell differentiation and overall cell behavior.

Using the paradigm described above, in some embodiments, nanofibrillar materials of the present disclosure exhibit a compressive modulus of between about 50 kPa and about 300 kPa, e.g., about 50 kPa, about 60 kPa, about 70 kPa, about 80 kPa, about 90 kPa, about 100 kPa, about 110 kPa, about 120 kPa, about 130 kPa, about 140 kPa, about 150 kPa, about 160 kPa, about 170 kPa, about 180 kPa, about 190 kPa, about 200 kPa, about 210 kPa, about 220 kPa, about 230 kPa, about 240 kPa, about 250 kPa, about 260 kPa, about 270 kPa, about 280 kPa, about 290 kPa, about 300 kPa.

In some embodiments, nanofibrillar materials of the present disclosure prepared from a 1% polypeptide solution may exhibit a compressive modulus of about 70 kPa, about 80 kPa, about 90 kPa, about 100 kPa, about 110 kPa, about 120 kPa, about 130 kPa, about 140 kPa, about 150 kPa, about 160 kPa, about 170 kPa, about 180 kPa, about 190 kPa, about 200 kPa, about 210 kPa, or about 220 kPa.

Optically Transparent

In some embodiments, nanofibrillar materials of the present disclosure exhibit desirable optical transparency. With respect to optical transparency, generally speaking, increasing a concentration of an amphiphilic polypeptide solution used as a starting material can generate increasingly opaque nanofibrillar materials. As shown in FIG. 1 and FIG. 2b, which depict concentration-dependent changes in optical transparency of resulting nanofibrillar materials as measured by light transmission, using a silk fibroin-based material as an example. Similar results are obtained in other nanofibrillar materials produced from other beta-sheet containing proteins, such as keratin.

Optical transmission of nanofibrillar materials as defined by an initial starting concentrations was examined to determine transparency after supercritical drying. Optical transparency in a visible range is renders silk nanofibrillar materials appropriate for use with optical sources while maintaining structural integrity. FIG. 5c shows silk nanofibrillar material transmission as a function of initial silk concentration over visible wavelengths. A highest observed transmission is 70% at wavelengths greater than 650 nm while an intensity value at 600 nm of a negative linear relationship associated with initial silk concentration from 60% transmission to 3% transmission. A decrease in transmission can be attributed to a number of interconnections within each nanofibrillar material and a size and spacing of generated pores. Lower transmission is also observed during hydrogel formation from a uniform scattering of visible light.

In some embodiments, nanofibrillar materials of the present disclosure allow up to about 99% transmittance of light having various wavelengths, e.g., between about 500 and 880 nm, depending on the thickness of a nanofibrillar material being measured. For example, optical transparency may be measured using an nanofibrillar materials having a thickness of about 10 mm, about 9 mm, about 8 mm, about 7 mm, about 6 mm, about 5 mm, about 4 mm, about 3 mm, about 2 mm, about 1 mm, about 0.5 mm, etc. In some embodiments, nanofibrillar materials of the present disclosure show between about 5% and about 95% of light transmission, such as about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, about 99%, and greater.

Methods of Forming Nanofibrillar Materials

The present disclosure further includes methods for forming nanofibrillar materials. Methods disclosed herein are based at least in part on a recognition that when an amphiphilic polypeptide materials are dehydrated with an organic solvent (such as alcohols) and super critically dried, nanofiber-containing nanofibrillar materials are observed, which contain a pore structure and certain other material features matching or exceeding those for traditional aerogels and aerogel-like materials.

Accordingly, in some embodiments, methods for producing nanofibrillar materials as described herein includes providing an amphiphilic polypeptide hydrogel. In some embodiments, methods for producing nanofibrillar materials including providing an amphiphilic hydrogel include providing a peptide solution containing amphiphilic peptide micelles. In some embodiments, amphiphilic peptide micelles are processed to form an amphiphilic hydrogel. In some embodiments, methods for producing nanofibrillar materials, a hydrogel includes colloidal nanoparticles comprising an aggregate of micelles. In some embodiments, methods for producing nanofibrillar materials having an aggregate of micelles, micelles are amorphous micelles, helically structured micelles, or combination thereof. In some embodiments, a solution of an amphiphilic polypeptide comprises fused nano-sized micelles. In some embodiments, methods including providing an amphiphilic hydrogel includes soaking an amphiphilic hydrogel in EDTA to increase hydrogel stiffness.

In some embodiments, a step of providing an amphiphilic polypeptide hydrogel comprises providing a solution of an amphiphilic polypeptide. In some embodiments, a solution of an amphiphilic polypeptide includes agarose, alginate, cellulose, chitin, chitosan, collagen, elastin, gelatin, hyaluronic acid, polydimethylsiloxane, poly(ethylene glycol), polyhydroxyalkanoates, poly(lactide-co-glycolide), pullan, resilin, silk, starch, or combinations thereof. In some embodiments, a solution of an amphiphilic polypeptide having an amino acid sequence, for example, including at least one of selected from the following list: fibroins, actins, collagens, catenins, claudins, coilins, elastins, elaunins, extensins, fibrillins, lamins, laminins, keratins, tublins, viral structural proteins, zein proteins (seed storage protein), or combinations thereof.

In some embodiments, a step of providing an amphiphilic polypeptide hydrogel comprises providing a solution of an amphiphilic polypeptide is or comprises silk fibroin polypeptides. In some embodiments, nanofibrillar materials as described herein consists essentially of silk fibroin polypeptides. In some embodiments, silk fibroin polypeptides are or comprise *Bombyx mori* fibroin.

In some embodiments, a step of providing an amphiphilic polypeptide hydrogel comprises providing a solution of silk fibroin with an average molecular weight of silk fibroin between about 10 kDa and about 400 kDa.

In some embodiments, a step of providing an amphiphilic polypeptide hydrogel comprises providing a solution of silk fibroin with an average molecular weight of silk fibroin less than 500 kDa, less than 450 kDa, less than 400 kDa, less than 350 kDa, less than 300 kDa, less than 250 kDa, less than 200 kDa, less than 175 kDa, less than 150 kDa, less than 120 kDa, less than 100 kDa, less than 90 kDa, less than 80 kDa, less than 70 kDa, less than 60 kDa, less than 50 kDa, less than 40 kDa, less than 30 kDa, less than 25 kDa, less than 20 kDa, less than 15 kDa, less than 12 kDa, less than 10 kDa, less than 9 kDa, less than 8 kDa, less than 7 kDa, less than 6 kDa, less than 5 kDa, less than 4 kDa, less than 3.5 kDa, less than 3 kDa, less than 2.5 kDa, less than 2 kDa, less than 1.5 kDa, or less than about 1.0 kDa, etc.

In some embodiments, a step of providing an amphiphilic polypeptide hydrogel comprises providing a solution of silk fibroin with an average molecular weight of silk fibroin between 5 kDa and 125 kDa, i.e. low molecular weight silk fibroin. Low molecular weight silk fibroin is described in detail in U.S. provisional application No. 61/883,732, entitled "LOW MOLECULAR WEIGHT SILK FIBROIN AND USES THEREOF" and PCT international patent application no.: PCT/US2014/029636, entitled "LOW MOLECULAR WEIGHT SILK COMPOSITIONS AND STABILIZING SILK COMPOSITIONS," the entire contents of both of which are hereby incorporated by reference herein.

In some embodiments, a step of providing the solution of an amphiphilic polypeptide comprises selecting an average molecular weight of silk fibroin for matching, tuning, adjusting, and/or manipulating mechanical properties of the nanofibrillar material.

In some embodiments, a step of providing the solution of an amphiphilic polypeptide includes an amphiphilic polypeptide peptide solution having a solution concentration is between about 0.01% wt/vol and about 20.0% wt/vol.

In some embodiments, a step of providing an amphiphilic polypeptide hydrogel comprises providing a solution of silk fibroin having a solution concentration between about 0.01% wt/vol and about 20.0% wt/vol, e.g., about 0.02% wt/vol, 0.05% wt/vol, 0.1% wt/vol, 0.2% wt/vol, 0.3% wt/vol, 0.4% wt/vol, 0.5% wt/vol, 0.6% wt/vol, 0.7% wt/vol, 0.8% wt/vol, 0.9% wt/vol, 1.0% wt/vol, 1.5% wt/vol, 2.0% wt/vol, 2.5% wt/vol, 3.0% wt/vol, 3.5% wt/vol, 4.0% wt/vol, 4.5% wt/vol, 5.0% wt/vol, 5.5% wt/vol, 6.0% wt/vol, 6.5% wt/vol, 7.0% wt/vol, 7.5% wt/vol, 8.0% wt/vol, 8.5% wt/vol, 9.0% wt/vol, 9.5% wt/vol, 10.0% wt/vol, 10.5% wt/vol, 11.0% wt/vol, 11.5% wt/vol, 12.0% wt/vol, 12.5% wt/vol, 13.0% wt/vol, 13.5% wt/vol, 14.0% wt/vol, 14.5% wt/vol, 15.0% wt/vol, 15.5% wt/vol, 16.0% wt/vol, 16.5% wt/vol, 17.0% wt/vol, 17.5% wt/vol, 18.0% wt/vol, 18.5% wt/vol, 19.0% wt/vol, 19.5% wt/vol, 20.0% wt/vol, or greater.

In some embodiments, a step of providing the solution of an amphiphilic polypeptide comprises selecting a solution concentration of silk fibroin for matching, tuning, adjusting, and/or manipulating mechanical properties of the nanofibrillar material.

In some embodiments, methods for producing nanofibrillar materials including a step of providing the solution of the amphiphilic polypeptide further comprises introducing acetone to the solution and evaporating the acetone thereby inducing hydrogel formation.

In some embodiments, methods for producing nanofibrillar materials includes dehydrating the amphiphilic polypeptide hydrogel using an organic solvent. In some embodiments, a step of dehydrating includes an organic solvent that is or comprises methanol, ethanol, acetone, isopropanol, a halogenated derivative thereof (F, Cl, Br or I), or combinations thereof.

In some embodiments, methods for producing nanofibrillar materials includes supercritical drying (also referred to as critical point drying) of a dehydrated hydrogel to form a nanofibrillar material. In some embodiments, a the step of supercritical drying includes providing a supercritical fluid and applying a pressure of between about 1000 psi and about 5000 psi.

In some embodiments, supercritically drying is regulated by phase transitions occurring in the amphiphilic domains of the protein where long hydrophobic crystallizable blocks and short hydrophilic spacers modulate intermolecular hydrogen bonded β-sheet formation in the presence of water. H. J. Jin and D. L. Kaplan, *Nature*, 2003, 424, 1057-61, the entire contents of which are hereby incorporated by reference herein. When a liquid material is dried from a gel, typically the liquid material crosses a phase boundary from liquid to gas. In such cases, the amount of liquid decreases, which results in increasing surface tension in the liquid material. When the liquid material is in contact with sensitive structures, the tension caused results in damage to the structural integrity of any structures the liquid comes into contact. By contrast, with supercritical drying of a gel, liquid material does not cross a phase boundary when transforming from a liquid to a gas. Instead, passing through a supercritical region beyond a critical point of the phase diagram where the density of the liquid state of the material is equal to the density of the gaseous state of the material.

In some embodiments, supercritical drying of amphiphilic polypeptide hydrogels with a supercritical fluid includes carbon dioxide.

In some embodiments, supercritical drying of hydrogels occurs with other substances besides carbon dioxide. In some embodiments, supercritical drying of amphiphilic polypeptide hydrogels with a supercritical fluid, for example, including ammonia, ethylene, ethane, fluoroform, nitrous oxide, propane, freon, or xenon as a supercritical fluid. The reasons for using carbon dioxide compared to other substances are the critical temperature and pressure of the extraction fluid are considered dangerous and some result in ignition at the critical conditions. See J. R. Williams, A. A. Clifford, and S. H. R. al-Saidi, Mol. Biotechnol., 2002, 22, 263-286, the entire contents of which are hereby incorporated by reference herein. Carbon dioxide is a favored supercritical extraction fluid because its critical point is at relatively low pressure and temperature (31° C., 1070 psi) and not ignitable. Other possible useful substances that have been considered for supercritical fluid extraction (and would be within the acceptable range to be used with silk fibroin) are ammonia, ethylene, ethane, fluoroform, nitrous oxide, propane, freon, and xenon. The maximum critical temperature is 406 K (ammonia) with the remaining substances having a critical temperature below 310 K, and the maximum critical pressure is 1650 psi (ammonia) with the remaining substances having a critical pressure below that of carbon dioxide. The pressure range for supercritical fluid extraction has been attempted at pressures up to 5000 psi, which changes the supercritical fluid properties of the substance (density, etc.), but are at the boundary of the conditions considered dangerous for fluid extraction.

In some embodiments, supercritical drying of amphiphilic polypeptide hydrogels wherein a supercritical fluid comprises carbon dioxide includes drying at a pressure between about 1200 psi and about 1800 psi. In some embodiments, supercritical drying occurs at pressures as low as 800 psi. In some embodiments, supercritical drying occurs at pressures as high as 5000 psi.

In some embodiments, supercritical drying of amphiphilic polypeptide hydrogels occurs at pressures of about 500 psi, about 600 psi, about 700 psi, about 800 psi, about 900 psi, about 1000 psi, about 1100 psi, about 1200 psi, about 1300 psi, about 1400 psi, about 1500 psi, about 1600 psi, about 1700 psi, about 1800 psi, about 1900 psi, about 2000 psi, about 2100 psi, about 2200 psi, about 2300 psi, about 2400 psi, about 2500 psi, about 2600 psi, about 2700 psi, about 2800 psi, about 2900 psi, about 3000 psi, about 3100 psi, about 3200 psi, about 3300 psi, about 3400 psi, about 3500 psi, about 3600 psi, about 3700 psi, about 3800 psi, about 3900 psi, about 4000 psi, about 4100 psi, about 4200 psi, about 4300 psi, about 4400 psi, about 4500 psi, about 4600 psi, about 4700 psi, about 4800 psi, about 49500 psi, or about 5000 psi.

Figure 4:
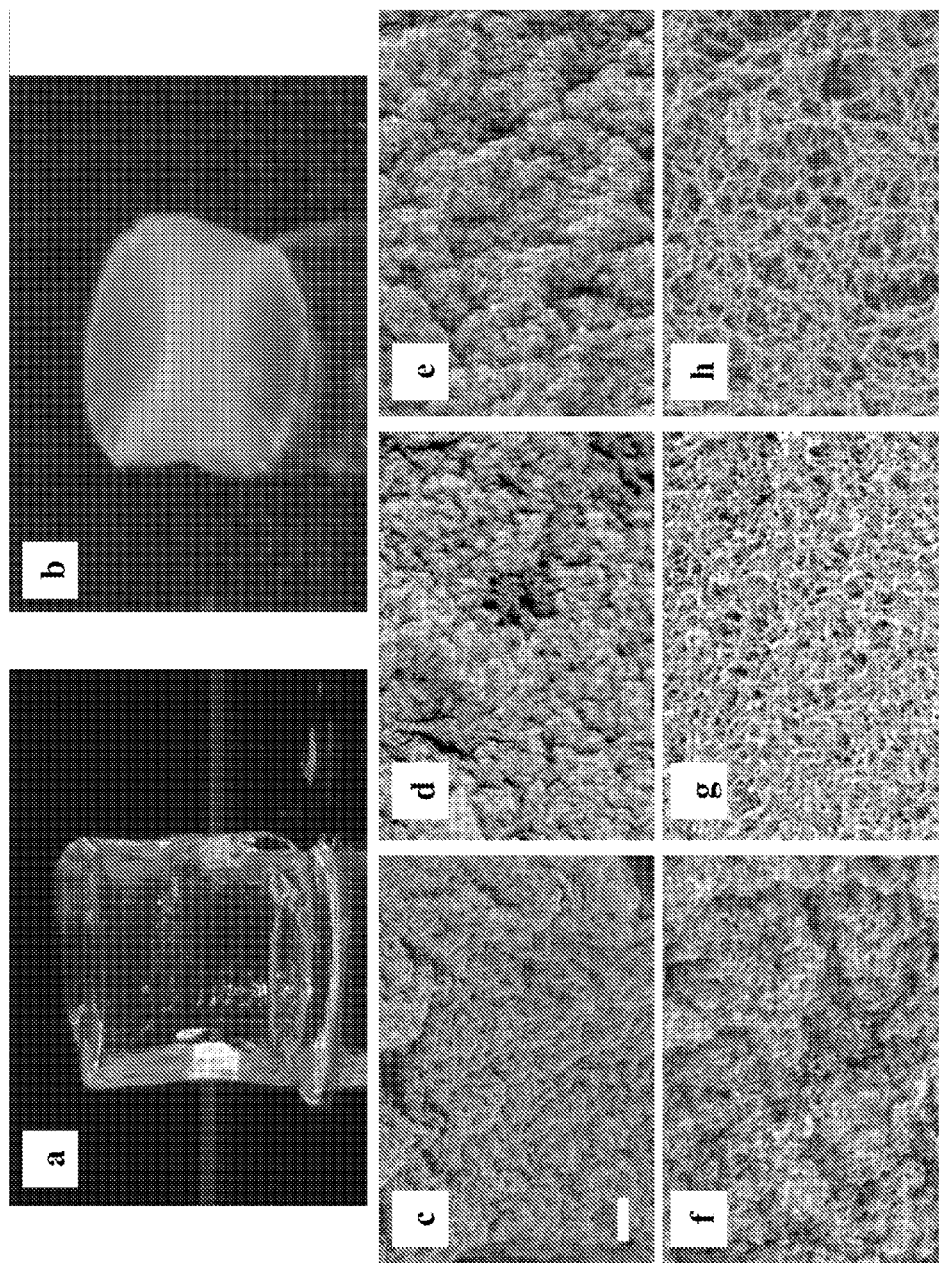
FIG. 4. shows effects of pressure on silk hydrogel.

FIG. 4 shows the effects of pressure on silk hydrogel. FIG. 4a shows an image of a silk fibroin hydrogel, which enables the fabrication of an optically clear material. FIG. 4b shows an image of a silk fibroin nanofibrillar material produced after supercritical drying of a silk fibroin hydrogel. FIG. 4c through FIG. 4h show the effects of $CO_2$ pressure on drying of silk hydrogels. A pressure vessel was kept at constant temperature (50° C.) and effluent rate (2 kg/hr) for varying pressures. Pore structure for dried hydrogels and nanofibrillar materials are shown for pressures: FIG. 4c 0 psi, FIG. 4d 200 psi, FIG. 4e 500 psi, FIG. 4f 750 psi, FIG. 4g 1000 psi, and FIG. 4h 1800 psi. Scale bar is 200 nm.

In some embodiments, methods including a step of providing an amphiphilic polypeptide hydrogel comprises providing a solution of about 100% ethanol mixed with platinum(II) meso-tetrakis(pentafluorophenyl)porphyrin (PtTFPP).

In some embodiments, methods of forming nanofibrillar material includes steps of introducing a functional moiety. In some embodiments, a functional moiety is incorporated in a step of providing the solution of the amphiphilic polypeptide. In some embodiments, a functional moiety comprises an enzymes or cells.

In some embodiments, methods of forming nanofibrillar materials of the present disclosure result in nanofibrillar materials with nanofibrils having an average diameter between about 2 nm and about 40 nm. In some embodiments, methods of forming nanofibrillar materials of the present disclosure result in nanofibrillar materials with nanofibrils having interconnected pores. In some embodiments, methods of forming nanofibrillar materials of the present disclosure result in interconnected pores having a majority of interconnected pores with a diameter between about 2 nm and about 100 nm. In some embodiments, methods of forming nanofibrillar materials of the present disclosure result in nanofibrillar materials characterized by a porosity of at least about 80%.

In some embodiments, methods of forming nanofibrillar materials of the present disclosure result in nanofibrillar materials further characterized by properties, including a bulk density that is less than about 75 kg/m$^3$, a compressive modulus between that is between about 50 kPa and about 300 kPa, and an optical transparency of between about 50% and about 75% at about 600 nm.

To further illustrate, in some embodiments, provided methods for producing nanofibrillar materials involve the following steps: (i) providing an amphiphilic peptide solution (typically characterized by having amorphous micellar structure of about 3-40 nm in size); (ii) inducing the formation of a peptide-based gel (i.e., hydrogel, which is typically transparent, amorphous micelles aggregate in crystalline nanoparticles with average diameter less than 100 nm, characterized by colloidal morphology, typically obtained through sol-gel transition); (iii) dehydrating in an organic solvent, such as methanol, ethanol, isopropanol, acetone, etc.; and, (iv) critical point drying (spinning of nanoparticles in nanofibers), so as to form nanofibrillar materials.

Alternatively, in some embodiments, provided methods for producing nanofibrillar materials involve the following steps: (i) providing freeze-dried amphiphilic peptides or proteins (e.g., 10-60 mb; typically a solid, amorphous material); (ii) preparing an organic solution such as HFIP-peptide solution (e.g., 0.5-7 wt %, which is typically a helically structured peptide micelle); (iii) critical point drying, so as to form nanofibrillar materials with very high mechanical properties in terms of compressive modulus and elastic modulus. Note that an extra step may be taken in the HFIP aerogel by going from HFIP peptide solution to alcohol, followed by critical point drying. This is expected to increase the mechanical properties.

Effect of SCCO$_2$ on Silk Fibroin Hydrogels

Supercritical drying with carbon dioxide (SCCO$_2$) is an environmentally benign alternative to fashion various biomaterials facilitating porosity, as well as processing thermally sensitive protein therapeutics. See M. L. Floren, S. Spilimbergo, A. Motta, and C. Migliaresi, Biomacromolecules, 2012, 13, 2060-2072, the entire contents of which are hereby incorporated by reference herein. The effect of supercritical drying with carbon dioxide on silk fibroin hydrogels was determined by drying at different pressures to determine changes in nanofiber formation. Previously reported results state that pressure perturbations can convert protein molecules into nanofibers, and under high pressure conditions silk experiences a change in polymer morphology. See S. Thomas and Y. Weimin, Advances in polymer processing, Woodhead Publishing Limited, 2009; see also S. G. Kazarian, Polym. Sci., 2000, 42, 78-101; see also O. S. Fleming and S. G. Kazarian, Supercritical Carbon Dioxide, Wiley-VCH Verlag GmbH & Co. KGaA, Weinheim, FRG, 2005, the entire contents of each of which is hereby incorporated by reference herein. The increase in fiber formation are associated with CO$_2$ molecules interacting with basic carbonyl groups in polymer molecules reducing chain-chain interactions and increasing polymer segment mobility. See S. G. Kazarian, Polym. Sci., 2000, 42, 78-101. As shown in FIG. 4a through FIG. 4h, scanning electron microscope (SEM) micrographs showed after exposing silk hydrogels to SCCO$_2$ drives assembly of silk submicron particles to nanofibers. The polymer nanofiber formation was evident by drying a silk hydrogel in hexamethyldisilazane (HMDS), which depicted the assembly of silk fibroin nanoparticles with morphological features less than 100 nm, as shown in FIG. 2c to the development of nanofibers at different drying pressure. As shown in FIG. 2h, SEM micrographs show a highly dense network of silk nanofibers with diameters between 10-20 nm with larger pore dimensions on the order of hundreds of nanometers when samples were dried above the critical point of CO$_2$.

The transformation from particle gel to a nanofiber structure is believed to be associated with changes in the protein regarding partial molar volumes, protein folding, and conformational transformations. See M. L. Floren, S. Spilimbergo, A. Motta, and C. Migliaresi, Biomacromolecules, 2012, 13, 2060-2072. This data is consistent with previously reported studies where silk fibroin nanofibers synthesis after SCCO$_2$ allowed for the formation of silk nanofibrillar materials, which were used as a controlled drug release system for ibuprofen. See M. A. Marin, R. R. Mallepally, and M. A. McHugh, J. Supercrit. Fluids, 2014, 91, 84-89, the entire contents of which is hereby incorporated by reference herein. By controlling the hydrogel formation and pressure during drying, we developed a fast and easy method to form relatively translucent, low bulk density, silk nanofibrillar materials where the gel formation was selected to maximize gel integrity and transparency. By modulating silk fibroin molecular weight (MW) during purification of raw fiber, silk solutions with an average MW of 100 kDa (proportional to 30 minute boiling time, see L. S. Wray, X. Hu, J. Gallego, I. Georgakoudi, F. G. Omenetto, D. Schmidt, and D. L. Kaplan, J. Biomed. Mater. Res. B. Appl. Biomater., 2011, 99, 89-101, the entire contents of which are hereby incorporated by reference herein) provided the ideal trade-off between transparency, strength, and bulk density. The associated pressure to induce nanofibrillar material formation also offers a significant function to alter the protein conformation.

Effect on Secondary Structure after SCCO$_2$

β-sheet features control the crystallinity of silk fibroin and modulate the degradability of the protein from hours to months and years. See Y. Wang, D. D. Rudym, A. Walsh, L. Abrahamsen, H.-J. Kim, H. S. Kim, C. Kirker-Head, and D. L. Kaplan, Biomaterials, 2008, 29, 3415-28; see also Y. Cao and B. Wang, Int. J. Mol. Sci., 2009, 10, 1514-24, the entire contents of both of which are hereby incorporated by reference herein. While not wishing to be bound to a theory, it is hypothesized that enhanced crystallinity corresponds to a more packed hydrophobic structure that decreases accessibility to proteolytic enzymes to cleavage sites in the protein. The control of crystallinity allows for the regulation of mechanical properties of the material as well as the investigation of nanofiber formation. To exploit the unique crystalline structure of silk fibrin based materials, β-sheet formation is typically controlled by introducing silk materials to alcohols (e.g. methanol and ethanol) see N. Rockwood, R. C. Preda, T. Yiicel, X. Wang, M. L. Lovett, and D. L. Kaplan, Nat. Protoc., 2011, 6, 1612-31, the entire contents of which are hereby incorporated by reference herein and dehydrated the sample in ethanol or methanol before supercritical drying in CO$_2$. As shown in FIG. 5a, attenuated total reflectance-Fourier transform infrared (ATR-FTIR) spectroscopy measurements verified the crystalline conformational change of silk fibroin after SCCO$_2$ drying by examining the amide I, II, and III absorption peaks (1750-750 cm$^{-1}$) of the protein attributed to the β-sheet features. See M. R. Nilsson, Methods, 2004, 34, 151-60; see also X. Hu, D. Kaplan, and P. Cebe, Macromolecules, 2006, 39, 6161-6170, the entire contents of both of which are hereby incorporated by reference herein. The amide I band occurs in the region between 1600 and 1700 cm$^{-1}$ and assignment of the peak at 1620 cm$^{-1}$ or lower wavenumbers are representative of nanofibers with strong hydrogen bonding. See M. R. Nilsson, Methods, 2004, 34, 151-60, the entire contents of which are hereby incorporated by reference herein.

Applications for Nanofibrillar Materials

Various types of aerogels are being developed with a wide range of commercial products and tools. In some embodiments, nanofibrillar materials described herein can be also used for a great number of applications. As provided above, these include, without limitation: biodegradable carrier materials, biomedical products, treatments, and/or therapies, biomaterials, bionanotechnology, biosensing, electronics, extracting agents, fillers, functional biomaterials, functional fibers (e.g. nanowires, scaffolds, etc.), gas sensing, nanovessels, optics, optogenetics, pharmaceutical products, treatments, and/or therapies, photonics, photonic devices, sensing applications, textiles, thermal insulating catalysts, thermal insulating materials, and/or tissue engineering applications.

In some embodiments, with respect to nanofibrillar materials produced from structural proteins such as silk and cashmere and wool proteins (e.g., keratins), since these materials are known as textiles, changing its form can make it better as an insulating material in clothing or any other thermal applications. In some embodiments, nanofibrillar materials can also be used as biodegradable carrier materials for active substances such has fungicides, herbicides, and pesticides. In some embodiments, with respect to nanofibrillar materials can also be used as fillers in liquids such as paints and varnishes.

In some embodiments, nanofibrillar materials as described herein are also useful in biomedical and pharmaceutical contexts. Functional biomaterials are important in the field of bionanotechnology because of the number of attractive properties including self-assembly, strength, and stability. For example, in some embodiments, nanofibrillar materials can be used as fillers for drug delivery. In some embodiments, nanofibrillar materials may also be used as adsorbent materials. In some embodiments, due to its high surface area, nanofibrillar materials may also be ideal catalysts. In some embodiments, with respect to porosity nanofibrillar materials may also be ideal for nano vessels or for extracting agents.

In some embodiments, biological entities (e.g. cells or enzymes) and chemical sensitive molecules can capitalize on nanofibrillar materials for three-dimensional microenvironments to mimic extracellular matrices (see M. P. Lutolf and J. A. Hubbell, Nat. Biotechnol., 2005, 23, 47-55, the entire contents of which are hereby incorporated by reference herein) and sensing applications, to generate biological systems or to build novel optical interfaces. Nanofibers and high porosity are the main characteristics of aerogels which have been shown as platforms for chemical sensing see F. Fischer, A. Rigacci, R. Pirard, S. Berthon-Fabry, and P. Achard, Polymer (Guildf)., 2006, 47, 7636-7645; see also N. Hüsing and U. Schubert, Angew. Chemie Int. Ed., 1998, 37, 22-45; see also H. D. Gesser and P. C. Goswami, Chem. Rev, 1989, 89, 765, the entire contents of each of which are hereby incorporated by reference herein. The possibility of combining nanofiber formation with the well-established mechanical, biochemical, and biological properties of silk fibroin would create a new groundwork for this material format, producing highly porous constructs with high surface area functionalities with enhanced optical and photonic applications.

Incorporation of Biologics

In some embodiments, control of silk concentration combined with specific hydrogel synthesis were optimized to improve transparency of nanofibrillar materials while stabilizing activity of enzymes to preserve their biological function.

Aerogels are among the most versatile materials available for technical applications including gas sensing and catalyst supports, and adding biologically active enzymes to aerogels can be imperative to make functional materials with various dopants that are stabilized by silk fibroin. See L. W. Hrubesh, J. Non. Cryst. Solids, 1998, 225, 335-342, the entire contents of both of which are hereby incorporated by reference herein. In some embodiments, as a preliminary evaluation for stabilization of active biological compounds in silk fibroin nanofibrillar materials, horseradish peroxidase (HRP) was mixed with silk fibroin solution prior to hydrogel and nanofibrillar material formation.

Figure 9:
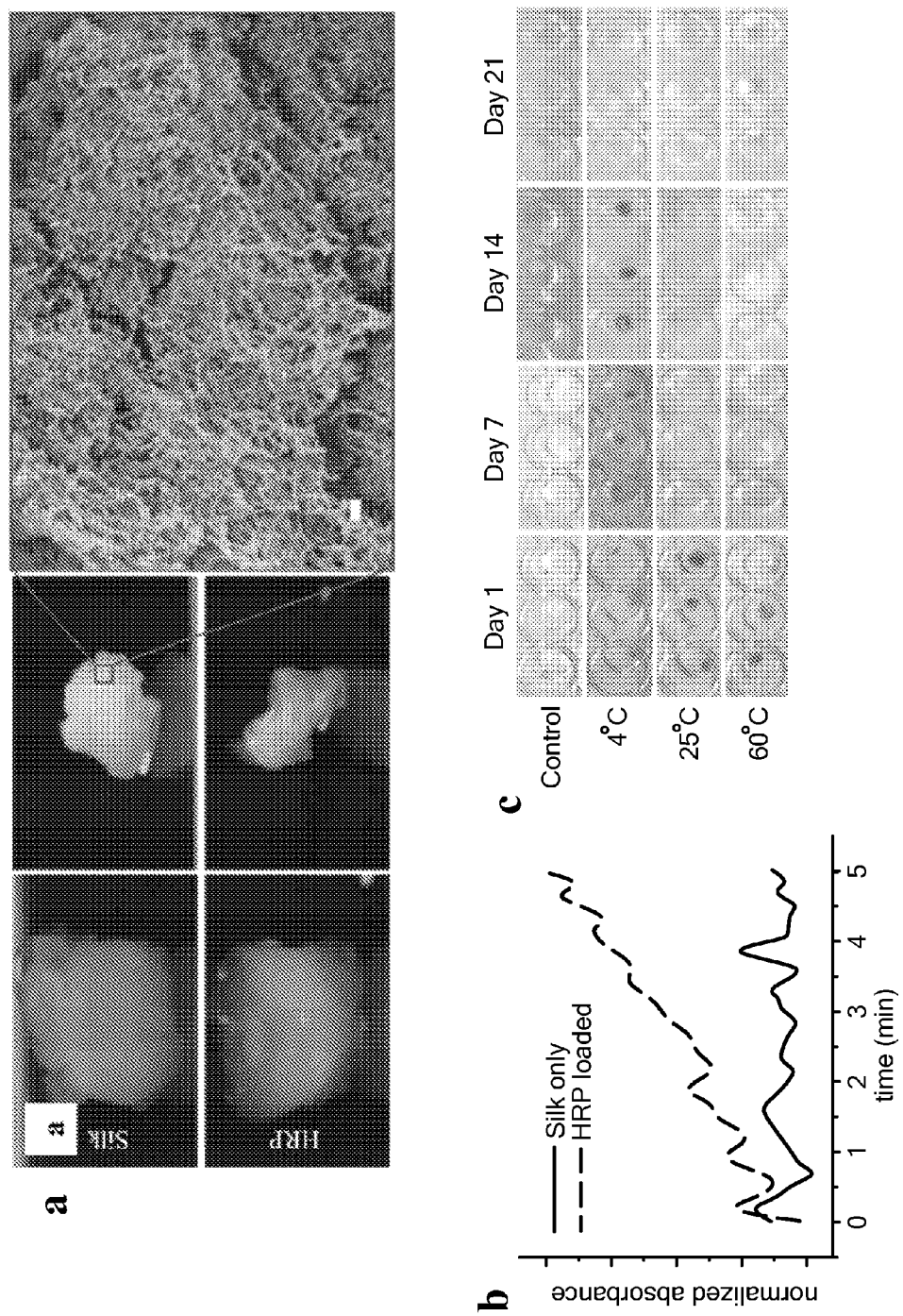
FIG. 9. shows biological entrapment of enzymes in silk fibroin nanofibrillar materials.

FIG. 9 shows biological entrapment of enzymes in silk fibroin nanofibrillar materials. Enzymatic stability of horse radish peroxidase (HRP) and glucose oxidase (GOx) in silk fibroin nanofibrillar materials. FIG. 9a shows images of silk fibroin nanofibrillar materials with and without HRP in the presence of TMB. In the presence of HRP, TMB follows a reaction changing from a transparent liquid to a blue-green liquid. SEM image of twice critically point dried nanofibrillar materials after exposure to a liquid solvent preventing total collapse of the pore structure. Scale bar is 200 nm. FIG. 9b shows TMB reaction product absorbance measured at 370 nm for silk and HRP loaded silk fibroin nanofibrillar materials. FIG. 9c shows images of HRP loaded silk fibroin nanofibrillar materials stored at different temperatures in the TMB solution at day 1, day 7, day 14, and day 21 and different storage temperatures.

As shown in FIG. 9a and FIG. 9b, microplate reads were taken of nanofibrillar material samples at days 7, 14, and 21 after the reduction of 3,3',5,5'-tetramethylbenzidine (TMB) liquid solution which changes from colorless to a bluish-green color in the presence of HRP. Silk fibroin nanofibrillar material samples and HRP liquid samples were stored at 4° C., 25° C., and 60° C. to monitor the effectiveness of silk nanofibrillar material stabilization. As shown in FIG. 9c, at day 14, there is a visible color change in TMB as shown by the images after 10 minutes at 4° C. and 25° C. compared to the 60° C. sample, which relates to the measured HRP activity. As shown in FIG. 9a (insert), due to the liquid nature of the samples, collapse of a structure was apparent. However, SEM analysis of nanofibrillar material samples supercritically dried after wetting shows nanofibrillar material structure and partial porosity remain making theses samples conducive as liquid sensors and active filtration systems for possible biological samples.

In some embodiments, enzyme stabilized silk nanofibrillar materials can find use as active filtration systems where liquid samples can be cleared by functionalized silk nanofibrillar material. As a proof of principle, silk fibroin nanofibrillar materials were loaded with glucose oxidase (GOx) to evaluate stabilization and activity as high porosity materials.

Figure 10:
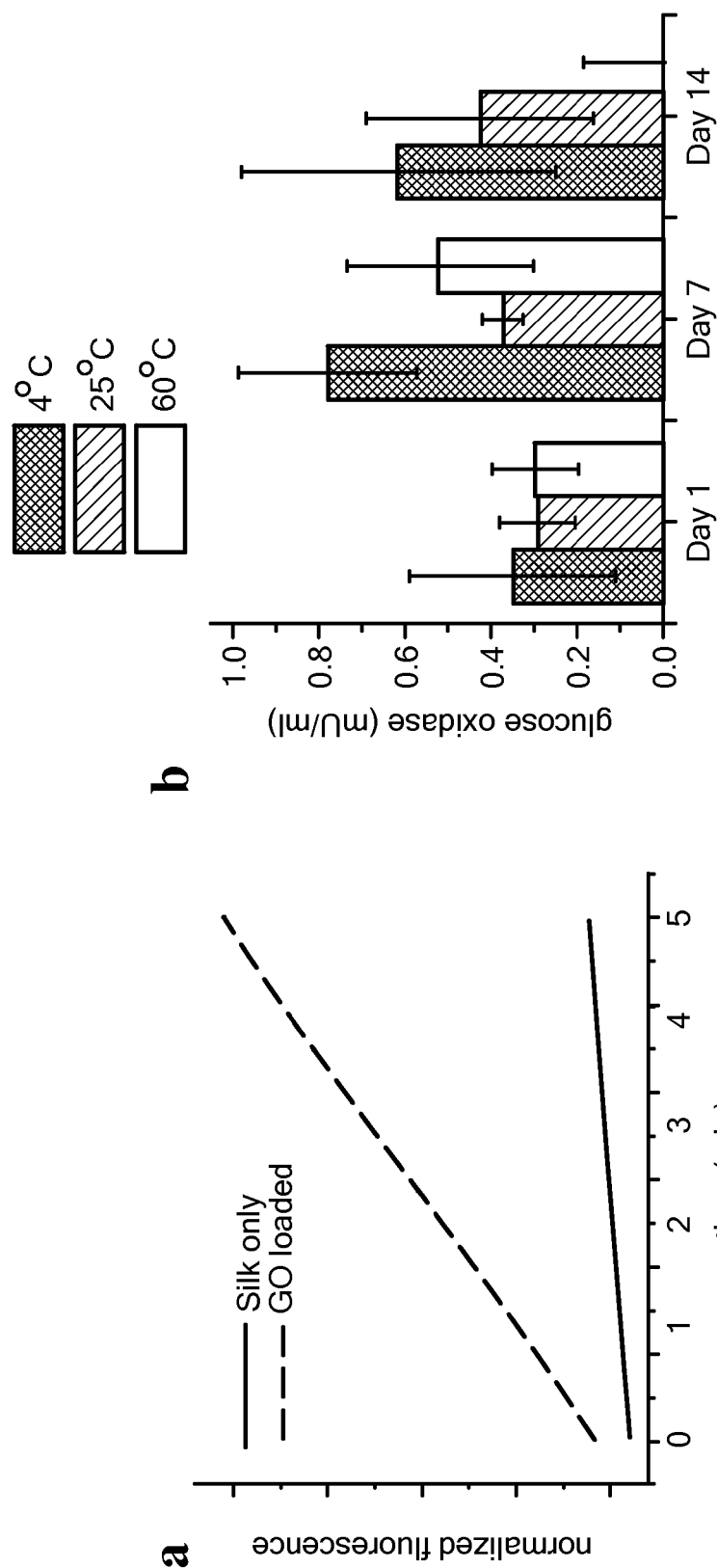
FIG. 10. shows stability of glucose oxidase in silk fibroin nanofibrillar materials at different storage temperatures.

FIG. 10 shows stability of glucose oxidase in silk fibroin nanofibrillar materials at different storage temperatures. FIG. 10a shows unloaded silk nanofibrillar materials and glucose oxidase liquid solution were used as controls. FIG. 10b shows Amplex®Red fluorescent reaction product in the presence of active GOx measured with Ex=530 nm and Em=590 nm for silk and GOx loaded silk fibroin nanofibrillar materials. FIG. 10b shows measured activity of glucose oxidase at day 1, day 7, and day 14 at varying storage temperatures. FIG. 10b shows Amplex® Red assay on GOx loaded silk fibroin nanofibrillar materials showed activity at 4° C. and 25° C. Activity of glucose oxidase decreases 0 at day 14 for 60° C. samples signifying a loss of activity and function. These results show the stabilizing properties of silk fibroin nanofibrillar materials as potential liquid sensing materials that maintain specific function at varying storage conditions over time.

As a preliminary evaluation of cytotoxicity, human dermal fibroblasts were cultured up to 10 days on a surface of silk fibroin nanofibrillar materials and imaged using confocal laser scanning microscopy.

Figure 8:
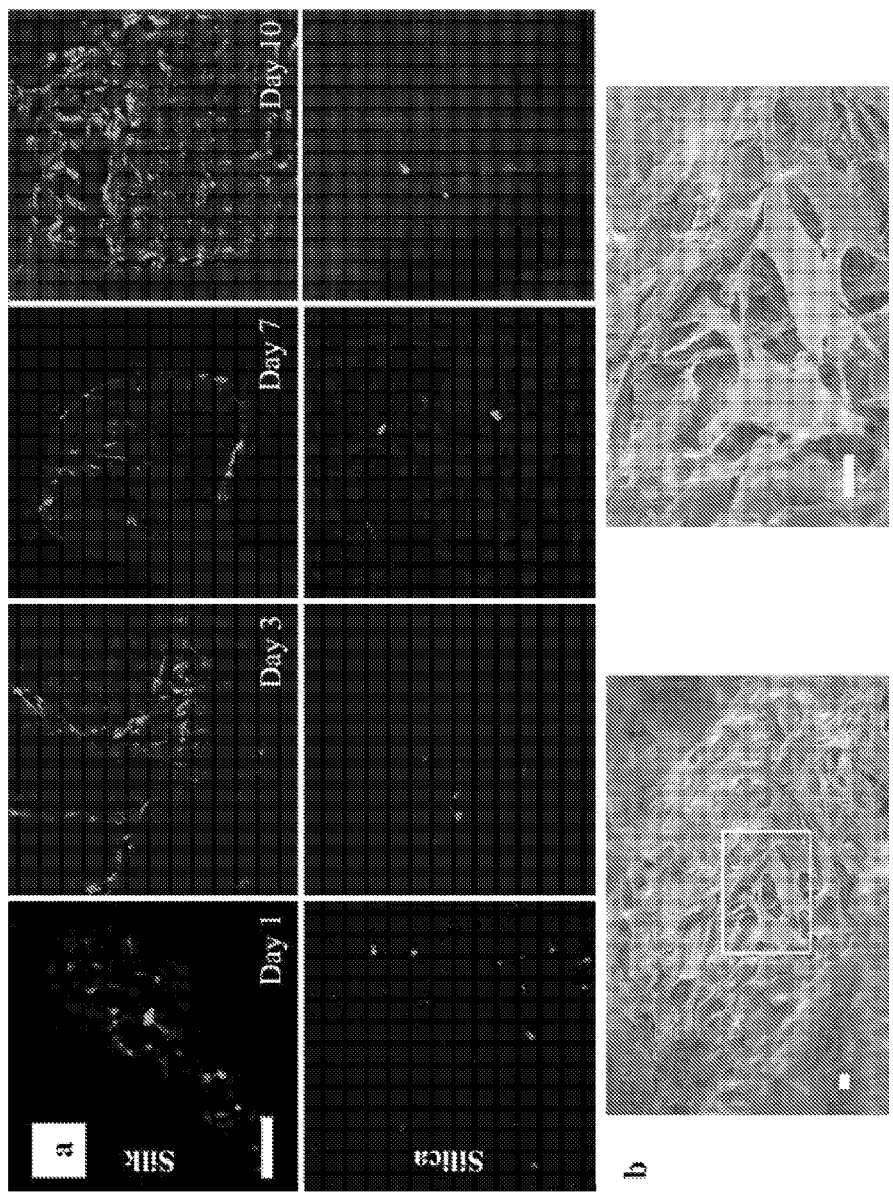
FIG. 8. shows biological characterization of silk fibroin nanofibrillar materials.

FIG. 8 shows biological characterization of silk fibroin nanofibrillar materials. Human fibroblasts were culture on transparent silk fibroin nanofibrillar materials. Silica aerogels were used as control. FIG. 8a shows confocal microscopy of live/dead assay on fibroblasts cultured on the surface of silk fibroin and silica aerogels at day 1, day 3, day 7, and day 10. Cells were viable and proliferated during the culture time considered. Scale bar is 375 µm. FIG. 8b shows SEM micrographs cellular gels at day 10 were collected to investigate cell morphology and production of extracellular matrix. The enlarged micrograph shows close up of extracellular matrix deposition. Scale bar is 20 µm.

As shown in FIG. 8, fibroblasts were stained at days 1, 3, 7, and 10 with calcein-AM fluorescein and EtBr-1 deoxyribonucleic acid binding (Live/Dead® assay). Fibroblasts were viable up to 10 days (green) and compared to silica aerogels as a control. In addition, SEM analysis of seeded nanofibrillar materials showed cell coverage at day 10. Combined with the mechanical and porosity of silk nanofibrillar materials, further studies can be examined to use nanofibrillar materials as a tissue engineered material.

Oxygen Sensing

Low density and high porosity are two characteristics that are important in gas sensing materials since the gas can easily fill the material pores and contact the solid network/skeleton. In some embodiments, nanostructures are an important characteristic where silk in a nanofiber format has shown sensing potential.

For sensing applications, the film format of silk fibroin has been used due to its preservation of heat-labile biomolecules, transparency, and robust mechanical properties allowing the fabrication of photonic devices with novel features interfaced with biology. See D. N. Rockwood, R. C. Preda, T. Yiicel, X. Wang, M. L. Lovett, and D. L. Kaplan, Nat. Protoc., 2011, 6, 1612-31, see also B. D. Lawrence, M. Cronin-Golomb, I. Georgakoudi, D. L. Kaplan, and F. G. Omenetto, Biomacromolecules, 2008, 9, 1214-20, the entire contents of both of which are hereby incorporated by reference herein. Other common formats that provide nanodimensions, such as electrospun mats, are characterized by high optical loss due to scattering making them less ideal for sensing platforms. See S. Zarkoob, D. H. Reneker, R. K. Eby, S. D. Hudson, D. Ertley, and W. W. Adams, in American Chemical Society, Polymer Preprints, Division of Polymer Chemistry, ACS, 1998, vol. 39, pp. 244-245; see also N. Bhardwaj and S. C. Kundu, Biotechnol. Adv., 2010, 28, 325-347, see also A. Frenot and I. S. Chronakis, Curr. Opin. Colloid Interface Sci., 2003, 8, 64-75, the entire contents of each of which are hereby incorporated by reference herein.

In some embodiments, due to their high porosity, silk nanofibrillar materials are ideal for gas sensing because their surface area allows gas molecules to contact more often with a physical skeletal structure. Aerogel sensors are used for multiple detection purposes including monitoring gas-phase species to determine air quality, assessing pH, or measuring ion concentration in water samples. See M. Aegerter, N. Leventis, and M. Koebel, Eds., Aerogel Handbook, Springer, New York, 2011, the entire contents of which are hereby incorporated by reference herein. As a possible gas sensing device, silk fibroin nanofibrillar materials were loaded with platinum(II) meso-tetrakis(pentafluorophenyl) porphyrin (PtTFPP) to evaluate them as a fluorescent sensor based on die high surface area.

Figure 6:
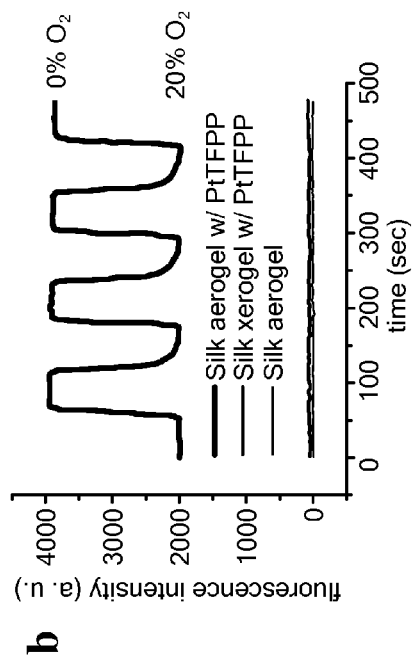
FIG. 6. shows silk nanofibrillar materials as gas sensing materials.
Figure 6:
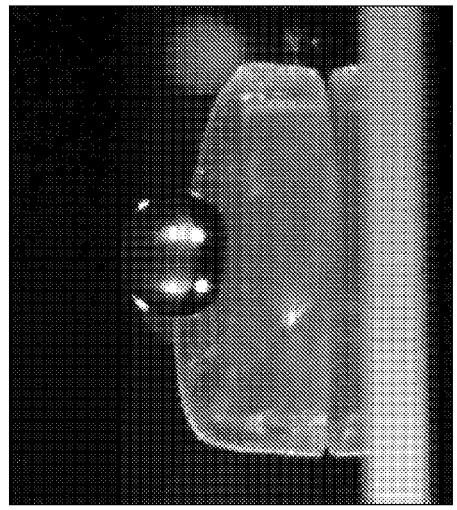
Figure 6:
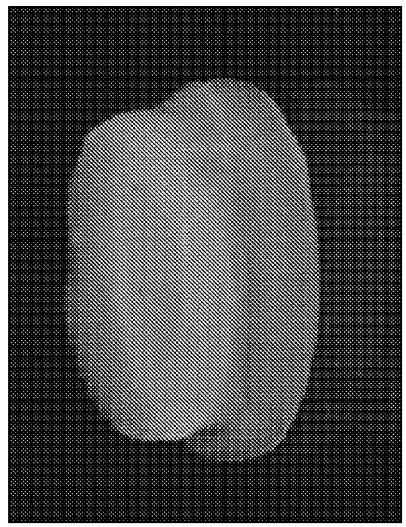
Figure 6:
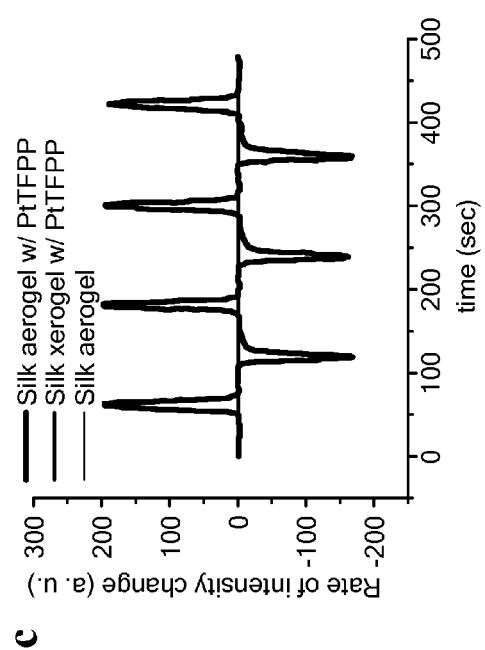

FIG. 6 shows silk nanofibrillar materials as gas sensing materials and in particular, PtTFPP loaded silk nanofibrillar materials for oxygen sensing applications. FIG. 6a shows an image of a silk fibroin nanofibrillar material loaded with PtTFPP. FIG. 6b shows fluorescent measurements of silk fibroin nanofibrillar materials loaded with PtTFPP, silk xerogels loaded with PtTFPP, and silk nanofibrillar materials without PtTFPP. Nitrogen gas was cycled every minute during measuring starting at ambient oxygen levels of 20% and finishing at 0% during flushing the chamber with nitrogen. FIG. 6c shows derivative of fluorescent intensity vs. time to show the response of oxygen sensitivity during oxygen measurements. FIG. 6d shows an image of hydrophobic silk nanofibrillar materials with a contact angle of ~110°.

Optical oxygen sensing relies upon collisional quenching of molecular oxygen with a fluorophore (see M. R. Ayers and A. J. Hunt, J. Non. Cryst. Solids, 1998, 225, 343-347, the entire contents of which are hereby incorporated by reference herein) causing a non-radiative relaxation reducing the emission intensity.

Figure 11:
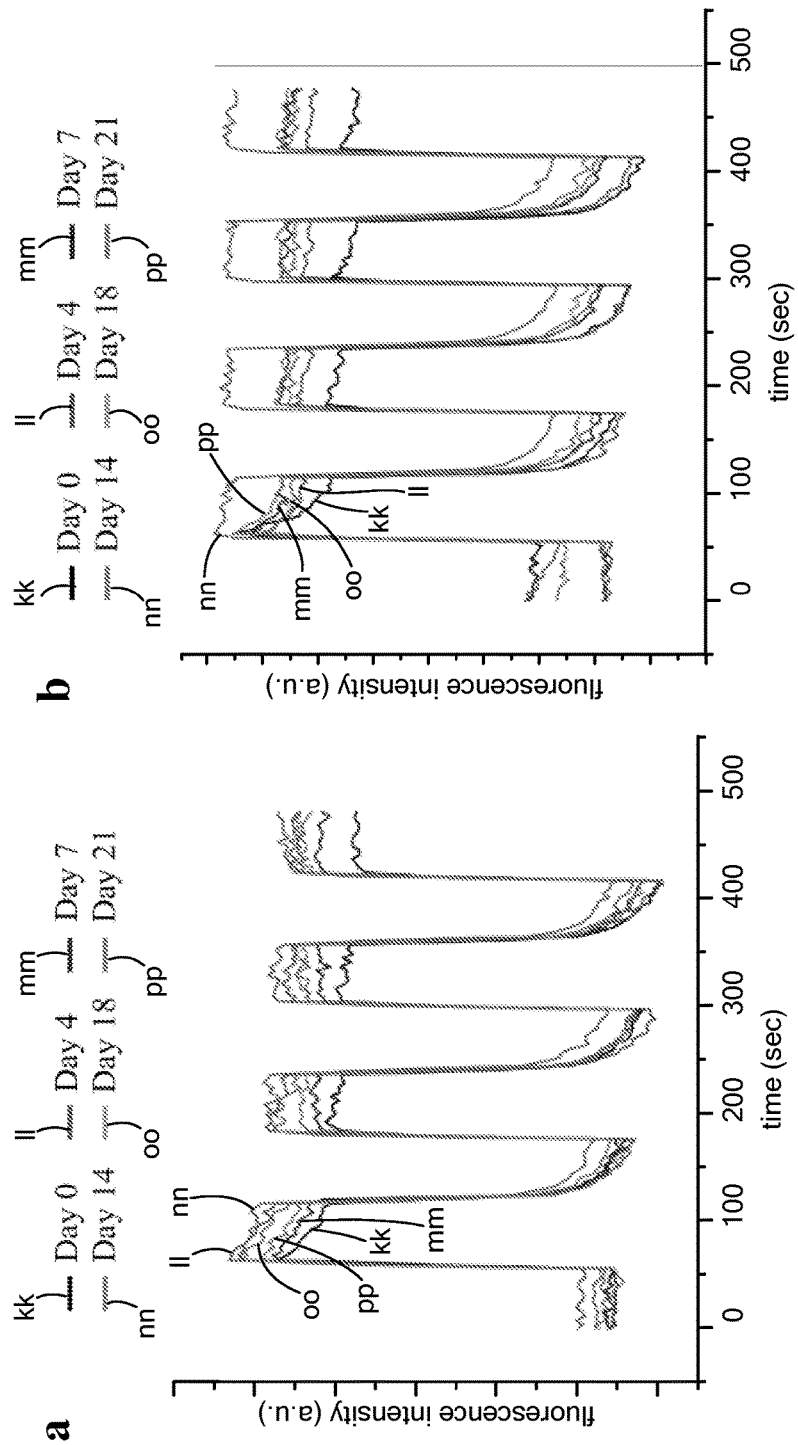
FIG. 11. shows stability of PtTFPP in silk fibroin nanofibrillar materials at different temperatures.
Figure 11:
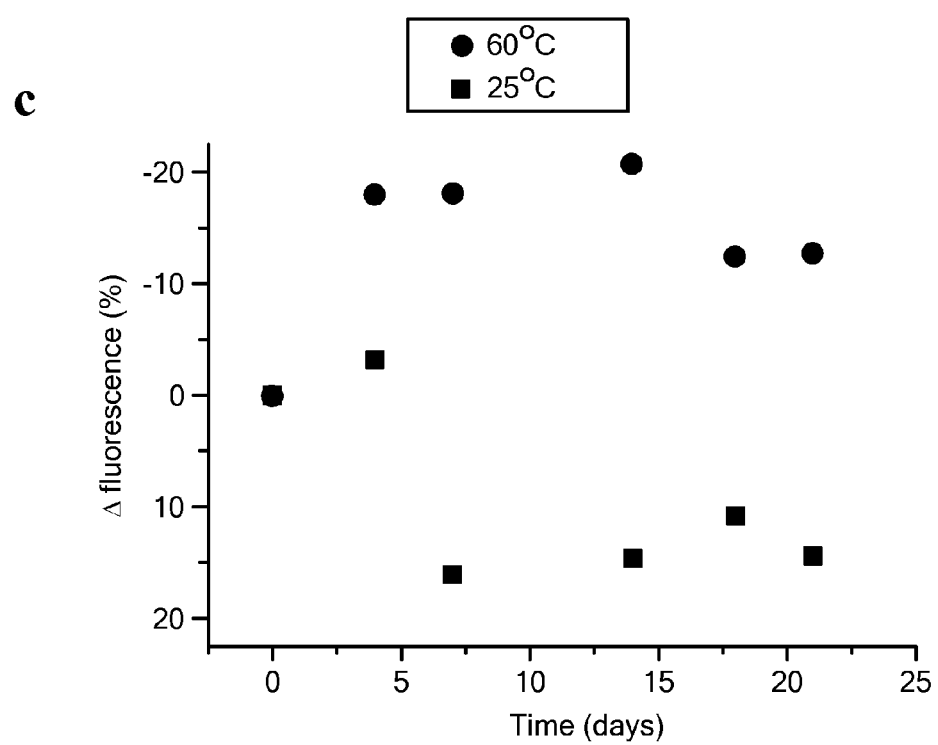

FIG. 11 shows stability of PtTFPP in silk fibroin nanofibrillar materials at different temperatures. An effect of temperature on silk fibroin nanofibrillar materials as measured by fluorescence of representative samples at FIG. 11a for 25° C. and FIG. 11b for 60° C. As shown in FIG. 11a and FIG. 11b, a combination of oxygen saturation and storage conditions at 25° C. and 60° C. were used to examine stability regarding an effect of temperature on the porphyrin molecule. As shown in FIG. 11a and FIG. 11b, repeatability of sensors at oxygen concentrations of 0% and 20% were examined which showed no appreciable difference after repeated and cyclic use.

As shown in FIG. 11c, to confirm the sensitivity of samples, derivative of the fluorescence intensity was compared during each cycle of 0% oxygen saturation and 20% oxygen saturation showing there was no change in fluorescence rate. As shown in FIG. 11c, after 21 days in storage at 25° C. and 60° C., there was an observed difference in fluorescent intensity of nanofibrillar samples. Silk nanofibrillar materials kept at a higher temperature showed a larger change in fluorescence at 0% oxygen saturation and 20% oxygen saturation up to 21 days compared to nanofibrillar materials stored at 25° C. A decrease in change in fluorescence observed at higher temperatures is hypothesized to occur due to damage of a skeletal structure from changes of an ambient humidity content at 25° C. compared to drier 60° C. condition. To prevent damage due to liquid or gaseous water, these nanofibrillar materials have the capability to become hydrophobic with a contact angle of ~110° by conditioning samples in a saturated HMDS gas environment for 24 hours. FIG. 11c therefore shows a difference in 0% oxygen saturation fluorescence and 20% oxygen saturation fluorescence of individual silk fibroin nanofibrillar materials compared to the initial saturation difference. The negative value associated with 60° C. nanofibrillar materials samples signifies there is an increase in the difference between 0% oxygen saturation fluorescence and 20% oxygen saturation fluorescence compared to nanofibrillar material samples stored at 25° C.

Amphiphilic Polypeptides

In some embodiments, a polymer is natural or synthetic. In some embodiments, a polymer comprises one or more polypeptides or proteins. In some embodiments, degradable polymers known in the art include, for example, certain polyesters, polyanhydrides, polycaptolactone, polyorthoesters, polyphosphazenes, polyphosphoesters, certain polyhydroxyacids, polypropylfumerates, polycaprolactones, polyamides, poly(amino acids), polyacetals, polyethers, biodegradable polycyanoacrylates, biodegradable polyurethanes, poly(glycerol sebacates), elastomeric poly(glycerol sebacates polysaccharides), polypyrrole, polyanilines, polythiophene, polystyrene, polyesters, polyureas, poly(ethylene vinyl acetate), polypropylene, polymethacrylate, polyethylene, polycarbonates, poly(ethylene oxide), polysaccharides, co-polymers, and combinations thereof. For example, specific biodegradable polymers that may be used include but are not limited to polylysine (e.g., poly(L-lysine) ("PLL")), poly(lactic acid) ("PLA"), poly(glycolic acid) ("PGA"), polylactic acid/poly(glycolide-colactide) copolymer ("PLGA"), poly(caprolactone) ("PCL"), poly(lactide-co-glycolide) ("PLG"), poly(lactide-co-caprolactone) ("PLC"), poly(glycolide-co-caprolactone) ("PGC"), poly(styrene sulfonate) ("SPS"), poly(acrylic acid) ("PAA"), linear poly(ethylene imine) ("LPEI"), poly(diallyldimethyl ammonium chloride) ("PDAC"), and poly(allylamine hydrochloride) ("PAH"). Another exemplary degradable polymer is poly(beta-amino esters), which may be suitable for use in accordance with the present application. Those skilled in the art will recognize that this is an exemplary, not comprehensive, list of polymers.

In some embodiments, nanofibrillar materials described herein comprise an amino acid sequence of polypeptides selected from the following list: fibroins, actins, collagens, catenins, claudins, coilins, elastins, elaunins, extensins, fibrillins, lamins, laminins, keratins, tublins, viral structural proteins, zein proteins (seed storage protein) and any combinations thereof.

Although different species of silk-producing organisms, and different types of silk, have different amino acid compositions, various fibroin proteins share certain structural features. A general trend in silk fibroin structure is a sequence of amino acids that is characterized by usually alternating glycine and alanine, or alanine alone. Such configuration allows fibroin molecules to self-assemble into a beta-sheet conformation. These "Ala-rich" and "Gly-rich" hydrophobic blocks are typically separated by segments of amino acids with bulky side-groups (e.g., hydrophilic spacers).

Silks

In some embodiments, a polymer is silk. Silk is a natural protein fiber produced in a specialized gland of certain organisms. Silk production in organisms is especially common in the Hymenoptera (bees, wasps, and ants), and is sometimes used in nest construction. Other types of arthropod also produce silk, most notably various arachnids such as spiders (e.g., spider silk). Silk fibers generated by insects and spiders represent the strongest natural fibers known and rival even synthetic high performance fibers.

Silk has been a highly desired and widely used textile since its first appearance in ancient China (see Elisseeff, "The Silk Roads: Highways of Culture and Commerce," Berghahn Books/UNESCO, New York (2000); see also Vainker, "Chinese Silk: A Cultural History," Rutgers University Press, Piscataway, N.J. (2004)). Glossy and smooth, silk is favored by not only fashion designers but also tissue engineers because it is mechanically tough but degrades harmlessly inside the body, offering new opportunities as a highly robust and biocompatible material substrate (see Altman et al., Biomaterials, 24: 401 (2003); see also Sashina et al., Russ. J. Appl. Chem., 79: 869 (2006)).

Silk is naturally produced by various species, including, without limitation: *Antheraea mylitta; Antheraea pernyi; Antheraea yamamai; Galleria mellonella; Bombyx mori; Bombyx mandarina; Galleria mellonella; Nephila clavipes; Nephila senegalensis; Gasteracantha mammosa; Argiope aurantia; Araneus diadematus; Latrodectus geometricus; Araneus bicentenarius; Tetragnatha versicolor; Araneus ventricosus; Dolomedes tenebrosus; Euagrus chisoseus; Plectreurys tristis; Argiope trifasciata*; and *Nephila madagascariensis*.

In general, silk for use in accordance with the present disclosure may be produced by any such organism, or may be prepared through an artificial process, for example, involving genetic engineering of cells or organisms to produce a silk protein and/or chemical synthesis. In some embodiments of the present disclosure, silk is produced by the silkworm, *Bombyx mori*.

As is known in the art, silks are modular in design, with large internal repeats flanked by shorter (~100 amino acid) terminal domains (N and C termini). Naturally-occurring silks have high molecular weight (200 to 350 kDa or higher) with transcripts of 10,000 base pairs and higher and >3000 amino acids (reviewed in Omenatto and Kaplan (2010) Science 329: 528-531). The larger modular domains are interrupted with relatively short spacers with hydrophobic charge groups in the case of silkworm silk. N- and C-termini are involved in the assembly and processing of silks, including pH control of assembly. The N- and C-termini are highly conserved, in spite of their relatively small size compared with the internal modules. Table 1, below, provides an exemplary list of silk-producing species and silk proteins:

TABLE 1

An exemplary list of silk-producing species and silk proteins (adopted from Bini et al. (2003), J. Mol. Biol. 335(1): 27-40).

| Accession | Species | Producing gland | Protein |
|---|---|---|---|
| A. Silkworms | | | |
| AAN28165 | Antheraea mylitta | Salivary | Fibroin |
| AAC32606 | Antheraea pernyi | Salivary | Fibroin |
| AAK83145 | Antheraea yamamai | Salivary | Fibroin |
| AAG10393 | Galleria mellonella | Salivary | Heavy-chain fibroin (N-terminal) |
| AAG10394 | Galleria mellonella | Salivary | Heavy-chain fibroin (C-terminal) |
| P05790 | Bombyx mori | Salivary | Fibroin heavy chain precursor, Fib-H, H-fibroin |
| CAA27612 | Bombyx mandarina | Salivary | Fibroin |
| Q26427 | Galleria mellonella | Salivary | Fibroin light chain precursor, Fib-L, L-fibroin, PG-1 |
| P21828 | Bombyx mori | Salivary | Fibroin light chain precursor, Fib-L, L-fibroin |

TABLE 1-continued

An exemplary list of silk-producing species and silk proteins (adopted from Bini et al. (2003), J. Mol. Biol. 335(1): 27-40).

| Accession | Species | Producing gland | Protein |
|---|---|---|---|
| B. Spiders | | | |
| P19837 | Nephila clavipes | Major ampullate | Spidroin 1, dragline silk fibroin 1 |
| P46804 | Nephila clavipes | Major ampullate | Spidroin 2, dragline silk fibroin 2 |
| AAK30609 | Nephila senegalensis | Major ampullate | Spidroin 2 |
| AAK30601 | Gasteracantha mammosa | Major ampullate | Spidroin 2 |
| AAK30592 | Argiope aurantia | Major ampullate | Spidroin 2 |
| AAC47011 | Araneus diadematus | Major ampullate | Fibroin-4, ADF-4 |
| AAK30604 | Latrodectus geometricus | Major ampullate | Spidroin 2 |
| AAC04503 | Araneus bicentenarius | Major ampullate | Spidroin 2 |
| AAK30615 | Tetragnatha versicolor | Major ampullate | Spidroin 1 |
| AAN85280 | Araneus ventricosus | Major ampullate | Dragline silk protein-1 |
| AAN85281 | Araneus ventricosus | Major ampullate | Dragline silk protein-2 |
| AAC14589 | Nephila clavipes | Minor ampullate | MiSp1 silk protein |
| AAK30598 | Dolomedes tenebrosus | Ampullate | Fibroin 1 |
| AAK30599 | Dolomedes tenebrosus | Ampullate | Fibroin 2 |
| AAK30600 | Euagrus chisoseus | Combined | Fibroin 1 |
| AAK30610 | Plectreurys tristis | Larger ampule-shaped | Fibroin 1 |
| AAK30611 | Plectreurys tristis | Larger ampule-shaped | Fibroin 2 |
| AAK30612 | Plectreurys tristis | Larger ampule-shaped | Fibroin 3 |
| AAK30613 | Plectreurys tristis | Larger ampule-shaped | Fibroin 4 |
| AAK30593 | Argiope trifasciata | Flagelliform | Silk protein |
| AAF36091 | Nephila madagascariensis | Flagelliform | Fibroin, silk protein (N-terminal) |
| AAF36092 | Nephila madagascariensis | Flagelliform | Silk protein (C-terminal) |
| AAC38846 | Nephila clavipes | Flagelliform | Fibroin, silk protein (N-terminal) |
| AAC38847 | Nephila clavipes | Flagelliform | Silk protein (C-terminal) |

Silk Fibroin

Fibroin is a type of structural protein produced by certain spider and insect species that produce silk. Cocoon silk produced by the silkworm, Bombyx mori, is of particular interest because it offers low-cost, bulk-scale production suitable for a number of commercial applications, such as textile.

Silkworm cocoon silk contains two structural proteins, the fibroin heavy chain (~350 kDa) and the fibroin light chain (~25 kDa), which are associated with a family of non-structural proteins termed sericin, which glue the fibroin brings together in forming the cocoon. The heavy and light chains of fibroin are linked by a disulfide bond at the C-terminus of the two subunits (see Takei, F., Kikuchi, Y., Kikuchi, A., Mizuno, S. and Shimura, K. (1987) 105 J. Cell Biol., 175-180; see also Tanaka, K., Mori, K. and Mizuno, S. 114 J. Biochem. (Tokyo), 1-4 (1993); Tanaka, K., Kajiyama, N., Ishikura, K., Waga, S., Kikuchi, A., Ohtomo, K., Takagi, T. and Mizuno, S., 1432 Biochim. Biophys. Acta., 92-103 (1999); Y Kikuchi, K Mori, S Suzuki, K Yamaguchi and S Mizuno, "Structure of the Bombyx mori fibroin light-chain-encoding gene: upstream sequence elements common to the light and heavy chain," 110 Gene, 151-158 (1992)). The sericins are a high molecular weight, soluble glycoprotein constituent of silk which gives the stickiness to the material. These glycoproteins are hydrophilic and can be easily removed from cocoons by boiling in water.

As used herein, the term "silk fibroin" refers to silk fibroin protein, whether produced by silkworm, spider, or other insect, or otherwise generated (Lucas et al., 13 Adv. Protein Chem., 107-242 (1958)). In some embodiments, silk fibroin is obtained from a solution containing a dissolved silkworm silk or spider silk. For example, in some embodiments, silkworm silk fibroins are obtained, from the cocoon of Bombyx mori. In some embodiments, spider silk fibroins are obtained, for example, from Nephila clavipes. In the alternative, in some embodiments, silk fibroins suitable for use in the invention are obtained from a solution containing a genetically engineered silk harvested from bacteria, yeast, mammalian cells, transgenic animals or transgenic plants. See, e.g., WO 97/08315 and U.S. Pat. No. 5,245,012, each of which is incorporated herein as reference in its entirety.

Thus, in some embodiments, a silk solution is used to fabricate compositions of the present disclosure contain fibroin proteins, essentially free of sericins. In some embodiments, silk solutions used to fabricate various compositions of the present disclosure contain the heavy chain of fibroin, but are essentially free of other proteins. In other embodiments, silk solutions used to fabricate various compositions of the present disclosure contain both the heavy and light chains of fibroin, but are essentially free of other proteins. In certain embodiments, silk solutions used to fabricate various compositions of the present disclosure comprise both a heavy and a light chain of silk fibroin; in some such embodiments, the heavy chain and the light chain of silk fibroin are linked via at least one disulfide bond. In some embodiments where the heavy and light chains of fibroin are present, they are linked via one, two, three or more disulfide bonds. Although different species of silk-producing organisms, and different types of silk, have different amino acid compositions, various fibroin proteins share certain structural features. A general trend in silk fibroin structure is a sequence of amino acids that is characterized by usually alternating glycine and alanine, or alanine alone. Such configuration allows fibroin molecules to self-assemble into a beta-sheet conformation. These "Alanine-rich" hydrophobic blocks are typically separated by segments of amino acids with bulky side-groups (e.g., hydrophilic spacers).

Silk materials explicitly exemplified herein were typically prepared from material spun by silkworm, Bombyx mori. Typically, cocoons are boiled in an aqueous solution of 0.02 M $Na_2CO_3$, then rinsed thoroughly with water to extract the glue-like sericin proteins. Extracted silk is then dissolved in a solvent, for example, LiBr (such as 9.3 M) solution at room temperature. A resulting silk fibroin solution can then be further processed for a variety of applications as described elsewhere herein.

Amphiphilic Fibroins

In some embodiments, core repeat sequences of the hydrophobic blocks of fibroin are represented by the following amino acid sequences and/or formulae: $(GAGAGS)_{5-15}$ (SEQ ID NO: 1); $(GX)_{5-15}$ (X=V, I, A) (SEQ ID NO: 2); GAAS (SEQ ID NO: 3); $(S_{1-2}A_{11-13})$ (SEQ ID NO: 4); $GX_{1-4}$ GGX (SEQ ID NO: 5); GGGX (X=A, S, Y, R, D V, W, R, D) (SEQ ID NO: 6); $(S_{1-2}A_{1-4})_{1-2}$ (SEQ ID NO: 7); GLGGLG (SEQ ID NO: 8); GXGGXG (X=L, I, V, P) (SEQ ID NO: 9); GPX (X=L, Y, I); $(GP(GGX)_{1-4} Y)n$ (X=Y, V, S, A) (SEQ ID NO: 10); GRGGAn (SEQ ID NO: 11); GGXn (X=A, T, V, S); GAG(A)$_{6-7}$GGA (SEQ ID NO: 12); and GGX GX GXX (X=Q, Y, L, A, S, R) (SEQ ID NO: 13).

In some embodiments, a fibroin peptide contains multiple hydrophobic blocks, e.g., 3, 4, 5, 6, 7, 8, 9, 10, 11, 12, 13, 14, 15, 16, 17, 18, 19 and 20 hydrophobic blocks within the peptide. In some embodiments, a fibroin peptide contains between 4-17 hydrophobic blocks.

In some embodiments of the invention, a fibroin peptide comprises at least one hydrophilic spacer sequence ("hydrophilic block") that is about 4-50 amino acids in length. Non-limiting examples of the hydrophilic spacer sequences include:

TGSSGFGPYVNGGYSG;  (SEQ ID NO: 14)

YEYAWSSE;  (SEQ ID NO: 15)

SDFGTGS;  (SEQ ID NO: 16)

RRAGYDR;  (SEQ ID NO: 17)

EVIVIDDR;  (SEQ ID NO: 18)

TTIIEDLDITIDGADGPI  (SEQ ID NO: 19)
and

TISEELTI.  (SEQ ID NO: 20)

In certain embodiments, a fibroin peptide contains a hydrophilic spacer sequence that is a derivative of any one of the representative spacer sequences listed above. Such derivatives are at least 75%, at least 80%, at least 85%, at least 90%, or at least 95% identical to any one of the hydrophilic spacer sequences.

In some embodiments, a fibroin peptide suitable for the present disclosure contains no spacer.

As noted, silks are fibrous proteins and are characterized by modular units linked together to form high molecular weight, highly repetitive proteins. These modular units or domains, each with specific amino acid sequences and chemistries, are thought to provide specific functions. For example, sequence motifs such as poly-alanine (polyA) and poly-alanine-glycine (poly-AG) are inclined to be beta-sheet-forming; GXX motifs contribute to 31-helix formation; GXG motifs provide stiffness; and, GPGXX (SEQ ID NO: 22) contributes to beta-spiral formation. These are examples of key components in various silk structures whose positioning and arrangement are intimately tied with the end material properties of silk-based materials (reviewed in Omenetto and Kaplan (2010) Science 329: 528-531). Also see: WO 2011/130335 (PCT/US2011/032195), the contents of which are incorporated herein by reference.

In some embodiments, polymers refers to peptide chains or polypeptides having an amino acid sequence corresponding to fragments derived from silk fibroin protein or variants thereof. In the context of nanofibrillar materials of the present disclosure, silk fibroin fragments generally refer to silk fibroin peptide chains or polypeptides that are smaller than naturally occurring full length silk fibroin counterpart, such that one or more of the silk fibroin fragments within a population or composition are less than 500 kDa, less than 450 kDa, less than 400 kDa, less than 350 kDa, less than 300 kDa, less than 250 kDa, less than 200 kDa, less than 175 kDa, less than 150 kDa, less than 120 kDa, less than 100 kDa, less than 90 kDa, less than 80 kDa, less than 70 kDa, less than 60 kDa, less than 50 kDa, less than 40 kDa, less than 30 kDa, less than 25 kDa, less than 20 kDa, less than 15 kDa, less than 12 kDa, less than 10 kDa, less than 9 kDa, less than 8 kDa, less than 7 kDa, less than 6 kDa, less than 5 kDa, less than 4 kDa, less than 3.5 kDa, less than 3 kDa, less than 2.5 kDa, less than 2 kDa, less than 1.5 kDa, or less than about 1.0 kDa, etc.

In some embodiments, polymers of silk fibroin fragments can be derived by degumming silk cocoons at or close to (e.g., within 5% around) an atmospheric boiling temperature for at least about: 1 minute of boiling, 2 minutes of boiling, 3 minutes of boiling, 4 minutes of boiling, 5 minutes of boiling, 6 minutes of boiling, 7 minutes of boiling, 8 minutes of boiling, 9 minutes of boiling, 10 minutes of boiling, 11 minutes of boiling, 12 minutes of boiling, 13 minutes of boiling, 14 minutes of boiling, 15 minutes of boiling, 16 minutes of boiling, 17 minutes of boiling, 18 minutes of boiling, 19 minutes of boiling, 20 minutes of boiling, 25 minutes of boiling, 30 minutes of boiling, 35 minutes of boiling, 40 minutes of boiling, 45 minutes of boiling, 50 minutes of boiling, 55 minutes of boiling, 60 minutes or longer, including, e.g., at least 70 minutes, at least 80 minutes, at least 90 minutes, at least 100 minutes, at least 110 minutes, at least about 120 minutes or longer. As used herein, the term "atmospheric boiling temperature" refers to a temperature at which a liquid boils under atmospheric pressure.

In some embodiments, hydrogels of the present disclosure produced from silk fibroin fragments can be formed by degumming silk cocoons in an aqueous solution at temperatures of: about 30° C., about 35° C., about 40° C., about 45° C., about 50° C., about 45° C., about 60° C., about 65° C., about 70° C., about 75° C., about 80° C., about 85° C., about 90° C., about 95° C., about 100° C., about 105° C., about 110° C., about 115° C., about at least 120° C.

In some embodiments, such elevated temperature can be achieved by carrying out at least portion of the heating process (e.g., boiling process) under pressure. For example, suitable pressure under which silk fibroin fragments described herein can be produced are typically between about 10-40 psi, e.g., about 11 psi, about 12 psi, about 13 psi, about 14 psi, about 15 psi, about 16 psi, about 17 psi, about 18 psi, about 19 psi, about 20 psi, about 21 psi, about 22 psi, about 23 psi, about 24 psi, about 25 psi, about 26 psi, about 27 psi, about 28 psi, about 29 psi, about 30 psi, about 31 psi, about 32 psi, about 33 psi, about 34 psi, about 35 psi, about 36 psi, about 37 psi, about 38 psi, about 39 psi, or about 40 psi.

In some embodiments, silk fibroin fragments solubilized prior to gelation. In some embodiments, a carrier can be a solvent or dispersing medium. In some embodiments, a solvent and/or dispersing medium, for example, is water, cell culture medium, buffers (e.g., phosphate buffered saline), a buffered solution (e.g. PBS), polyol (for example, glycerol, propylene glycol, liquid polyethylene glycol, and the like), Dulbecco's Modified Eagle Medium, fetal bovine serum, or suitable combinations and/or mixtures thereof.

In some embodiments, nanofibrillar materials are modulated by controlling a silk concentration. In some embodiments, a weight percentage of silk fibroin can be present in the solution at any concentration suited to the need. In some embodiments, an aqueous silk fibroin solution can have silk fibroin at a concentration of about 0.1 wt % to about 95 wt %, 0.1 wt % to about 75 wt %, or 0.1 wt % to about 50 wt %. In some embodiments, the aqueous silk fibroin solution can have silk fibroin at a concentration of about 0.1 wt % to about 10 wt %, about 0.1 wt % to about 5 wt %, about 0.1 wt % to about 2 wt %, or about 0.1 wt % to about 1 wt %. In some embodiments, the silk fibroin solution have silk fibroin at a concentration of about 10 wt % to about 50 wt %, about 20 wt % to about 50 wt %, about 25 wt % to about 50 wt %, or about 30 wt % to about 50 wt %. In some embodiments, a weight percent of silk in solution is about less than 1 wt %, is about less than 1.5 wt %, is about less than 2 wt %, is about less than 2.5 wt %, is about less than 3 wt %, is about less than 3.5 wt %, is about less than 4 wt %, is about less than 4.5 wt %, is about less than 5 wt %, is about less than 5.5 wt %, is about less than 6 wt %, is about less than 6.5 wt %, is about less than 7 wt %, is about less than 7.5 wt %, is about less than 8 wt %, is about less than 8.5 wt %, is about less than 9 wt %, is about less than 9.5 wt %, is about less than 10 wt %, is about less than 11 wt %, is about less than 12 wt %, is about less than 13 wt %, is about less than 14 wt %, is about less than 15 wt %, is about less than 16 wt %, is about less than 17 wt %, is about less than 18 wt %, is about less than 19 wt %, is about less than 20 wt %, is about less than 25 wt %, or is about less than 30 wt %.

Degradation Properties of Silk-Based Materials

Additionally, as will be appreciated by those of skill in the art, much work has established that researchers have the ability to control the degradation process of silk. According to the present disclosure, such control can be particularly valuable in the fabrication of electronic components, and particularly of electronic components that are themselves and/or are compatible with biomaterials. Degradability (e.g., bio-degradability) is often essential for biomaterials used in tissue engineering and implantation. The present disclosure encompasses the recognition that such degradability is also relevant to and useful in the fabrication of silk electronic components.

According to the present disclosure, one particularly desirable feature of silk-based materials is the fact that they can be programmably degradable. That is, as is known in the art, depending on how a particular silk-based material is prepared, it can be controlled to degrade at certain rates. Degradability and controlled release of a substance from silk-based materials have been published (see, for example, WO 2004/080346, WO 2005/012606, WO 2005/123114, WO 2007/016524, WO 2008/150861, WO 2008/118133, each of which is incorporated by reference herein).

Control of silk material production methods as well as various forms of silk-based materials can generate silk compositions with known degradation properties. For example, using various silk fibroin materials (e.g., microspheres of approximately 2 μm in diameter, silk film, silk hydrogels) entrapped agents such as therapeutics can be loaded in active form, which is then released in a controlled fashion, e.g., over the course of minutes, hours, days, weeks to months. It has been shown that layered silk fibroin coatings can be used to coat substrates of any material, shape and size, which then can be used to entrap molecules for controlled release, e.g., 2-90 days.

Crystalline Silk Materials

As known in the art and as described herein, silk proteins can stack with one another in crystalline arrays. Various properties of such arrays are determined, for example, by the degree of beta-sheet structure in the material, the degree of cross-linking between such beta sheets, the presence (or absence) of certain dopants or other materials. In some embodiments, one or more of these features is intentionally controlled or engineered to achieve particular characteristics of a silk matrix.

Functional Moieties and/or Agents

Nanofibers of the provided nanofibrillar materials can consist essentially of purified protein or polypeptides, although additional component or components may be optionally incorporated to form such nanofibers. Thus, in some embodiments, nanofibers of a nanofibrillar materials described in the present application consist essentially of a dehydrated polypeptides.

In some embodiments, provided nanofibrillar materials can comprise one or more (e.g., one, two, three, four, five or more) agents and/or functional moieties (together, "additives"). Without wishing to be bound by a theory additive can provide or enhance one or more desirable properties, e.g., strength, flexibility, ease of processing and handling, biocompatibility, bioresorability, surface morphology, release rates and/or kinetics of one or more active agents present in the composition, and the like. In some embodiments, one or more such additives can be covalently or non-covalently linked with the nanofibrillar materials (e.g., with a polymer such as silk fibroin that makes up the nanofibrillar materials) and can be integrated homogenously or heterogeneously within the silk composition.

In some embodiments, an additive is or comprises a moiety covalently associated (e.g., via chemical modification or genetic engineering) with a polymer. In some embodiments, an additive is non-covalently associated with a nanofibrillar materials or nanofibrillar materials component.

In some embodiments, provided nanofibrillar materials comprise additives at a total amount from about 0.01 wt % to about 99 wt %, from about 0.01 wt % to about 70 wt %, from about 5 wt % to about 60 wt %, from about 10 wt % to about 50 wt %, from about 15 wt % to about 45 wt %, or from about 20 wt % to about 40 wt %, of the total silk composition. In some embodiments, ratio of silk fibroin to additive in the composition can range from about 1000:1 (w/w) to about 1:1000 (w/w), from about 500:1 (w/w) to about 1:500 (w/w), from about 250:1 (w/w) to about 1:250 (w/w), from about 200:1 (w/w) to about 1:200 (w/w), from about 25:1 (w/w) to about 1:25 (w/w), from about 20:1 (w/w) to about 1:20 (w/w), from about 10:1 (w/w) to about 1:10 (w/w), or from about 5:1 (w/w) to about 1:5 (w/w).

In some embodiments, provided nanofibrillar materials include one or more additives at a molar ratio relative to polymer (i.e., a polymer:additive ratio) of, e.g., at least 1000:1, at least 900:1, at least 800:1, at least 700:1, at least 600:1, at least 500:1, at least 400:1, at least 300:1, at least 200:1, at least 100:1, at least 90:1, at least 80:1, at least 70:1, at least 60:1, at least 50:1, at least 40:1, at least 30:1, at least 20:1, at least 10:1, at least 7:1, at least 5:1, at least 3:1, at least 1:1, at least 1:3, at least 1:5, at least 1:7, at least 1:10, at least 1:20, at least 1:30, at least 1:40, at least 1:50, at least 1:60, at least 1:70, at least 1:80, at least 1:90, at least 1:100, at least 1:200, at least 1:300, at least 1:400, at least 1:500, at least 600, at least 1:700, at least 1:800, at least 1:900, or at least 1:100.

In some embodiments, moiety polymer:additive ratio is, e.g., at most 1000:1, at most 900:1, at most 800:1, at most 700:1, at most 600:1, at most 500:1, at most 400:1, at most 300:1, at most 200:1, 100:1, at most 90:1, at most 80:1, at most 70:1, at most 60:1, at most 50:1, at most 40:1, at most 30:1, at most 20:1, at most 10:1, at most 7:1, at most 5:1, at most 3:1, at most 1:1, at most 1:3, at most 1:5, at most 1:7, at most 1:10, at most 1:20, at most 1:30, at most 1:40, at most 1:50, at most 1:60, at most 1:70, at most 1:80, at most 1:90, at most 1:100, at most 1:200, at most 1:300, at most 1:400, at most 1:500, at most 1:600, at most 1:700, at most 1:800, at most 1:900, or at most 1:1000.

In some embodiments, moiety polymer:additive ratio is, e.g., from about 1000:1 to about 1:1000, from about 900:1 to about 1:900, from about 800:1 to about 1:800, from about 700:1 to about 1:700, from about 600:1 to about 1:600, from about 500:1 to about 1:500, from about 400:1 to about 1:400, from about 300:1 to about 1:300, from about 200:1 to about 1:200, from about 100:1 to about 1:100, from about 90:1 to about 1:90, from about 80:1 to about 1:80, from about 70:1 to about 1:70, from about 60:1 to about 1:60, from about 50:1 to about 1:50, from about 40:1 to about 1:40, from about 30:1 to about 1:30, from about 20:1 to about 1:20, from about 10:1 to about 1:10, from about 7:1 to about 1:7, from about 5:1 to about 1:5, from about 3:1 to about 1:3, or about 1:1.

In some embodiments, provided nanofibrillar materials comprise additives, for example, therapeutic, preventative, and/or diagnostic agents.

In some embodiments, an additive is or comprises one or more therapeutic agents. In general, a therapeutic agent is or comprises a small molecule and/or organic compound with pharmaceutical activity (e.g., activity that has been demonstrated with statistical significance in one or more relevant pre-clinical models or clinical settings). In some embodiments, a therapeutic agent is a clinically-used drug. In some embodiments, a therapeutic agent is or comprises an cells, proteins, peptides, nucleic acid analogues, nucleotides, oligonucleotides, nucleic acids (DNA, RNA, siRNA), peptide nucleic acids, aptamers, antibodies or fragments or portions thereof, anesthetic, anticoagulant, anti-cancer agent, inhibitor of an enzyme, steroidal agent, anti-inflammatory agent, anti-neoplastic agent, antigen, vaccine, antibody, decongestant, antihypertensive, sedative, birth control agent, progestational agent, anti-cholinergic, analgesic, anti-depressant, anti-psychotic, β-adrenergic blocking agent, diuretic, cardiovascular active agent, vasoactive agent, anti-glaucoma agent, neuroprotectant, angiogenesis inhibitor, hormones, hormone antagonists, growth factors or recombinant growth factors and fragments and variants thereof, cytokines, enzymes, antibiotics or antimicrobial compounds, antifungals, antivirals, toxins, prodrugs, chemotherapeutic agents, small molecules, drugs (e.g., drugs, dyes, amino acids, vitamins, antioxidants), pharmacologic agents, and combinations thereof.

In some embodiments, provided nanofibrillar materials comprise additives, for example, cells. Cells suitable for use herein include, but are not limited to, progenitor cells or stem cells, smooth muscle cells, skeletal muscle cells, cardiac muscle cells, epithelial cells, endothelial cells, urothelial cells, fibroblasts, myoblasts, chondrocytes, chondroblasts, osteoblasts, osteoclasts, keratinocytes, hepatocytes, bile duct cells, pancreatic islet cells, thyroid, parathyroid, adrenal, hypothalamic, pituitary, ovarian, testicular, salivary gland cells, adipocytes, and precursor cells.

In some embodiments, provided nanofibrillar materials comprise additives, for example, organisms, such as, a bacterium, fungus, plant or animal, or a virus. In some embodiments, an active agent may include or be selected from neurotransmitters, hormones, intracellular signal transduction agents, pharmaceutically active agents, toxic agents, agricultural chemicals, chemical toxins, biological toxins, microbes, and animal cells such as neurons, liver cells, and immune system cells. The active agents may also include therapeutic compounds, such as pharmacological materials, vitamins, sedatives, hypnotics, prostaglandins and radiopharmaceuticals.

In some embodiments, provided nanofibrillar materials comprise additives, for example, antibiotics. Antibiotics suitable for incorporation in nanofibrillar materials include, but are not limited to, aminoglycosides (e.g., neomycin), ansamycins, carbacephem, carbapenems, cephalosporins (e.g., cefazolin, cefaclor, cefditoren, cefditoren, ceftobiprole), glycopeptides (e.g., vancomycin), macrolides (e.g., erythromycin, azithromycin), monobactams, penicillins (e.g., amoxicillin, ampicillin, cloxacillin, dicloxacillin, flucloxacillin), polypeptides (e.g., bacitracin, polymyxin B), quinolones (e.g., ciprofloxacin, enoxacin, gatifloxacin, ofloxacin, etc.), sulfonamides (e.g., sulfasalazine, trimethoprim, trimethoprim-sulfamethoxazole (co-trimoxazole)), tetracyclines (e.g., doxycyline, minocycline, tetracycline, etc.), chloramphenicol, lincomycin, clindamycin, ethambutol, mupirocin, metronidazole, pyrazinamide, thiamphenicol, rifampicin, thiamphenicl, dapsone, clofazimine, quinupristin, metronidazole, linezolid, isoniazid, fosfomycin, fusidic acid, β-lactam antibiotics, rifamycins, novobiocin, fusidate sodium, capreomycin, colistimethate, gramicidin, doxycycline, erythromycin, nalidixic acid, and vancomycin. For example, β-lactam antibiotics can be aziocillin, aztreonam, carbenicillin, cefoperazone, ceftriaxone, cephaloridine, cephalothin, moxalactam, piperacillin, ticarcillin and combination thereof.

In some embodiments, provided nanofibrillar materials comprise additives, for example, anti-inflammatories. Anti-inflammatory agents may include corticosteroids (e.g., glucocorticoids), cycloplegics, non-steroidal anti-inflammatory drugs (NSAIDs), immune selective anti-inflammatory derivatives (ImSAIDs), and any combination thereof. Exemplary NSAIDs include, but not limited to, celecoxib (Celebrex®); rofecoxib (Vioxx®), etoricoxib (Arcoxia®), meloxicam (Mobic®), valdecoxib, diclofenac (Voltaren®, Cataflam®), etodolac (Lodine®), sulindac (Clinori®), aspirin, alclofenac, fenclofenac, diflunisal (Dolobid®), benorylate, fosfosal, salicylic acid including acetylsalicylic acid, sodium acetylsalicylic acid, calcium acetylsalicylic acid, and sodium salicylate; ibuprofen (Motrin), ketoprofen, carprofen, fenbufen, flurbiprofen, oxaprozin, suprofen, triaprofenic acid, fenoprofen, indoprofen, piroprofen, flufenamic, mefenamic, meclofenamic, niflumic, salsalate, rolmerin, fentiazac, tilomisole, oxyphenbutazone, phenylbutazone, apazone, feprazone, sudoxicam, isoxicam, tenoxicam, piroxicam (Feldene®), indomethacin (Indocin®), nabumetone (Relafen®), naproxen (Naprosyn®), tolmetin, lumiracoxib, parecoxib, licofelone (ML3000), including pharmaceutically acceptable salts, isomers, enantiomers, derivatives, prodrugs, crystal polymorphs, amorphous modifications, co-crystals and combinations thereof.

In some embodiments, provided nanofibrillar materials comprise additives, for example, antibodies. Suitable antibodies for incorporation in nanofibrillar materials include, but are not limited to, abciximab, adalimumab, alemtuzumab, basiliximab, bevacizumab, cetuximab, certolizumab pegol, daclizumab, eculizumab, efalizumab, gemtuzumab, ibritumomab tiuxetan, infliximab, muromonab-CD3, natalizumab, ofatumumab omalizumab, palivizumab, panitumumab, ranibizumab, rituximab, tositumomab, trastuzumab, altumomab pentetate, arcitumomab, atlizumab, bectumomab, belimumab, besilesomab, biciromab, canakinumab, capromab pendetide, catumaxomab, denosumab, edrecolomab, efungumab, ertumaxomab, etaracizumab, fanolesomab, fontolizumab, gemtuzumab ozogamicin, golimumab, igovomab, imciromab, labetuzumab, mepolizumab, motavizumab, nimotuzumab, nofetumomab merpentan, oregovomab, pemtumomab, pertuzumab, rovelizumab, ruplizumab, sulesomab, tacatuzumab tetraxetan, tefibazumab, tocilizumab, ustekinumab, visilizumab, votumumab, zalutumumab, and zanolimumab.

In some embodiments, provided nanofibrillar materials comprise additives, for example, polypeptides (e.g., proteins), including but are not limited to: one or more antigens, cytokines, hormones, chemokines, enzymes, and any combination thereof as an agent and/or functional group. Exemplary enzymes suitable for use herein include, but are not limited to, peroxidase, lipase, amylose, organophosphate dehydrogenase, ligases, restriction endonucleases, ribonucleases, DNA polymerases, glucose oxidase, laccase, and the like.

In some embodiments, provided nanofibrillar materials comprise additives, for example, particularly useful for wound healing. In some embodiments, agents useful for wound healing include stimulators, enhancers or positive mediators of the wound healing cascade which 1) promote or accelerate the natural wound healing process or 2) reduce effects associated with improper or delayed wound healing, which effects include, for example, adverse inflammation, epithelialization, angiogenesis and matrix deposition, and scarring and fibrosis.

In some embodiments, provided nanofibrillar materials comprise additives, for example, an optically or electrically active agent, including but not limited to, chromophores; light emitting organic compounds such as luciferin, carotenes; light emitting inorganic compounds, such as chemical dyes; light harvesting compounds such as chlorophyll, bacteriorhodopsin, protorhodopsin, and porphyrins; light capturing complexes such as phycobiliproteins; and related electronically active compounds; and combinations thereof.

Nucleic Acids

In some embodiments, provided nanofibrillar materials comprise additives, for example, nucleic acid agents. In some embodiments, a nanofibrillar materials may release nucleic acid agents. In some embodiments, a nucleic acid agent is or comprises a therapeutic agent. In some embodiments, a nucleic acid agent is or comprises a diagnostic agent. In some embodiments, a nucleic acid agent is or comprises a prophylactic agent.

It would be appreciate by those of ordinary skill in the art that a nucleic acid agent can have a length within a broad range. In some embodiments, a nucleic acid agent has a nucleotide sequence of at least about 40, for example at least about 60, at least about 80, at least about 100, at least about 200, at least about 500, at least about 1000, or at least about 3000 nucleotides in length. In some embodiments, a nucleic acid agent has a length from about 6 to about 40 nucleotides. For example, a nucleic acid agent may be from about 12 to about 35 nucleotides in length, from about 12 to about 20 nucleotides in length or from about 18 to about 32 nucleotides in length.

In some embodiments, nucleic acid agents may be or comprise deoxyribonucleic acids (DNA), ribonucleic acids (RNA), peptide nucleic acids (PNA), morpholino nucleic acids, locked nucleic acids (LNA), glycol nucleic acids (GNA), threose nucleic acids (TNA), and/or combinations thereof.

In some embodiments, a nucleic acid has a nucleotide sequence that is or comprises at least one protein-coding element. In some embodiments, a nucleic acid has a nucleotide sequence that is or comprises at least one element that is a complement to a protein-coding sequence. In some embodiments, a nucleic acid has a nucleotide sequence that includes one or more gene expression regulatory elements (e.g., promoter elements, enhancer elements, splice donor sites, splice acceptor sites, transcription termination sequences, translation initiation sequences, translation termination sequences, etc.). In some embodiments, a nucleic acid has a nucleotide sequence that includes an origin of replication. In some embodiments, a nucleic acid has a nucleotide sequence that includes one or more integration sequences. In some embodiments, a nucleic acid has a nucleotide sequence that includes one or more elements that participate in intra- or inter-molecular recombination (e.g., homologous recombination). In some embodiments, a nucleic acid has enzymatic activity. In some embodiments, a nucleic acid hybridizes with a target in a cell, tissue, or organism. In some embodiments, a nucleic acid acts on (e.g., binds with, cleaves, etc.) a target inside a cell. In some embodiments, a nucleic acid is expressed in a cell after release from a provided composition. In some embodiments, a nucleic acid integrates into a genome in a cell after release from a provided composition.

In some embodiments, nucleic acid agents have single-stranded nucleotide sequences. In some embodiments, nucleic acid agents have nucleotide sequences that fold into higher order structures (e.g., double and/or triple-stranded structures). In some embodiments, a nucleic acid agent is or comprises an oligonucleotide. In some embodiments, a nucleic acid agent is or comprises an antisense oligonucleotide. Nucleic acid agents may include a chemical modification at the individual nucleotide level or at the oligonucleotide backbone level, or it may have no modifications.

In some embodiments of the present disclosure, a nucleic acid agent is an siRNA agent. Short interfering RNA (siRNA) comprises an RNA duplex that is approximately 19 basepairs long and optionally further comprises one or two single-stranded overhangs. An siRNA may be formed from two RNA molecules that hybridize together, or may alternatively be generated from a single RNA molecule that includes a self-hybridizing portion. It is generally preferred that free 5' ends of siRNA molecules have phosphate groups, and free 3' ends have hydroxyl groups. The duplex portion of an siRNA may, but typically does not, contain one or more bulges consisting of one or more unpaired nucleotides. One strand of an siRNA includes a portion that hybridizes with a target transcript. In certain preferred embodiments of the invention, one strand of the siRNA is precisely complementary with a region of the target transcript, meaning that the siRNA hybridizes to the target transcript without a single mismatch. In other embodiments of the invention one or more mismatches between the siRNA and the targeted portion of the target transcript may exist. In most embodiments of the invention in which perfect complementarity is not achieved, it is generally preferred that any mismatches be located at or near the siRNA termini.

Short hairpin RNA refers to an RNA molecule comprising at least two complementary portions hybridized or capable of hybridizing to form a double-stranded (duplex) structure sufficiently long to mediate RNAi (typically at least 19 base pairs in length), and at least one single-stranded portion, typically between approximately 1 and 10 nucleotides in length that forms a loop. The duplex portion may, but typically does not, contain one or more bulges consisting of one or more unpaired nucleotides. As described further below, shRNAs are thought to be processed into siRNAs by the conserved cellular RNAi machinery. Thus shRNAs are precursors of siRNAs and are, in general, similarly capable of inhibiting expression of a target transcript.

In describing siRNAs it will frequently be convenient to refer to sense and antisense strands of the siRNA. In general, the sequence of the duplex portion of the sense strand of the siRNA is substantially identical to the targeted portion of the target transcript, while the antisense strand of the siRNA is substantially complementary to the target transcript in this region as discussed further below. Although shRNAs contain a single RNA molecule that self-hybridizes, it will be appreciated that the resulting duplex structure may be considered to comprise sense and antisense strands or portions. It will therefore be convenient herein to refer to sense and antisense strands, or sense and antisense portions, of an shRNA, where the antisense strand or portion is that segment of the molecule that forms or is capable of forming a duplex and is substantially complementary to the targeted portion of the target transcript, and the sense strand or portion is that segment of the molecule that forms or is capable of forming a duplex and is substantially identical in sequence to the targeted portion of the target transcript.

For purposes of description, the discussion below may refer to siRNA rather than to siRNA or shRNA. However, as will be evident to one of ordinary skill in the art, teachings relevant to the sense and antisense strand of an siRNA are generally applicable to the sense and antisense portions of the stem portion of a corresponding shRNA. Thus in general the considerations below apply also to shRNAs.

An siRNA agent is considered to be targeted to a target transcript for the purposes described herein if 1) the stability of the target transcript is reduced in the presence of the siRNA or shRNA as compared with its absence; and/or 2) the siRNA or shRNA shows at least about 90%, more preferably at least about 91%, 92%, 93%, 94%, 95%, 96%, 97%, 98%, 99%, or 100% precise sequence complementarity with the target transcript for a stretch of at least about 15, more preferably at least about 17, yet more preferably at least about 18 or 19 to about 21-23 nucleotides; and/or 3) one strand of the siRNA or one of the self-complementary portions of the shRNA hybridizes to the target transcript under stringent conditions for hybridization of small (<50 nucleotide) RNA molecules in vitro and/or under conditions typically found within the cytoplasm or nucleus of mammalian cells. Since the effect of targeting a transcript is to reduce or inhibit expression of the gene that directs synthesis of the transcript, an siRNA, shRNA, targeted to a transcript is also considered to target the gene that directs synthesis of the transcript even though the gene itself (i.e., genomic DNA) is not thought to interact with the siRNA, shRNA, or components of the cellular silencing machinery. Thus in some embodiments, an siRNA, shRNA, that targets a transcript is understood to target the gene that provides a template for synthesis of the transcript.

In some embodiments, an siRNA agent can inhibit expression of a polypeptide (e.g., a protein). Exemplary polypeptides include, but are not limited to, matrix metallopeptidase 9 (MMP-9), neutral endopeptidase (NEP) and protein tyrosine phosphatase 1B (PTP1B).

Growth Factor

In some embodiments, provided nanofibrillar materials comprise additives, for example, growth factor. In some embodiments, a hydrogel may release growth factor. In some embodiments, a hydrogel may release multiple growth factors. In some embodiments growth factor known in the art include, for example, adrenomedullin, angiopoietin, autocrine motility factor, basophils, brain-derived neurotrophic factor, bone morphogenetic protein, colony-stimulating factors, connective tissue growth factor, endothelial cells, epidermal growth factor, erythropoietin, fibroblast growth factor, fibroblasts, glial cell line-derived neurotrophic factor, granulocyte colony stimulating factor, granulocyte macrophage colony stimulating factor, growth differentiation factor-9, hepatocyte growth factor, hepatoma-derived growth factor, insulin-like growth factor, interleukins, keratinocyte growth factor, keratinocytes, lymphocytes, macrophages, mast cells, myostatin, nerve growth factor, neurotrophins, platelet-derived growth factor, placenta growth factor, osteoblasts, platelets, proinflammatory, stromal cells, T-lymphocytes, thrombopoietin, transforming growth factor alpha, transforming growth factor beta, tumor necrosis factor-alpha, vascular endothelial growth factor and combinations thereof.

In some embodiments, provided nanofibrillar materials comprise additives, for example, that are particularly useful for healing. Exemplary agents useful as growth factor for defect repair and/or healing can include, but are not limited to, growth factors for defect treatment modalities now known in the art or later-developed; exemplary factors, agents or modalities including natural or synthetic growth factors, cytokines, or modulators thereof to promote bone and/or tissue defect healing. Suitable examples may include, but not limited to 1) topical or dressing and related therapies and debriding agents (such as, for example, Santyl® collagenase) and Iodosorb® (cadexomer iodine); 2) antimicrobial agents, including systemic or topical creams or gels, including, for example, silver-containing agents such as SAGs (silver antimicrobial gels), (CollaGUARD™, Innocoll, Inc) (purified type-I collagen protein based dressing), CollaGUARD Ag (a collagen-based bioactive dressing impregnated with silver for infected wounds or wounds at risk of infection), DermaSIL™ (a collagen-synthetic foam composite dressing for deep and heavily exuding wounds); 3) cell therapy or bioengineered skin, skin substitutes, and skin equivalents, including, for example, Dermograft (3-dimensional matrix cultivation of human fibroblasts that secrete cytokines and growth factors), Apligraf® (human keratinocytes and fibroblasts), Graftskin® (bilayer of epidermal cells and fibroblasts that is histologically similar to normal skin and produces growth factors similar to those produced by normal skin), TransCyte (a Human Fibroblast Derived Temporary Skin Substitute) and Oasis® (an active biomaterial that comprises both growth factors and extracellular matrix components such as collagen, proteoglycans, and glycosaminoglycans); 4) cytokines, growth factors or hormones (both natural and synthetic) introduced to the wound to promote wound healing, including, for example, NGF, NT3, BDGF, integrins, plasmin, semaphoring, blood-derived growth factor, keratinocyte growth factor, tissue growth factor, TGF-alpha, TGF-beta, PDGF (one or more of the three subtypes may be used: AA, AB, and B), PDGF-BB, TGF-beta 3, factors that modulate the relative levels of TGFβ3, TGFβ1, and TGFβ2 (e.g., Mannose-6-phosphate), sex steroids, including for example, estrogen, estradiol, or an oestrogen receptor agonist selected from the group consisting of ethinyloestradiol, dienoestrol, mestranol, oestradiol, oestriol, a conjugated oestrogen, piperazine oestrone sulphate, stilboestrol, fosfesterol tetrasodium, polyestradiol phosphate, tibolone, a phytoestrogen, 17-beta-estradiol; thymic hormones such as Thymosin-beta-4, EGF, HB-EGF, fibroblast growth factors (e.g., FGF1, FGF2, FGF7), keratinocyte growth factor, TNF, interleukins family of inflammatory response modulators such as, for example, IL-10, IL-1, IL-2, IL-6, IL-8, and IL-10 and modulators thereof; INFs (INF-alpha, -beta, and -delta); stimulators of activin or inhibin, and inhibitors of interferon gamma prostaglandin E2 (PGE2) and of mediators of the adenosine 3',5'-cyclic monophosphate (cAMP) pathway; adenosine A1 agonist, adenosine A2 agonist or 5) other agents useful for wound healing, including, for example, both natural or synthetic homologues, agonist and antagonist of VEGF, VEGFA, IGF; IGF-1, proinflammatory cytokines, GM-CSF, and leptins and 6) IGF-1 and KGF cDNA, autologous platelet gel, hypochlorous acid (Sterilox® lipoic acid, nitric oxide synthase3, matrix metalloproteinase 9 (MMP-9), CCT-ETA, alphavbeta6 integrin, growth factor-primed fibroblasts and Decorin, silver containing wound dressings, Xenaderm™, papain wound debriding agents, lactoferrin, substance P, collagen, and silver-ORC, placental alkaline phosphatase or placental growth factor, modulators of hedgehog signaling, modulators of cholesterol synthesis pathway, and APC (Activated Protein C), keratinocyte growth factor, TNF, Thromboxane A2, NGF, BMP bone morphogenetic protein, CTGF (connective tissue growth factor), wound healing chemokines, decorin, modulators of lactate induced neovascularization, cod liver oil, placental alkaline phosphatase or placental growth factor, and thymosin beta 4. In certain embodiments, one, two three, four, five or six agents useful for wound healing may be used in combination. More details can be found in U.S. Pat. No. 8,247,384, the contents of which are incorporated herein by reference.

It is to be understood that agents useful for growth factor for healing (including for example, growth factors and cytokines) above encompass all naturally occurring polymorphs (for example, polymorphs of the growth factors or cytokines). Also, functional fragments, chimeric proteins comprising one of said agents useful for wound healing or a functional fragment thereof, homologues obtained by analogous substitution of one or more amino acids of the wound healing agent, and species homologues are encompassed. It is contemplated that one or more agents useful for wound healing may be a product of recombinant DNA technology, and one or more agents useful for wound healing may be a product of transgenic technology. For example, platelet derived growth factor may be provided in the form of a recombinant PDGF or a gene therapy vector comprising a coding sequence for PDGF.

In some embodiments, provided nanofibrillar materials comprise additives, for example, that are particularly useful as diagnostic agents. In some embodiments, diagnostic agents include gases; commercially available imaging agents used in positron emissions tomography (PET), computer assisted tomography (CAT), single photon emission computerized tomography, x-ray, fluoroscopy, and magnetic resonance imaging (MRI); and contrast agents. Examples of suitable materials for use as contrast agents in MRI include gadolinium chelates, as well as iron, magnesium, manganese, copper, and chromium. Examples of materials useful for CAT and x-ray imaging include iodine-based materials.

In some embodiments, provided nanofibrillar materials comprise additives, for example, radionuclides that are particularly useful as therapeutic and/or diagnostic agents. Among the radionuclides used, gamma-emitters, positron-emitters, and X-ray emitters are suitable for diagnostic and/or therapy, while beta emitters and alpha-emitters may also be used for therapy. Suitable radionuclides for forming thermally-responsive conjugates in accordance with the invention include, but are not limited to, $^{123}I$, $^{125}I$, $^{130}I$, $^{131}I$, $^{133}I$, $^{135}I$, $^{47}Sc$, $^{72}As$, $^{72}Se$, $^{90}Y$, $^{88}Y$, $^{97}Ru$, $^{100}Pd$, $^{101}mRh$, $^{119}Sb$, $^{128}Ba$, $^{197}Hg$, $^{211}At$, $^{212}Bi$, $^{212}Pb$, $^{109}Pd$, $^{111}In$, $^{67}Ga$, $^{68}Ga$, $^{67}Cu$, $^{75}Br$, $^{77}Br$, $^{99}mTc$, $^{14}C$, $^{13}N$, $^{15}O$, $^{32}P$, $^{33}P$, and $^{18}F$. In some embodiments, a diagnostic agent may be a fluorescent, luminescent, or magnetic moiety.

Fluorescent and luminescent moieties include a variety of different organic or inorganic small molecules commonly referred to as "dyes," "labels," or "indicators." Examples include fluorescein, rhodamine, acridine dyes, Alexa dyes, cyanine dyes, etc. Fluorescent and luminescent moieties may include a variety of naturally occurring proteins and derivatives thereof, e.g., genetically engineered variants. For example, fluorescent proteins include green fluorescent protein (GFP), enhanced GFP, red, blue, yellow, cyan, and sapphire fluorescent proteins, reef coral fluorescent protein, etc. Luminescent proteins include luciferase, aequorin and derivatives thereof. Numerous fluorescent and luminescent dyes and proteins are known in the art (see, e.g., U.S. Patent Application Publication No.: 2004/0067503; Valeur, B., "Molecular Fluorescence: Principles and Applications," John Wiley and Sons, 2002; *Handbook of Fluorescent Probes and Research Products*, Molecular Probes, 9$^{th}$ edition, 2002; and *The Handbook—A Guide to Fluorescent Probes and Labeling Technologies*, Invitrogen, 10$^{th}$ edition, available at the Invitrogen web site; both of which are incorporated herein by reference).

EXEMPLIFICATION

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

Example 1

The present Example describes synthesis and characterization of silk fibroin nanofibrillar materials and the effect that varying solution concentration has on nanofibrillar material properties.

Materials and Methods

Silk Fibroin Solution Preparation

*B. mori* silkworm cocoons were boiled for 30 minutes in a solution of 0.02 M Na$_2$CO$_3$ to remove the sericin glycoprotein. The extracted fibroin was rinsed in deionized water and set to dry for 12 hours. The dried fibroin was dissolved in 9.3 M LiBr solution at 60° C. for 3 hours. The solution was dialyzed against deionized water using a dialysis cassette (Slide-a-Lyzer, Pierce, MWCO 3.5 KDa) at room temperature for 2 days until the solution reaches a concentration of ~60 mg/ml. The resultant solution was purified using centrifugation and filtered through a 5 µm syringe filter.

Silk Nanofibrillar Material Synthesis

Acetone Optima (Fisher Scientific) was used to synthesize the nanofibrillar material. Acetone was set in a glass Petri dish. Varying concentrations of silk solution (7.5 mg/ml, 10 mg/ml, 15 mg/ml 20 mg/ml, 30 mg/ml) were added into the acetone bath. The ratio of silk solution to acetone was typically not more than 2:1 since the addition of more fibroin produced less transparent gels. The acetone was evaporated at room temperature (flashed off) for 12 hours while adding deionized water to prevent the sol-gel from collapsing. The sol-gel was soaked in a 20 mM solution of ethylenediaminetetraacetic acid (EDTA) (pH=8.5, Sigma Aldrich) for 24 hours to increase the stiffness of the gels. The gels were rinsed in deionized water again to remove any access EDTA. These hydrogels were prepared for critical point drying by soaking in baths of 200 Proof ethanol. Baths of 50%, 75%, 80%, 90%, 95%, 100%, and 100% ethanol were prepared and hydrogel samples were set in each bath for 30 minutes to completely dehydrate the sample and prepare an nanofibrillar material. Critical point drying of the samples was conducted in an Auto Samdri 815 Series A (Tousimis, Rockville, Md.).

Results

Macroscale images of silk nanofibrillar material samples are shown in FIG. 1. FIG. 1 shows macroscale images of varying concentrations of silk nanofibrillar materials. A nanofibrillar material made from an initial silk concentrations of 7.5 mg/ml is shown in FIG. 1a, an initial silk concentrations of 10 mg/ml is shown in FIG. 1b, an initial silk concentrations of 15 mg/ml is shown in FIG. 1c, an initial silk concentrations of 20 mg/ml is shown in FIG. 1d, and an initial silk concentrations of 30 mg/ml is shown in FIG. 1e. FIG. 1f shows a scanning electron microscope (SEM) image of a sample having initial silk concentration of 20 mg/ml. The fibers shown in FIG. 1f are approximately 10 nm in diameter with pores between about 2 nm to about 100 nm. When an initial silk solution concentration was increased the resultant nanofibrillar materials were increasingly opaque.

Varying the concentration of silk solution with the same volume (different masses of total silk) changed the bulk density of the silk nanofibrillar materials. As shown in FIG. 2a, silk solution concentrations of 7.5 mg/ml, 10 mg/ml, 15 mg/ml, 20 mg/ml, and 30 mg/ml formed silk nanofibrillar materials with bulk density calculated to be $25.00 \pm 5.14$ $kg/m^3$, $29.4 \pm 3.66$ $kg/m^3$, $47.76 \pm 3.27$ $kg/m^3$, $33.1 \pm 5.45$ $kg/m^3$, and $40.64 \pm 4.90$ $kg/m^3$ (N=6), respectively. It is believed that the change in density is due to the initial starting mass of the silk solution and increases the density of the individual silk nanofibrillar materials.

Changing the initial concentration of the silk solution changed the optical properties of the formed silk nanofibrillar materials. As shown in FIG. 2b, silk solution concentrations of 7.5 mg/ml, 10 mg/ml, 15 mg/ml, 20 mg/ml, and 30 mg/ml formed silk nanofibrillar materials with a thickness of 4.2 mm with varying transmission spectra. Lower concentrations have higher levels of transmission and are more optically clear.

As shown in FIG. 2c, unconfined compressive properties of silk nanofibrillar material samples were measured using an Instron 3366 testing frame (Instron, Norwood, Mass.) with a crosshead speed of 2 mm/min with a 100 N capacity load cell. Samples were conducted in air between force plates. The linear elastic modulus was calculated using a least-squared fitting in the linear region. For initial silk concentrations of 7.5 mg/ml, 10 mg/ml, 15 mg/ml, 20 mg/ml, and 30 mg/ml, the compressive modulus was calculated to be $93.9 \pm 36.0$ kPa, $144.7 \pm 19.8$ kPa, $220.9 \pm 10.5$ kPa, $246.0 \pm 61.1$ kPa, and $255.0 \pm 14.2$ kPa (N=3), respectively.

Example 2

The present Example describes synthesis and characterization of a peptide nanofibrillar materials in accordance with the present disclosure. The present Example also describes the addition and characterization of an enzyme. The present Example also describes characterization of nanofibrillar materials used for oxygen sensing.

Materials and Methods

Silk Fibroin Solution Preparation

Silk fibroin solution was prepared as previously described. See D. N. Rockwood, R. C. Preda, T. Yücel, X. Wang, M. L. Lovett, and D. L. Kaplan, Nat. Protoc., 2011, 6, 1612-31, the entire contents of which are hereby incorporated by reference herein. FIG. 1 shows fabrication of silk fibroin nanofibrillar materials in accordance with the present disclosure.

FIG. 1a shows a schematic representation of the processing steps to fabricate silk nanofibrillar materials starting from raw silk cocoons. B. mori silkworm cocoons were boiled for 30 minutes in a solution of 0.02 M $Na_2CO_3$ to remove the outer layers of sericin glycoprotein. The extracted fibroin was rinsed in deionized water and set to dry for 12 hours. During drying, cocoons are unravelled into fibroin fibers. The dried fibroin was dissolved in a highly concentrated solution of chaotropic ions, 9.3 M LiBr solution at 60° C. for 3 hours to solubilize silk fibroin fibers. The solution was dialyzed against deionized water using a dialysis cassette (Slide-a-Lyzer, Pierce, MWCO 3.5 KDa) at room temperature for 2 days until the solution reached a concentration of ~60 mg/ml to remove the chaotropic salts from the solution, yielding a pure fibroin solution. The obtained solution was purified using centrifugation.

Synthesis of Silk Nanofibrillar Materials

FIG. 1b shows a free standing silk fibroin hydrogel are formed, followed by dehydration in ethanol, and supercritical $CO_2$ drying leaving a free standing silk fibroin nanofibrillar material.

FIG. 1c shows a schematic representation of conformational changes within silk fibroin during sol-gel transition. Silk fibroin in solution possess an amorphous structure (mostly random coils) and is arranged in micelles. During gelation, the silk fibroin solution experiences a combination of amorphous-to-crystalline conformational changes together with aggregation results in the formation of silk particles, which arrange together in the presence of water forming a free standing hydrogel structure. During supercritical CO2 drying the formation of nanofibers are formed causing a morphological change of the silk particles.

Acetone Optima (Fisher Scientific) was used to synthesize the initial hydrogel. Acetone was set in a glass Petri dish. Silk solutions of varying concentrations were added drop wise over a period of 30 minutes into the acetone bath. The ratio of silk solution to acetone was typically not more than 2:1 because the addition of more silk fibroin produced less transparent gels. The acetone was evaporated at room temperature for 12 hours while adding deionized water to prevent the hydrogel from collapsing. The hydrogel was soaked in a 20 mM solution of EDTA (pH=8.5, Sigma Aldrich) for 24 hours to improve the hydrogel mechanical properties. The hydrogels were rinsed in deionized water followed by dehydration in a series of ethanol rinses at concentrations of 50%, 70%, 80%, 90%, 95%, 100%, and 100% for 30 minutes to be prepared for supercritical carbon dioxide ($SCCO_2$) drying conducted at 50° C. and 1800 psi. The pressure vessel maintained the same temperature and fluid extraction rate when the pressure was varied to determine nanofiber formation.

Morphological characterization of the silk fibroin nanofibrillar materials without drying with $SCCO_2$ was obtained by drying the samples in hexamethyldisilazane (HMDS). Samples were exposed to a series of HMDS baths at 70%, 90%, 100%, and 100% for 30 minutes to ensure complete saturation. Samples were then left to dry in a chemical hood for 12 hours to allow complete evaporation and then immediately sputter coated for SEM analysis.

Measurements

Morphological Measurements:

SEM images were taken by a Supra55VP FESEM (Zeiss) using the SE2 detector. Samples were sputter coated using platinum/palladium or gold and imaged at 4 kV.

Density/Porosity Measurements

Bulk density of the silk nanofibrillar materials was conducted by weighing the samples and dividing by the sample volume using a standard laboratory bench top scale.

Transmission Measurements

Spectra were taken using a vis/near-infrared fiber-optic spectrometer (USB-2000, Ocean Optics). White light was propagated through the fiber to illuminate the sample. The transmitted light was coupled into a fiber tip opposite to the spectrometer. The distance between the illumination source and the collection tip was fixed at 7 mm. All samples had a thickness of 4.2 mm.

Mechanical Testing

The compressive properties of samples of 4 mm in diameter were measured using an Instron 3366 testing frame (Instron, Norwood, Mass.) with a crosshead speed of 2 mm/min, with a 100 N capacity load cell. Samples were conducted in air between force plates until maximum compression was reached. The linear elastic modulus was calculated using a least-squared fitting in the linear region of initial compression up to a 20% strain point.

FTIR Measurements

FTIR analysis of hydrogel samples was performed in a JASCO FTIR 6200 spectrometer (JASCO, Tokyo, Japan) in attenuated total reflectance (ATR). Hydrogels were let to dry on a glass slide. For each sample, 64 scans were coded with a resolution of 1 $cm^{-1}$, with a wavenumber range from 4000-600 $cm^{-1}$.

Horseradish peroxidase (HRP) and Glucose oxidase (GOx) stabilization and detection.

Prior to hydrogel and nanofibrillar material formation, HRP and GOx were mixed with silk solution yielding a final concentration of 2.5 U/ml and 2.5 U/ml for HRP and GOx respectively. After supercritical drying the silk fibroin nanofibrillar materials, samples of the same dimension were separated and stored at different temperatures (4° C., 25° C., and 60° C.) along with liquid samples with a concentration of 2.5 U/ml to be measured at different time points. For HRP, 100 μl 3,3',5,5'-tetramethylbenzidine (TMB) liquid solution (Sigma Aldrich, USA) was added to nanofibrillar materials sample to monitor a reduction at 370 nm using a microplate reader (SpectraMax M2, Molecular Devices, Sunnyvale, Calif., USA).

For GOx, 50 μl of Amplex® Red Glucose Oxidase assay solution (Invitrogen, USA) was added to individual nanofibrillar material samples along with 50 μl of reaction buffer. The fluorescence detection of resorufin, indicative of the reaction of Amplex® Red with hydrogen peroxide generated from the reaction of glucose oxidase with glucose, was measured at 590 nm using 530 nm excitation using a microplate reader (SpectraMax M2, Molecular Devices, Sunnyvale, Calif., USA). A standard curve of glucose was used as a standard and reference.

PtTFPP Oxygen Measurements

Prior to nanofibrillar material formation, silk fibroin nanofibrillar materials were dehydrated with a final rinse in 100% ethanol mixed with platinum(II) meso-tetrakis(pentafluorophenyl)porphyrin (PtTFPP) and left for 24 h to ensure PtTFPP attachment to the silk fibroin.

Oxygen measurements were taken using a cuvette reader (SpectraMax M2, Molecular Devices, Sunnyvale, Calif., USA) with excitation 405 nm and emission at 645 nm at 0% oxygen saturation and 20% oxygen saturation. Nanofibrillar material samples were cycled repeatedly at different oxygen saturations for one minute intervals to monitor the cyclical behavior of the fluorescence intensity. Samples were kept at different temperatures to calculate any changes in degradation. Silk films and ethanol solutions were used as controls.

Example 3

The present Example describes synthesis and characterization of silk fibroin nanofibrillar materials and the effect that varying pressure during supercritical drying has on nanofibrillar material properties.

Materials and Methods

Silk Nanofibrillar Material Synthesis

Acetone Optima (Fisher Scientific) was used to synthesize the initial hydrogel. Acetone was set in a glass Petri dish. Silk solutions of varying concentration were added drop wise into the acetone bath over a period of 30 minutes. The ratio of silk solution to acetone was typically not more than 2:1 because the addition of more silk fibroin produced less transparent gels. The acetone was evaporated at room temperature for 12 hours while adding deionized water to prevent the hydrogel from collapsing. The hydrogel was soaked in a 20 mM solution of EDTA (pH=8.5, Sigma Aldrich) for 24 hours to improve the hydrogel mechanical properties. The hydrogels were rinsed in deionized water followed by dehydration in a series of ethanol rinses at concentrations of 50%, 70%, 80%, 90%, 95%, 100%, and 100% for 30 minutes to be prepared for supercritical carbon dioxide ($SCCO_2$) drying conducted at 50° C. and dried at 250 psi, 500 psi, 750 psi, 1000 psi, 1200 psi, 1400 psi, 1600 psi, and 1800 psi.

Congo Red Staining and Imaging

Silk fibroin nanofibrillar materials were prepared using the method as described above and dissolved in warm water and mixed for several hours. Liquid samples (10 μl) of the aggregated protein were cast onto glass slides and set to air dry at room temperature. When the samples were dry, 200 μl of saturated Congo Red solution in 80% ethanol with saturated NaCl was added to the dried protein sample and blotted to remove the excess solution and dried at room temperature. See M. R. Nilsson, Methods, 2004, 34, 151-60, the entire contents of which are hereby incorporated by reference herein. Insulin control samples were dissolved in water with a concentration of 1 mg/ml. Precipitation of the insulin solution was induced by reducing the pH to 1.5 and heating at 60° C. for 24 hours. Control insulin was left untouched.

Samples were imaged using a CRI Nuance multispectral camera scanning from 450-700 nm with 50 nm step intervals. Polarized light microscopy was used to image each sample with two linear polarizers crossed at a 90-degree angle to each other.

X-Ray Scattering

Measurements of x-ray scattering patterns from the silk samples were conducted at room temperature using an Oxford Diffraction Xcalibur PX Ultra System (Oxford Diffraction Ltd., Concord, Mass.). The $CuK^{\alpha}$ X-ray beam with 1.542 Å was generated at 45 kV/40 mA using an Enhance Ultra. The X-ray beam was focused to 0.3 mm×0.3 mm. A two-dimensional Onyx CCD detector (Oxford Diffraction Ltd., Concord, Mass.) was placed 62 mm from the sample position. Exposure time was 150 s.

Results

Congo Red Analysis of Silk Fibroin Nanofibrillar Materials

Figure 12:
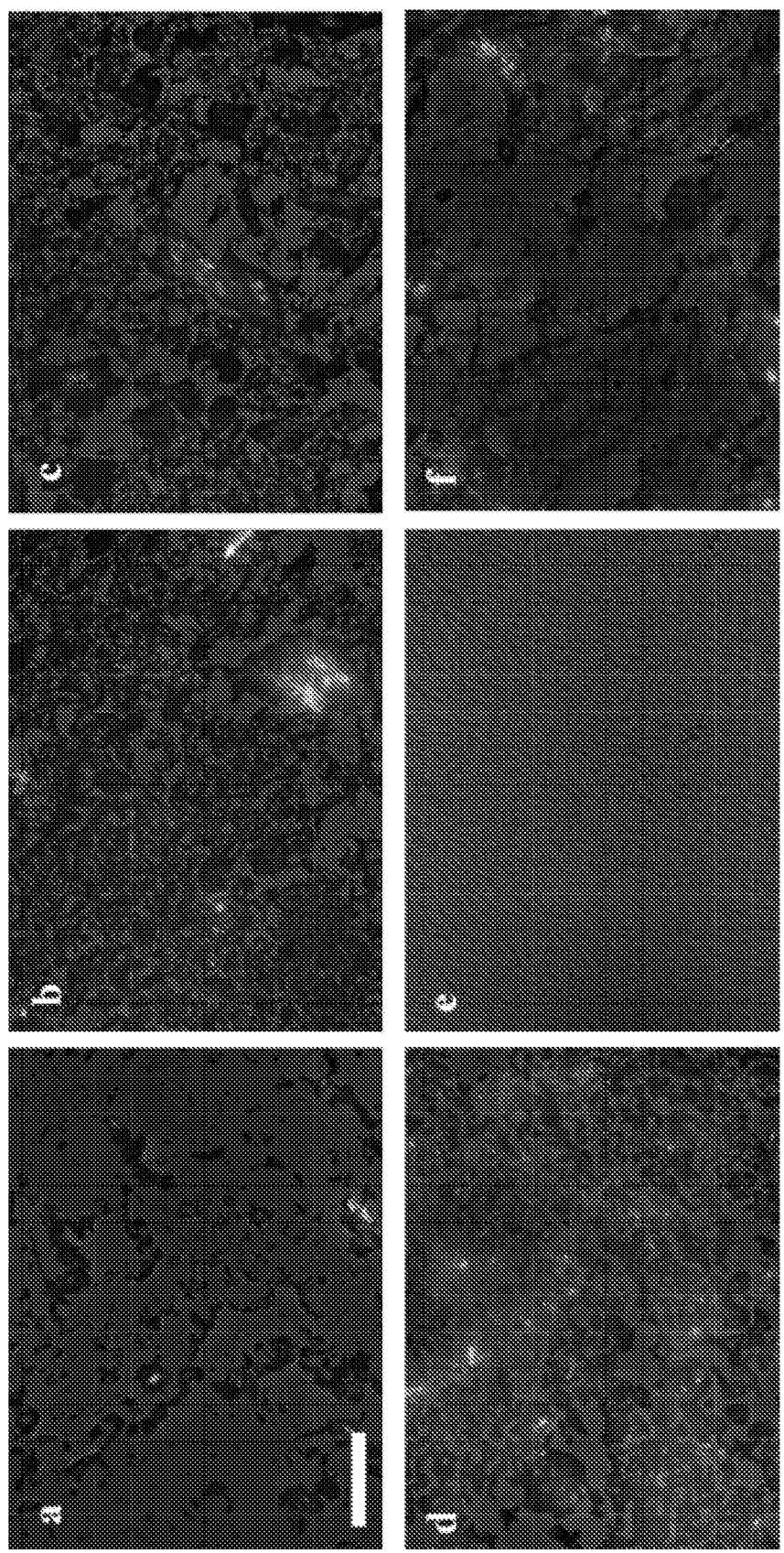
FIG. 12 shows a Congo Red analysis of silk fibroin nanofibrillar materials dried at high pressures.
Figure 13:
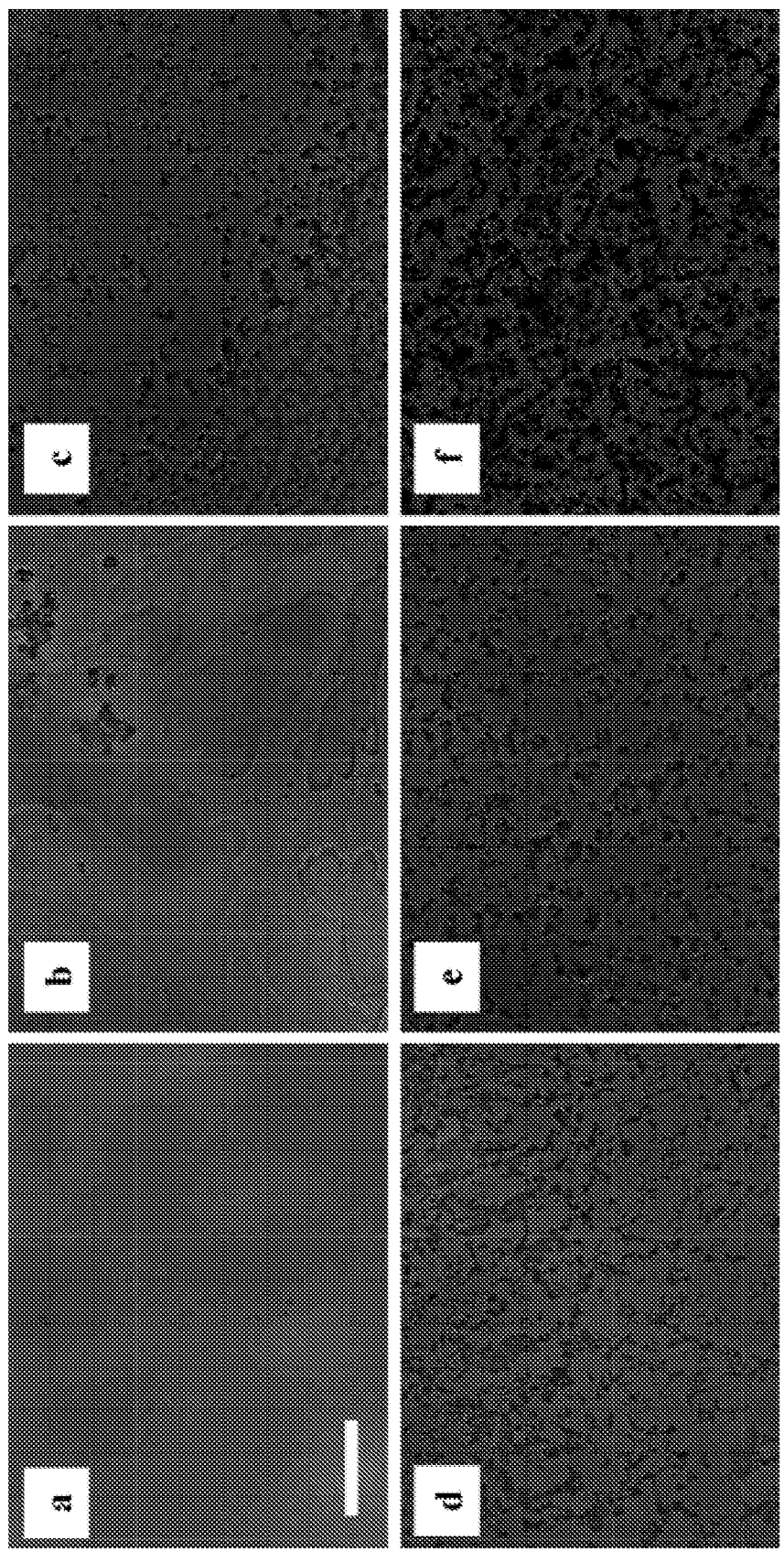
FIG. 13 shows a Congo Red analysis of silk fibroin nanofibrillar materials dried at low pressures.

Polarized light microscopy was used to characterize the structure of the silk nanofibrillar materials as the particle fibroin transitioned into a fibrillar structure after high pressure drying. The highly repetitive primary sequence of silk fibroin makes it desirable among fibrous proteins by bestowing some structural characteristics with predefined fibril structures. See I. Cherny and E. Gazit, Angew. Chem. Int. Ed. Engl., 2008, 47, 4062-9, the entire contents of which are hereby incorporated by reference herein. Silk's transition from an unstructured state into a stable β-structure provides evidence molecular movement occurs and was tested by staining with Congo Red to search for green birefringence (considered a positive result for birefringence). See M. R. Nilsson, Methods, 2004, 34, 151-60; see also S. H. Waterhouse and J. A. Gerrard, Aust. J. Chem., 2004, 57, 519, the entire contents of both are hereby incorporated by reference herein. FIG. 12 and FIG. 13 show images reflecting high and low pressure critical point drying. Fibrils form from a range of storage conditions and their dimensions can be controlled by varying temperature, pH, and the native protein structure. L. J. Domigan, J. P. Healy, S. J. Meade, R. J. Blaikie, and J. A. Gerrard, Biopolymers, 2012, 97, 123-33, the entire contents of both are hereby incorporated by reference herein. Pressure is a characteristic perturbant in studies of protein folding and has acted as a new influence to induce fibrils depending on the protein species. See F. Meersman, C. M. Dobson, and K. Heremans, Chem. Soc. Rev., 2006, 35, 908-17; see also J. Torrent, M. T. Alvarez-Martinez, M.-C. Harricane, F. Heitz, J.-P. Liautard, C. Balny, and R. Lange, Biochemistry, 2004, 43, 7162-70, the entire contents of both are hereby incorporated by reference herein.

FIG. 12 shows Congo Red analysis of silk fibroin nanofibrillar materials dried at high pressures. The analysis of Congo Red stained protein samples at different conditions showed a pressure driven change by the presence of the green birefringence at high pressure drying (1200-1800 psi).

Congo Red birefringence assay was developed to examine fibril structure. Samples were stained with Congo Red and examined under polarized light microscopy. FIG. 12a through FIG. 12d show that when the polarizers are crossed at a 90 degree angle to each other, any bright spots are a result of birefringence. Congo red images of silk fibroin gels dried at pressures above the critical point of $CO_2$ for 1200 psi as shown in FIG. 12a, for 1400 psi as shown in FIG. 12b, for 1600 psi as shown in FIG. 12c, and for 1800 psi as shown in FIG. 12d. FIG. 12e and FIG. 12f show polarized light microscope images of insulin controls for an insulin solution as shown in FIG. 12e and for precipitated insulin as shown in FIG. 12f. (Scale bar is 160 μm).

FIG. 13 shows Congo Red analysis of silk fibroin hydrogels dried at low pressures. Congo Red birefringence assay was developed to examine silk material structure. FIG. 13a through FIG. 13f show samples that were stained with Congo Red and examined under polarized light microscopy. Congo red images show silk fibroin gels dried at different pressures for FIG. 13a, a silk solution, for FIG. 13b, a silk hydrogel, for FIG. 13c, a silk gel dried at 200 psi, for FIG. 13d, a silk gel dried at 500 psi, for FIG. 13e, a silk gel dried at 750 psi, and for FIG. 13f, a silk gel dried at 1000 psi. (Scale bar is 160 μm).

When the polarizers are crossed at a 90 degree angle to each other, any bright spots are a result of birefringence. FIG. 13 shows a lack of green birefringence at lower pressure drying when compared with high pressure drying shown in FIG. 12. As a control, precipitated insulin, FIG. 12f (discussed above) was examined under polarized microscopy revealing similar illuminated green spots as the silk fibroin nanofibrillar materials dried at pressures above the supercritical point of carbon dioxide. As shown in FIG. 13a through FIG. 13f, the silk film, silk hydrogel, and silk hydrogels dried at pressures ranging from 200-1000 psi were absent of such birefringence and were more similar to the soluble insulin control.

X-Ray Scattering of Silk Fibroin Materials

Figure 14:
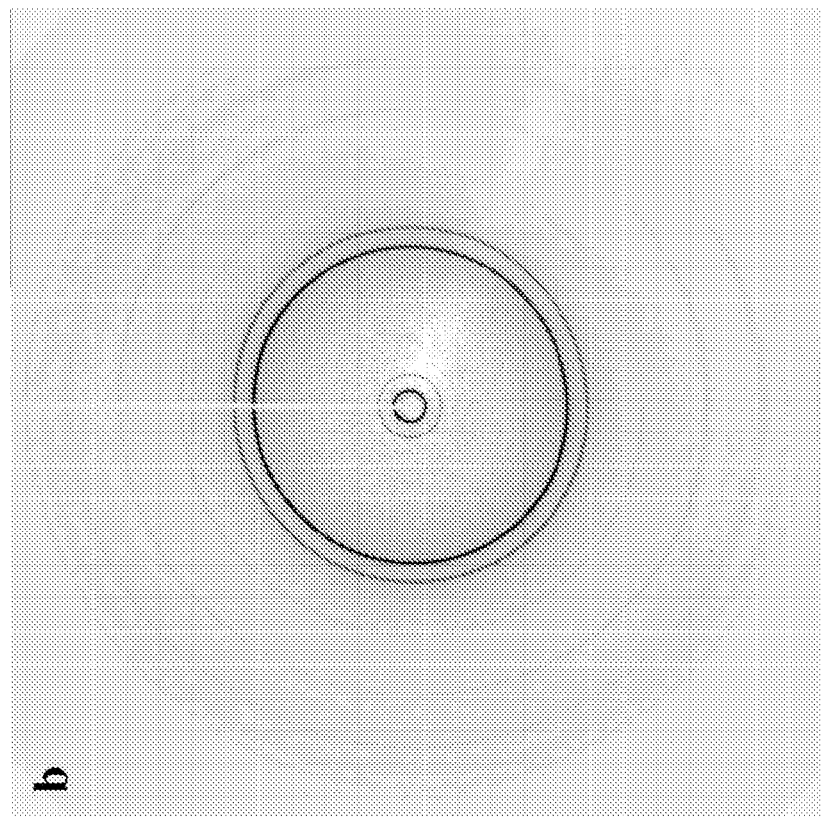
FIG. 14 shows X-ray scattering images of silk nanofibrillar materials.
Figure 14:
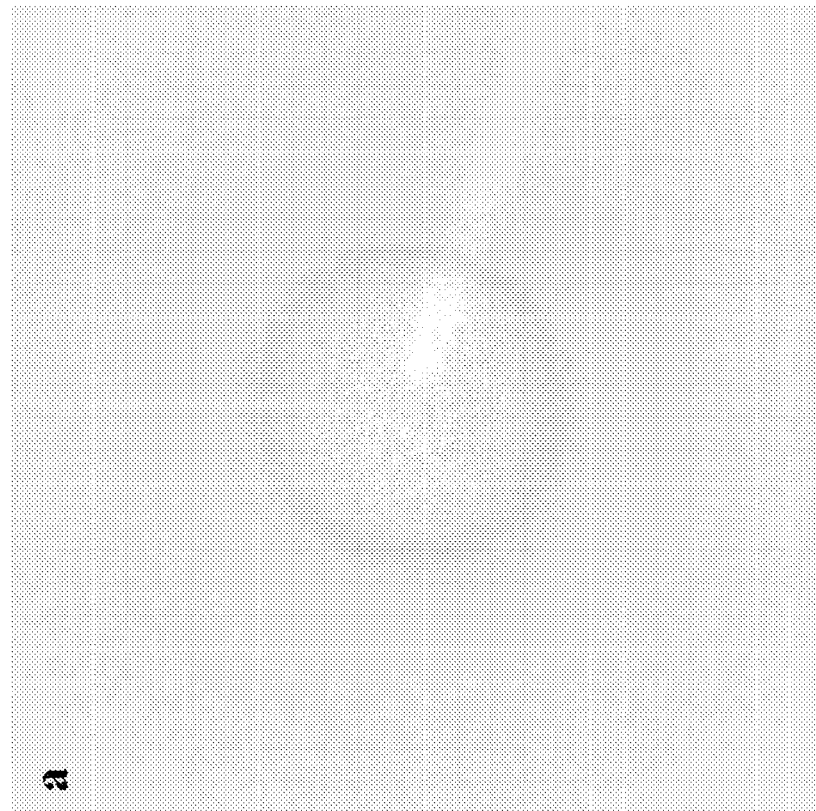

FIG. 14 shows Images of 2D X-ray scattering patterns of silk materials. FIG. 14a shows a 2D X-ray scattering pattern for a silk hydrogel formed by ketonic gelation. FIG. 14b shows a 2D X-ray scattering pattern for a $CO_2$ supercritically dried silk nanofibrillar material, dried at 1800 psi. As shown in FIG. 14, there is a clear difference when comparing the hydrogel X-ray scattering pattern (FIG. 14a) with the X-ray scattering pattern of the silk nanofibrillar material dried at 1800 psi (FIG. 14b). The difference in pattern, particularly the high intensity bands depicted in the silk nanofibrillar pattern (FIG. 14b) signify a molecular change due to the high pressure drying of the supercritical carbon dioxide drying.

Figure 15:
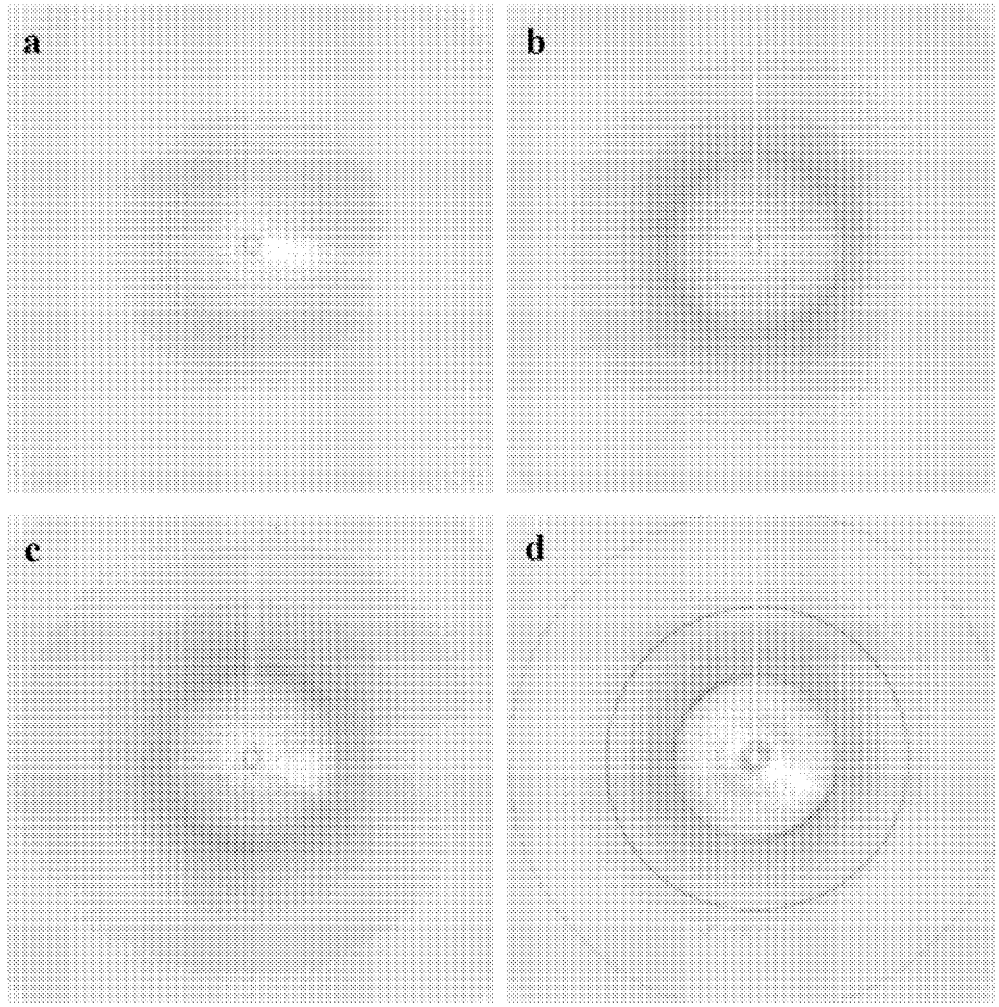
FIG. 15 shows X-ray scattering images of silk materials in a control group for comparison to X-ray scattering images of silk nanofibrillar materials as shown in FIG. 14.

FIG. 15 shows images of 2D X-ray scattering patterns of silk materials. FIG. 15a and FIG. 15b show regenerated amorphous silk films and methanol treated cross-linked silk films and reflect differences in other processing conditions. FIG. 15a shows a 2D X-ray scattering pattern for a regenerated amorphous silk film. FIG. 15b shows a 2D X-ray scattering pattern for a methanol treated cross-linked silk film. FIG. 15c and FIG. 15d show a control group for comparison with FIG. 15a and FIG. 15b. FIG. 15c shows a 2D X-ray scattering pattern for a raw silk fiber (non-heat treated). FIG. 15d shows a 2D X-ray scattering pattern for a precipitated insulin control.

OTHER EMBODIMENTS AND EQUIVALENTS

While the present disclosure has explicitly discussed certain particular embodiments and examples of the present disclosure, those skilled in the art will appreciate that the invention is not intended to be limited to such embodiments or examples. On the contrary, the present disclosure encompasses various alternatives, modifications, and equivalents of such particular embodiments and/or example, as will be appreciated by those of skill in the art.

Accordingly, for example, methods and diagrams of should not be read as limited to a particular described order or arrangement of steps or elements unless explicitly stated or clearly required from context (e.g., otherwise inoperable). Furthermore, different features of particular elements that may be exemplified in different embodiments may be combined with one another in some embodiments.

What is claimed is:

1. A nanofibrillar material, comprising:
nanofibrils formed from an amphiphilic polypeptide, wherein the nanofibrils have an average diameter between about 2 nm and about 40 nm and form a network of interconnected pores,
wherein a majority of the interconnected pores are nano-sized pores that range in diameter between about 2 nm and about 100 nm, and wherein at least 50% of the nano-sized pores are in the mesoporous range in diameter between 2 nm and 50 nm; and
wherein the nanofibrillar material is characterized by a porosity of at least about 80%, a bulk density that is less than about 75 kg/m$^3$, and
a compressive modulus between that is between about 50 kPa and about 300 kPa.

2. The nanofibrillar material of claim 1, wherein the amphiphilic polypeptide comprises a beta-sheet secondary structure.

3. The nanofibrillar material of claim 1, wherein the amphiphilic polypeptide comprises an amino acid sequence of polypeptides selected from the group consisting of:

actins, catenins, claudins, coilins, collagens, elastins, elaunins, extensins, fibrillins, fibroins, keratins, laminins, lamins, tublins, viral structural proteins, zein proteins (seed storage protein) or combination thereof.

4. The nanofibrillar material of claim 1, wherein the amphiphilic polypeptide comprises a silk fibroin polypeptide.

5. The nanofibrillar material of claim 1, wherein the amphiphilic polypeptide has an average molecular weight between 30 kDa and about 400 kDa.

6. The nanofibrillar material of claim 4, wherein the silk fibroin polypeptide comprises a wild type amino acid sequence of *Bombyx mori* fibroin.

7. The nanofibrillar material of claim 4, wherein the silk fibroin polypeptide comprises a variant of *Bombyx mori* fibroin.

8. The nanofibrillar material of claim 4, wherein the silk fibroin polypeptide is a low molecular weight silk fibroin polypeptide having a molecular weight between 30 kDa and about 125 kDa.

9. The nanofibrillar material of claim 1, wherein the nanofibrillar material is characterized by a porosity of at least about 90%.

10. The nanofibrillar material of claim 1, further comprising platinum(II) meso-tetrakis(pentafluorophenyl)porphyrin (PtTFPP) for oxygen sensing.

11. The nanofibrillar material of claim 1, further comprising an additive.

12. The nanofibrillar material of claim 11, wherein the additive is or comprises one or more a therapeutic agent, a preventative agent, and a diagnostic agent.

* * * * *